US009428775B2

(12) United States Patent
Kim et al.

(10) Patent No.: US 9,428,775 B2
(45) Date of Patent: Aug. 30, 2016

(54) TRANSFORMANT FOR PRODUCTION OF LACTIC ACID OF HIGH OPTICAL PURITY AND METHOD FOR PRODUCING LACTIC ACID USING THE SAME

(75) Inventors: Jae-Young Kim, Seoul (KR); Sang-Heum Shin, Seoul (KR); Hyon-Yong Chong, Seoul (KR); Kap-Seok Yang, Seoul (KR); Jeong-Sun Seo, Seoul (KR)

(73) Assignee: Macrogen Inc., Seoul (KR)

( * ) Notice: Subject to any disclaimer, the term of this patent is extended or adjusted under 35 U.S.C. 154(b) by 329 days.

(21) Appl. No.: 14/001,123

(22) PCT Filed: Feb. 23, 2011

(86) PCT No.: PCT/KR2011/001240
§ 371 (c)(1), (2), (4) Date: Oct. 29, 2013

(87) PCT Pub. No.: WO2012/115290
PCT Pub. Date: Aug. 30, 2012

(65) Prior Publication Data

US 2014/0128635 A1 May 8, 2014

(51) Int. Cl.

| | |
|---|---|
| ***C12N 1/20*** | (2006.01) |
| ***C12N 15/00*** | (2006.01) |
| ***C12N 9/04*** | (2006.01) |
| ***C07H 21/04*** | (2006.01) |
| ***C12P 7/56*** | (2006.01) |
| ***C12N 15/74*** | (2006.01) |
| ***C07C 59/08*** | (2006.01) |

(52) U.S. Cl.
CPC .................. *C12P 7/56* (2013.01); *C07C 59/08* (2013.01); *C12N 9/0006* (2013.01); *C12N 15/74* (2013.01); *C12Y 101/01028* (2013.01); *Y02P 20/52* (2015.11)

(58) Field of Classification Search
CPC ............................ C12N 9/0006; C12N 15/74
See application file for complete search history.

(56) References Cited

U.S. PATENT DOCUMENTS

| | | | |
|---|---|---|---|
| 6,566,107 | B1 | 5/2003 | Zhang |
| 7,964,382 | B2 | 6/2011 | Ishida et al. |
| 8,383,377 | B2 | 2/2013 | Yanase et al. |
| 8,822,195 | B2 | 9/2014 | Sawai et al. |
| 2007/0105202 | A1 | 5/2007 | Ishida et al. |
| 2009/0162910 | A1 | 6/2009 | Seo et al. |

FOREIGN PATENT DOCUMENTS

| | | |
|---|---|---|
| JP | 09-000247 | 7/1997 |
| JP | 2004-513632 | 5/2004 |
| JP | 4395132 | 1/2010 |
| JP | 2010-158170 | 7/2010 |
| KR | 10-0725021 | 5/2007 |
| WO | 2010/140602 | 12/2010 |

OTHER PUBLICATIONS

Cuong et al. Transformation of Zymomonas mobilis by electroporation. Appl. Microbiol. Biotechnol. 39:305-308. 1993.*
Branden et al. Introduction to Protein Structure, Garland Publishing Inc., New York, p. 247, 1991.*
Adachi, Eri et al., Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value; Journal of Fermentation and Bioengineering, 1998; pp. 284-289; vol. 86, No. 3; Department of Biochemical Engineering & Science, Kyushu Institute of Technology, Iizuka, Fukuoka 820-8502, Japan (6 pages).
Ishida, N. et al., "D-lactic acid production by metabolically engineered *Saccharomyces cerevisiae*," Journal of Bioscience and Bioengineering. vol. 101 (2), pp. 172-177, Feb. 2006.
Lawford, H. et al., "Steady-state measurements of lactic acid production in a wild-type and a putative D-lactic acid dehydrogenase-negative mutant of Zymomonas mobilis: influence of glycolytic flux," Applied Biochemistry and Biotechnology., vol. 98-100, pp. 215-228, 2002.
NCBI GenBank No. YP 819216 D-lactate dehydrogenase, LdhA [*Leuconostoc mesenteroides* subsp. *mesenteroides* ATCC 8293] Mar. 31, 2010.
NCBI GenBank No. ZP 03913173 D-lactate dehydrogenase [*Leuconostoc mesenteroides* subsp. *cremoris* ATCC 19254] Nov. 10, 2010.
NCBI GenBank No. YP 003772882 D-lactate dehydrogenase [*Leuconostoc gasicomitatum* LMG 18811] Dec. 23, 2010.
NCBI GenBank BAE80313 D-lactate dehydrogenase [*Leuconostoc mesenteroides* subsp. *mesenteroides*] Mar. 8, 2006.
International Search Report and Written Opinion for Application No. PCT/KR2011/001240 dated Nov. 25, 2011 (13 pages).
Lederberg et al., "Gene Recombination in *Escherichia coli*," Nature, Oct. 19, 1946, vol. 158, pp. 558.
Neumann et al., "Gene transfer into mouse lyoma cells by electroporation in high electric fields," The EMBO Journal vol. 1, No. 7 pp. 841-845, 1982.

(Continued)

*Primary Examiner* — Yong Pak
(74) *Attorney, Agent, or Firm* — Michael Best & Friedrich LLP

(57) ABSTRACT

Disclosed is the biological production of lactic acid using a microorganism. A transformant capable of producing lactic acid of high optical purity at high yield, a method for the preparation thereof, and a method for producing lactic acid in a convenient and economically beneficial manner using the same are provided. The *Zymomonas mobilis* transformant can produce lactic acid of high optical purity at high yield without a stringent limitation to production conditions and a regulation of the intracellular metabolism pathway. Because it requires no additional separation and purification steps, the use of the transformant allows the production of lactic acid in a short process, resulting in a significant reduction in production cost, and avoiding the environment problems caused by precipitate wastes, which brings about environmental issues.

3 Claims, 3 Drawing Sheets

(56) References Cited

OTHER PUBLICATIONS

Rakoczy-Trojanowska, "Alternative Methods of Plant Transformation—A Short Review," Cellular & Molecular Biology Letters, pp. 849-858, 2002.
Zhang et al., "Metabolic Engineering of a Pentose Metabolism Pathway in Ethanologenic Zymomonas mobilis," Science, Jan. 13, 1995, 267, pp. 240-243.
Alberts et al., "Chapter 5: DNA Replication, Repair, and Recombination," Molecular Biology of the Cell (4th ed.), New York: Garland Science, 2002, pp. 275-285.
Dequin et al., "Mixed Lactic Acid-Alcoholc Fermentation by *Saccharomyes cerevisiae* Expressing the Lactobacillus csaei L(+)-LDH," Biotechnology(New York), Feb. 12, 1994, 12(2):173-177.
Korean Patent Office Action for Application No. 10-2011-0015911 dated Aug. 24, 2013 (3 pages).

* cited by examiner

TRANSFORMANT FOR PRODUCTION OF LACTIC ACID OF HIGH OPTICAL PURITY AND METHOD FOR PRODUCING LACTIC ACID USING THE SAME

BACKGROUND OF THE INVENTION

1. Field of the Invention

The present invention relates to biological production of lactic acid using a microorganism. More specifically, the present invention relates to a transformant being capable of producing lactic acid with a high optical purity at high yield, and a method for producing lactic acid in a convenient and economically beneficial manner using the same.

2. Description of the Related Art

Polylactic acid (PLA) is an aliphatic polyester produced by polycondensation of lactides which is used as a material for bioplastics. Finding important applications in various fields including electronic appliance packing, water bottles, interior materials of automobiles, office furniture, engineering plastics, and fibers, PLA is known for its use as a future material for biodegradable bioplastics. Together with the Global Environment Movement, which has actively been developed worldwide, an upsurge in concern about global warming and climate change compelled the need of environment-friendly, next-generation fiber materials. In consideration of this situation and trend, PLA biodegradable fibers are considered as having extensive potential because they are naturally recyclable, produce no pollution, and have physicochemical and mechanical properties similar to those of synthetic fibers in addition to being biologically degradable. In spite of the potentials, however, biodegradable fibers are little commercialized because they still require production cost 5-~10-fold higher than that of general synthetic fibers and their mass production is hampered by many difficulties. Further, their uses according to property still remain undeveloped.

Lactic acid (or lactate) has been widely used as a practical commodity chemical in various areas including medicines, food and food processing, cosmetics, chemical substances, etc. In recent years, it has aroused keen interest for its use as a material of the biodegradable polymer PLA (polylactic acid). An upsurge in the demand of lactic acid has provoked the active development of related techniques.

In animals, L-lactate is constantly produced from pyruvate via lactate dehydrogenase in a process of the oxidation of carbohydrates. Lactic acid is an enantiomer in the form of L-(+)-lactic acid or D-(−)-lactic acid. The production of lactic acid may be achieved by a chemical process, but resorts to a biological conversion method using microorganisms in most practical cases.

Commonly, a fermentative production process of lactic acid comprises (1) fermentation, (2) removal of cell mass and proteins, (3) separation and purification of lactic acid, (4) concentration of lactic acid, and (5) dehydration. Fermentative production processes of lactic acid have focused, for the most part, on production techniques by increasing plant scale and production yield through the development of new production processes and the modification of production processes, and on the cost reduction and yield improvement of the separation and purification process by developing excellent separation and purification techniques such as in economically beneficial evaporators and membranes, as well as in dehydration process.

More recently, research and development has been directed to fermentative microorganisms highly advantageous in temperature, pH and organic product productivity, with the advance of various analysis and metabolism engineering techniques. In order to produce lactic acid with high optical selectivity and purity, fermentative processes require higher production costs than do petroleum processes. In addition, fermentative production is economically limited in producing lactic acid of various qualities which have applications in various fields.

Unlike petrochemical processes, fermentative production processes of lactic acid rely absolutely on lactic acid-producing microorganisms. First of all, thus, it is important to secure microorganisms capable of producing lactic acid of high optical purity in terms of mass production capacity and product cost. The mass production of lactic acid with high optical necessarily needs a multi-stage separation and purification process as well as a large amount of raw materials, which results in a rapid increase in production costs. Together with a mass production technique, a microorganism strain capable of lactic acid with high optical selectivity and purity is therefore a prerequisite. In this context, systemic analysis, and metabolism engineering technologies should be provided for optimizing metabolic flux, in combination with a gene allowing for producing lactic acid with excellent optical selectivity.

On the whole, microorganisms used in the production of lactic acid grow at mid temperatures (30-37° C.) and neutral acidity (e.g., pH 7.0). Particularly, lactic acid-producing microorganisms are very sensitive to pH, so that they survive and actively grow only in a narrow pH range while producing lactic acid. In a lactic acid-producing process, the product lactic acid itself is weakly acidic, thus acidifying the environment of the microorganisms. To keep an optimal pH for the fermentation, e.g., a neutral pH, a base such as NaOH, $(NH_4)OH$, $Ca(OH)_2$ and the like, or a carbonate (e.g., $CaCO_3$) is added incessantly. At a pH of 7.0, lactic acid is completely ionized, and thus exists as a salt (lactate). The separation and purification of the lactic acid salt (lactate) into lactic acid needs protonation which can be accomplished with a strong acid such as sulfuric acid. The addition of one mole of sulfuric acid affords two moles of lactic acid with the concomitant production of one mole of a sulfate precipitant (e.g., $CaSO_4$).

Hence, sulfuric acid is required in the same amount (half the amount) as the lactic acid produced. This means with an increase in the recovery and purification of lactic acid, there is also an increase in the expense of sulfuric acid. Besides, the addition of sulfuric acid evokes the problem of causing an expense of precipitate disposal and producing precipitates as an environment pollutant, and thus is economically disadvantageous. There is therefore a pressing need for both a microorganism capable of producing lactic acid even at high acidity (acidic pH), and a technique by which lactic acid or lactate salts can be recovered and purified without producing precipitate wastes.

SUMMARY OF THE INVENTION

In considering the above problems in the prior art, the present invention is to provide a transformant which can produce lactic acid at high yield without requiring a limited pH condition and modifying an intracellular metabolism pathway, and which allows the production of lactic acid with a high optical purity without a separate separation and purification process, a method for the preparation thereof, and a method for producing lactic acid using the same.

The present inventors have researched a lactic acid-producing microorganism capable of mass production of lactic acid having a high optical purity, and found that that

*Zymomonas mobilis* transformed with a gene encoding a D-lactate dehydrogenase derived from *Leuconostoc* sp., guarantees D-lactate dehydrogenase activity and produces lactic acid at high yield through a very simple and easy process, without limitations to addition complex process and production conditions.

The present invention is to provide a *Zymomonas mobilis* transformant, comprising a gene encoding a D-lactate dehydrogenase derived from *Leuconostoc* sp.

The present invention to provide a method for preparing a *Zymomonas mobilis* transformant, comprising: providing a *Zymomonas mobilis* strain; and introducing a gene encoding a D-lactate dehydrogenase derived from *Leuconostoc* sp into the *Zymomonas mobilis* strain.

Also, the present invention is to provide a method for producing lactic acid, comprising:

introducing a gene encoding a D-lactate dehydrogenase derived from *Leuconostoc* sp into *Zymomonas mobilis* to prepare a *Zymomonas mobilis* transformant; and culturing the *Zymomonas mobilis* transformant.

Further, the present invention is to provide a lactic acid which is produced using the production method, and has a high optical purity.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
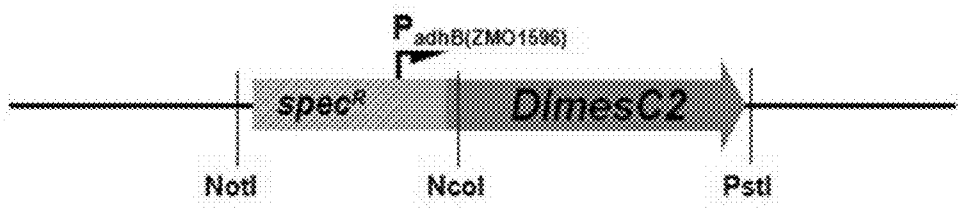
FIG. 1 is a schematic diagram showing the expression unit of a gene encoding D-lactate dehydrogenase as represented by the nucleotide sequence of SEQ ID NO: 1.

A detailed description of the present invention will be given as below.

Lactic acid (lactate) is a organic compound including a chiral carbon (chemical formula: $C_3H_6O_3$) containing the four groups of carboxyl, hydroxyl, methyl, and hydrogen. Lactic acid include all stereo-isomers of D-, L-, or DL-form. Preferable is D-lactic acid.

In an aspect of the present invention, there is provide a *Zymomonas mobilis* transformant including a gene encoding a D-lactate dehydrogenase derived from *Leuconostoc* sp, in order to produces lactic acid at high yield.

In accordance with another aspect, there is provided a method for preparing *Zymomonas mobilis* transformant, comprising: providing a *Zymomonas mobilis* strain; and introducing a gene encoding a D-lactate dehydrogenase derived from *Leuconostoc* sp into the *Zymomonas mobilis* strain.

The alcohol fermentation bacterium *Zymomonas mobilis* is suitable for introducing a gene coding for D-lactate dehydrogenase, because it has a higher conversion rate to metabolite than the cell growth rate.

By using *Zymomonas mobilis* transformant in the production of lactic acid, the production of a lactic acid is remarkably increased, without a complicate regulation of the lactate metabolism pathway by, for example, allowing the blocking of a certain step in the lactate metabolism pathway of *Zymomonas mobilis* produce other primary metabolite than the primary metabolite produced in the blocked pathway.

As used herein, the term "transformation" refers to a molecular biological phenomenon meaning genetic alteration of a cell resulting from the uptake, incorporation and expression of exogenous genetic material (DNA fragment, plasmid, etc.).

Particularly in the present invention, the transformation means the introduction of a gene encoding D-lactate dehydrogenase into *Zymomonas mobilis*, and the 'transformant' means a *Zymomonas mobilis* strain transformed with the gene, and is preferably a *Zymomonas mobilis* strain anchoring therein the gene (Dldh-Lmes1801/DlmesC2) having a nucleotide sequence as set forth in SEQ ID NO: 1, identified as the strain deposited under an accession No. of KCTC 11803BP.

The gene encoding D-lactate dehydrogenase may be derived from a *Leuconostoc* sp., but is not limited thereto. In one embodiment, the gene may code the amino acid sequence as set forth in SEQ ID NO: 2, or an amino acid sequence having an identity of 40% or higher with SEQ ID NO: 2.

In a preferred embodiment, the gene may code a polypeptide having the amino acid sequence as set forth in SEQ ID NO: 2, SEQ ID NO: 4, SEQ ID NO: 6, or SEQ ID NO: 8.

The amino acid sequence of SEQ ID NO: 2 may be coded by the nucleotide sequence of SEQ ID NO: 1, the amino acid sequence of SEQ ID NO: 4 coded by the nucleotide sequence of SEQ ID NO: 3, the amino acid sequence of SEQ ID NO: 6 coded by the nucleotide sequence of SEQ ID NO: 5, and the amino acid sequence of SEQ ID NO: 8 coded by the nucleotide sequence of SEQ ID NO: 7.

Accordingly, the gene coding for D-lactate dehydrogenase may have the nucleotide sequence as set forth in SEQ ID NO: 1 or a nucleotide sequence having a similarity of 85% or higher with SEQ ID NO: 1, but is not limited thereto.

In a preferred embodiment, the gene may have the nucleotide sequence as set forth in SEQ ID NO: 1 (Dldh-Lmes1801), the nucleotide sequence as set forth in SEQ ID NO: 3 (ldhD-ATCC19254), the nucleotide sequence as set forth in SEQ ID NO: 5 (ldhD1-LMG18811), or the nucleotide sequence as set forth in SEQ ID NO: 7 (D-ldh-NBRC3426).

The introduction of the gene may be preferably achieved by a process selected from the group consisting of, but not limited to, conjugation, electroporation, and a gene gun.

Conjugation is the transfer of DNA between cells (donor cell and recipient cell) through conjugative pili on cell surfaces (Lederberg and Tatum, Nature. October 19; 158 (4016): pp. 558. 1946).

Electroporation is the temporary formation of nanopores on the cell plasma membrane by an externally applied electrical impact, through which cellular DNA uptake is increased (Neumann et al., The EMBO Journal Vol. 1 No. 7 pp. 841-845, 1982; Cellular & Molecular Biology Letters, pp 849-858, 2002). The gene gun is configured to inject a gene into a cell by firing a gene-coated metal (tungsten or gold) with a highly pressurized gas (Cellular & Molecular Biology Letters, pp 849-858, 2002).

No particular limitations are imposed on the intracellular site of *Zymomonas mobilis* where the gene is introduced. Once introduced into the cell, the gene allows it to produce lactic acid of high optical purity at high yield and efficiency, irrespective of the intracellular site at which the gene is positioned. Hence, the method of the present invention enjoys the advantage of being very simple and convenient and reducing the production cost.

That is, the gene may be introduced at or near a gene irrelevant to the lactate metabolism pathway of *Zymomonas mobilis*. In addition, since the gene does neither require modifications in the lactate metabolism pathway of *Zymomonas mobilis* nor has influences on the metabolism pathway as described above, it can be introduced to a genetic site relevant to the metabolism pathway.

To quote an example, the gene may be incorporated into ORF ZMO270-ZMO263, ORF ZMO0087~ZMO0089, ORF ZMO0381~ZMO0384, ORF ZMO0390~ZMO0394, or ORF ZMO1786~ZMO1789 in the genome of *Zymomonas mobilis*, or into such a gene involved in the lactate metabolism pathway as an L-lactate dehydrogenase gene (ZMO0256), a D-lactate dehydrogenase gene (ZMO1237), an alcohol dehydrogenase I gene (ZMO1236), or an alcohol dehydrogenase II gene (ZMO1596).

The gene coding for D-lactate dehydrogenase may be carried into *Zymomonas mobilis* by a vector containing a promoter of *Zymomonas mobilis*.

Any vector may be available for the introduction of the gene. For example, it may be a *Zymomonas mobilis* expression vector such as pGMC, pZY507, pZY500, and pZymo, or a typical cloning vector such as pUC series, pBluescript series, and pGEM series. Preferably, the vector may comprise a promoter which can be regulated in *Zymomonas mobilis*, and optionally a selection marker and a conjugator.

The promoter which can potently act in *Zymomonas* may be any promoter useful in the expression of a recombinant protein. An available alternative may be a promoter derived from *Zymomonas mobilis* ZM4. For example, a promoter for the ZM4-derived gene adhI (adhA, ZMO1236), pdc (pdc, ZMO1360) or adhII (adhB, ZMO1596) may be employed. In addition, a 500 bp-DNA upstream of each gene of *Zymomonas mobilis* ZM4 may be available as a promoter. The potent *E. coli* tac promoter can be also used in *Zymomonas* (Zhang et al., Science. 1995. Jan. 13; 267(5195): pp. 240-243).

The selection marker may be an antibiotic-resistance gene, and examples include a spectinomycin-resistance gene, a chloramphenicol resistance gene, an ampicillin resistance gene, and a tetracycline resistance gene, but are not limited thereto.

When designed to be episomal in a host cell, the vector requires a replication origin. It may be OriV origin, which acts in most Gram (−) bacteria. In this case, repA and repB genes may further be required.

Upon transformation into microorganisms, the vector may be integrated into the chromosome or may exist as a plasmid within the cytoplasm, depending on the kind thereof. Integration into the chromosome is applicable to the vector which lacks a replication origin necessary for the replication in *Zymomonas*. In this case, if the chromosome has a segment homologous to a part of the plasmid, the plasmid is inserted to the homologous segment (homologous recombination), resulting in 2 copies of the same gene in tandem (single cross over, gene integration) or substituting the homologous part for the segment of the chromosome (double cross over, gene disruption). If no homologous chromosomal segments exist, random recombination may occurs.

In accordance with a further aspect thereof, the present invention addresses a method for producing lactic acid, comprising: introducing a gene encoding a D-lactate dehydrogenase derived from *Leuconostoc* sp. into *Zymomonas mobilis* to form a *Zymomonas mobilis* transformant; and culturing the *Zymomonas mobilis* transformant.

The culturing may be performed not only at pH 5.0, a normal fermentation condition, but also under an acidic condition or a pH-non-adjusted condition. For example, the transformant may be cultured at a pH of 3.0 to 7.0, a pH of 3.0 to 6.0, or a pH of 3.0 to 5.0, to produce lactic acid.

On the whole, growth conditions for lactic acid-producing bacteria include a mid temperature (30-37° C.) and a neutral pH (e.g., pH 7.0). Particularly since lactic acid-producing microorganisms are very sensitive to pH, they survive and actively grow only in a narrow pH range. In a lactic acid-producing process, the product lactic acid itself is weakly acidic, thus acidifying the environment of the microorganisms. To keep an optimal pH for the fermentation, e.g., a neutral pH, a base such as NaOH, $(NH_4)OH$, $Ca(OH)_2$ and the like, or a carbonate (e.g., $CaCO_3$) is added incessantly. In contrast, the method of the present invention guarantees the production of lactic acid of high optical purity at high yield in any pH condition, without limitations imposed on the pH condition, and thus is very economically beneficial and convenient.

By the method of the present invention, lactic acid of high optical purity can be produced on a mass scale at a yield of as high as 70% to 100%.

Accordingly contemplated in accordance with a still further aspect of the present invention is lactic acid of high optical purity, produced by the method of the present invention.

The lactic acid produced by the method of the present invention has an optical purity of 95% or higher, preferably 99% or higher, and more preferably 99.9% or higher.

According to the present invention, as described above, there are provided a *Zymomonas mobilis* transformant which can produce lactic acid with high optical purity at high yield without a stringent limitation to production conditions and a regulation of the intracellular metabolism pathway, a method for preparing the same, and a method for producing lactic acid using the same.

Because it requires no additional separation and purification steps, the use of the transformant allows the production of lactic acid in a short process, resulting in a significant reduction in production cost, and avoiding the environment problems caused by precipitate wastes, which brings about environmental issues.

A better understanding of the present invention may be obtained through the following examples which are set forth to illustrate, but are not to be construed as the limit of the present invention.

EXAMPLE 1

Preparation of ZM Transformant Anchoring D-Lactate Dehydrogenase Gene (DlmesC2) Therein

Example 1-1

Construction of Plasmid pGEM-T-DlmesC2

From a *Leuconostoc mesenteroides* strain separated from Kimchi, a D-lactate dehydrogenase-encoding DlmesC2 gene (1,068 bp) (SEQ ID NO: 1) was selectively amplified and separated by PCR (pre-denaturation at 96° C. for 5 min; a total of 25 cycles of 96° C. for 30 sec, 60° C. for 30 sec, and 72° C. for 1 min; post-extension at 72° C. for 7 min) in the presence of 0.1 unit of High-Fidelity Platinum Taq DNA Polymerase (Roche) using the following primers.

The primers used in the PCR are as follows:

```
Forward primer (DLmesC2F)
                              (SEQ ID NO: : 9)
5-TGGAGGATCCCATGGTAAAGATTTTTGC-3

Reverse primer (DLmesC2R)
                              (SEQ ID NO: : 10)
5-TGTTTGATTATTCCTGCAGAAACCCCTC-3
```

Subsequently, the PCR product thus obtained was cloned into a pGEM-T Easy vector (Promega) to give a recombinant plasmid pGEM-T-DlmesC2 carrying the DlmesC2 gene, and examined by base sequencing. PCR amplification and cloning were performed according to the instructions of the manufacturers.

Example 1-2

Construction of pBS-del-270::sp-DlmesC2::263 Vector

After the plasmid prepared in Example 1-1 (pGEM-T-DlmesC2) was digested with the restriction enzymes NcoI (NEB) and PstI (NEB), the digest was cloned at the same restriction sites into a pBS-sp-P1596-spec$^R$ vector (Microgen) having a promoter (SEQ ID NO: 11) for *Zymomonas mobilis* alcohol dehydrogenase (adh) II gene (adhB, ZMO1596), and a spectinomycin resistance gene (spec$^R$, 1,142 bp) (SEQ ID NO: 12) to give a recombinant vector carrying the D-lactate dehydrogenase gene (DlmesC2), named pBS-sp-DlmesC2.

The introduction of the D-lactate dehydrogenase gene (DlmesC2) into the chromosome of *Zymomonas mobilis* was achieved by homologous recombination (Alberts et al., 2002. "Chapter 5: DNA Replication, Repair, and Recombination". Molecular Biology of the Cell (4th ed.). New York: Garland Science. p. 845).

Figure 2:
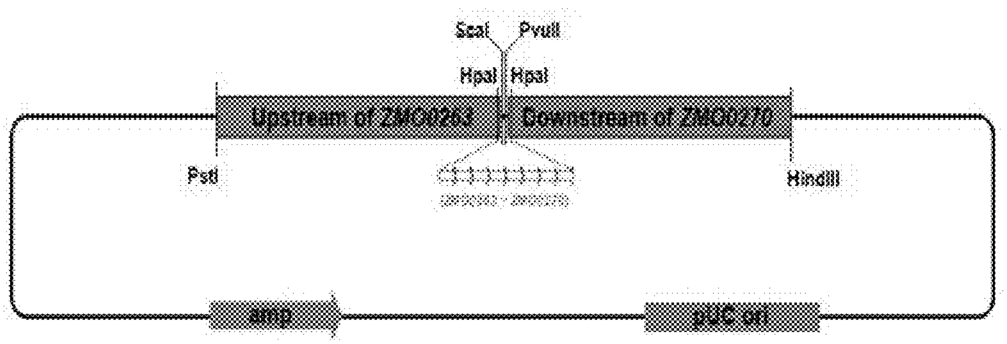
FIG. 2 is a cleavage map of the pBS-del-270::263 vector constructed in Example 1.

For use in the homologous recombination, a gene was chosen with reference to the chromosome data of *Zymomonas mobilis* (ATCC 31821). Briefly, 8 repeated genes of from ORF ZMO0263 to ZMO0270 (SEQ ID NO: 13~SEQ ID NO: 20) were taken. The repeated genes of ORF ZMO0263 to ZMO0270 were found to code for none of enzymes involved in the lactate metabolism pathway, and have a total length of about 10 kb. A 4.468 bp gene (SEQ ID NO: 21) and a 4,935 bp gene (SEQ ID NO: 22) which corresponded respectively to the upstream and the downstream homologous sites of the genes were independently amplified and separated in the same manner as in Example 1-1, and digested with HindIII (NEB), PstI (NEB), PvuI (NEB), and ScaI (NEB). The resulting digests were cloned to a pBluescriptII vector (Stratagene) at the same restriction sites to give a recombinant vector, named pBS-del-270::263 (FIG. 2). The primers used were as follows.

```
Forward primer of upstream gene (L-270F)
                              (SEQ ID NO: 23)
5-GGAAAGTCAAGCTTATCATCTAG-3

Reverse primer of upstream gene (L-270R)
                              (SEQ ID NO: 24)
5-GTGAGTTGTTAACCAATTTTATACTCCATTCATC-3

Forward primer of downstream gene (R263F)
                              (SEQ ID NO: 25)
5-GACAATACAAAGTACTGATAAAGGA-3
```

-continued

```
Reverse primer of downstream gene (R263R)
                              (SEQ ID NO: 26)
5-ATAAGCCTGTTAACTTAccCATCTTGTCCGACG-3
```

Figure 3:
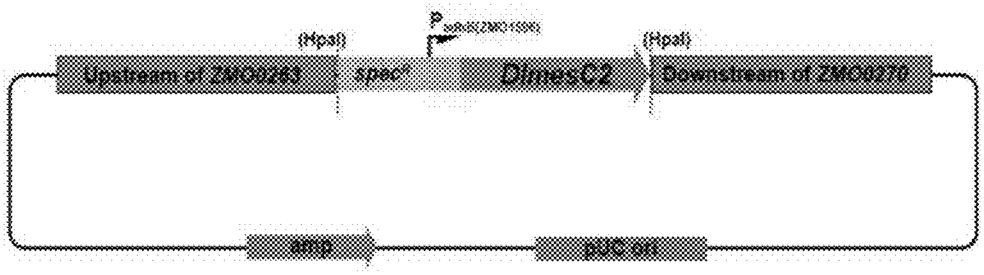
FIG. 3 is a cleavage map of the pBS-del-270::sp-DlmesC2::263 constructed in Example 1.

A spec$^R$-DlmesC2 gene fragment was recovered by cutting the pBS-sp-DlmesC2 vector with NotI (NEB) and PstI (NEB) and then made blunt at both ends by treatment with T4 DNA polymerase (NEB) and T4 polynucleotide kinase (NEB). The resulting blunt-end spec$^R$-DlmesC2 gene was ligated to pBS-del-270::263 at the restriction enzyme HpaI site using T4 DNA ligase (NEB) to afford a recombinant vector, named pBS-del-270::sp-DlmesC2::263 (FIG. 3).

Example 1-3

Construction of ZM Transformant Carrying D-Lactate Dehydrogenase Gene (DlmesC2)

The pBS-del-270::sp-DlmesC2::263 vector constructed in Example 1-2 was transformed into *Zymomonas mobilis* ZM4 (ATCC 31821) by electroporation (Neumann et al., The EMBO Journal Vol. 1 No. 7 pp. 841-845, 1982), followed by culturing in an RM medium (glucose 20 g/l; yeast extract (DIFCO), 10 g/l; $MgSO_4$, 1 g/l; $(NH_4)_2SO_4$, 1 g/l; $KH_2PO_4$, 2 g/l; agar, 15 g/l; pH 5.0) containing spectinomycin to select strains transformed with the pBS-del-270::sp-DlmesC2::263 vector. Finally, a transformant into which the sp-DlmesC2 gene was introduced, with the homogenous recombination of the repeated genes of ORF ZMO0263 to ZMO0270 was designated *Zymomonas mobilis* MG6106, and deposited with the Korean Collection for Type Culture on November fifth, 2010, under accession No. KCTC 11803BP.

EXAMPLE 2

Preparation of Lactic Acid-Producing ZM Strain Anchoring Various D-Lactate Dehydrogenase Genes Therein The D-lactate dehydrogenase genes ldhD-ATCC19254, ldhD1-LMG18811, and D-ldh-NBRC3426 derived respectively from *Leuconostoc cremoris* ATCC 19254, *Leuconostoc mesenteroides* LMG18811, and *Leuconostoc mesenteroides* NBRC3426 strains were amplified by PCR and separated in the same manner as in Example 1. The primers used in the amplification of the D-lactate dehydrogenase genes were as follows:

```
[Primers for amplifying the ldhD-ATCC19254 gene]
ATCC19254F
                              (SEQ ID NO: 27)
5-CATATGAAGATTTTTGCTTACGGCATTCGT-3

ATCC19254R
                              (SEQ ID NO: 28)
5-TTAATATTCAACAGCAATAGCT-3

[Primers for amplifying the ldhD1-LMG18811 gene]
LMG18811F
                              (SEQ ID NO: 29)
5-CATATGAAAATTTTTGCTTACGGCATACG-3

LMG18811R
                              (SEQ 1D NO: 30)
5-CTGCAGTCAGTATTTAACAGCGATTGCA-3
```

-continued

```
[Primers for amplifying the D-ldh-NBRC3426 gene]
NBRC3426F
                                        (SEQ ID NO: 31)
5-CATATGAAGATTTTTGCTTACGGCATTCG-3

NBRC3426R
                                        (SEQ ID NO: 32)
5-CTGCAGTTAATATTCAACAGCAATAGCT-3
```

The individual PCR products thus obtained were digested with the restriction enzymes NcoI (NEB) and PstI (NEB), and cloned into a pBS-sp-P1596-spec$^R$ vector (Microgen) at the same restriction site by ligation in the presence of T4 DNA ligase (NEB) to afford recombinant vectors, named pBS-sp-D-NBRC34261, pBS-sp-D-LMG18811, and pBS-sp-D-ATCC15294 which carries the D-lactate dehydrogenase genes of NBRC3426, LMG18811, and ATCC 15294 strains, respectively.

Digestion of the vectors with the restriction enzymes NotI (NEB) and PstI (NEB) excised spec$^R$-D-NBRC34261, spec$^R$-D-LMG18811, and spec$^R$-D-ATCC15294 gene fragments which were then made blunt at both ends thereof by treatment with T4 DNA polymerase (NEB) and T4 polynucleotide kinase (NEB). The resulting blunt-ended gene fragments were cloned to the pBS-del-270::263 vector constructed in Example 1 at the restriction enzyme HpaI site to give pBS-del-270::sp-D-NBRC34261::263, pBS-del-270::sp-D-LMG18811::263, and pBS-del-270::sp-D-ATCC15294::263 vectors, respectively.

These vectors were transformed into *Zymomonas mobilis* ZM4 (ATCC 31821) by electroporation, followed by culturing in an RM medium (glucose, 20 g/l; yeast extract (DIFCO), 10 g/l; $MgSO_4$, 1 g/l; $(NH_4)_2SO_4$, 1 g/l; $KH_2PO_4$, 2 g/l; agar, 15 g/l; pH 5.0) containing spectinomycin to select transformed strains. Finally, transformants in which the repeated genes of ORF ZMO0263 to ZMO0270 were homogenously recombined were named MG6115 when found to carry the D-lactate dehydrogenase-encoding ldhD-ATCC19254 gene (996 bp) (SEQ ID NO: 3) derived from *Leuconostoc cremoris* ATCC 19254, MG6116 when found to carry the D-lactate dehydrogenase-encoding ldhD1-LMG18811 gene (996 bp) (SEQ ID NO: 5) derived from *Leuconostoc mesenteroides* LMG 18811, and MG6117 when found to carry the D-lactate dehydrogenase-encoding D-ldh-NBRC3426 gene (996 bp) (SEQ ID NO: 7) derived from *Leuconostoc mesenteroides* NBRC 3426.

EXAMPLE 3

Preparation of ZM Strain Anchoring D-Lactate Dehydrogenase Gene in the Chromosome Devoid of Genes or Regions Irrelevant to Lactate Metabolism Pathway To examine the effect on lactic acid production of the site at which the D-lactate dehydrogenase gene was introduced into the host cell, *Zymomonas mobilis* (ATCC 31821) was modified to be devoid of a chromosomal gene or region irrelevant to the lactate metabolism pathway, and to have the DlmesC2 gene having a nucleotide sequence as set forth in SEQ ID NO: 1 integrated into the chromosome at the same site. Briefly, four genes which were found to encode no enzymes and had no genetic information thereon were deleted from the genome of *Zymomonas mobilis* into which the DlmesC2 gene was then introduced. DNA regions, each more than 3000 bp in length, which were respectively positioned upstream and downstream of each gene irrelevant to the metabolism pathway were used in cloning through homogenous recombination

Example 3-1

Construction of Vector Devoid of Three ORFs of ZMO0087 to ZMO0089 and Carrying D-Lactate Dehydrogenase Gene A 3,168 bp DNA fragment (SEQ ID NO: 33) and a 3,159 bp DNA fragment (SEQ ID NO: 34) which were, respectively, positioned upstream of the 5'end and downstream of the 3' end of each of the three ORFs (open reading frames) ZM00087 to ZM00089 were amplified by PCR using a pair of forward (87F) and reverse primers (89R) in the same manner as in Example 1, with the exception that the extension was performed for 10 min.

```
Forward primer (87F)
                                        (SEQ ID NO: 35)
5-TGAAATGGCCTCTGCGATATATCGAATA-3

Reverse primer (89R)
                                        (SEQ ID NO: 36)
5-GTAAGGGTATCGCTCCGCTCTTTATGGCGGA-3
```

The PCR products obtained were treated with the enzyme NotI(NEB), ligated to the pBluescript II 벡터 (Stratagene) treated with the same enzyme to obtain the vector of pBS-ZMO008789.

Using the reverse PCR, the upstream homologous region and downstream homologous region including pBluescript II except for ORF genes ZMO0087~ZMO0089 were selectively amplified. The primers used for the reverse PCR (del 89F and del 87R) were as follows, and the PCR reaction was the same as that of Example 1, except for 10 minutes for extension time.

```
Forward primer (del 89F)
                                        (SEQ ID NO: 37)
5-TAACCCGTTTACCTCTATCATATAATTATA-3

Reverse primer (del 87R)
                                        (SEQ ID NO: 38)
5-CATAAAATTCCTACAAATATGATCTTTTTA-3
```

The PCR products obtained were treated with the enzyme PmeI (NEB), ligated to the sp-DlmesC2 gene fragment of Example 1 in the presence of T4 DNA ligase (NEB), and used to construct a recombinant vector pBS-Del 87::sp-DlmesC2::89.

Example 3-2

Construction of Vector Devoid of Four ORFs of ZMO0381 to ZMO0384 and Carrying D-Lactate Dehydrogenase Gene A 3,140 bp DNA fragment (SEQ ID NO: 39) and a 3,212 bp DNA fragment (SEQ ID NO: 40) which were, respectively, positioned upstream of the 5'end and downstream of the 3' end of each of the four ORFs ZMO0381 to ZMO0384 were amplified by PCR using a pair of forward (381F) and reverse primers (384R) in the same manner as in Example 1, with the exception that the extension was performed for 10 min.

```
Forward primer (381F)
                                        (SEQ ID NO: 41)
5-GAAGAAGCGCAGACCCTATCTCAACGATCTTT-3

Reverse primer (384R)
                                        (SEQ ID NO: 42)
5-CCAAACTGTCCCTTGGCCAGCTTTCAAAAAAAC-3
```

The PCR products thus obtained were treated with the restriction enzyme PmeI (NEB), and cloned to a pBluescript II vector (Stratagene) at the same restriction enzyme site to give a recombinant vector pBS-ZMO0381384.

Subsequently, regions of the pBluescript II vector which were positioned, respectively, upstream and downstream of each of the ORFs ZMO0381~ZMO0384 were selectively amplified by reverse-transcription PCR. The primers used in the reverse-transcription PCR (del 384F and del 381R) were shown as follows. PCR was performed in the same manner as in Example 1, with the exception that 10 min was given to the extension step.

```
Forward primer (del 384F)
                                        (SEQ ID NO: 43)
5-TGTAGTTTATACGCTGCATTAAATGAAAAGG-3

Reverse primer (del 381R)
                                        (SEQ ID NO: 44)
5-TATTTATCCAATGCGCCCCCTGCTTTG-3
```

The resulting PCR products were treated with the restriction enzyme PmeI (NEB), ligated to the sp-DlmesC2 gene of Example 1 in the presence of T4 DNA ligase (NEB), and used to construct a recombinant vector pBS-Del 381::sp-DlmesC2::384.

Example 3-3

Construction of Vector Devoid of Five ORFs of ZMO0390 to ZMO0394 and Carrying D-Lactate Dehydrogenase Gene A 3,280 bp DNA fragment (SEQ ID NO: 45) and a 3,008 bp DNA fragment (SEQ ID NO: 46) which were, respectively, positioned upstream of the 5' end and downstream of the 3' end of each of the five ORFs ZMO0390~ZMO0394 were amplified by PCR using a pair of forward (87F) and reverse primers (89R) in the same manner as in Example 1, with the exception that the extension was performed for 10 min.

```
Forward primer (390F)
                                        (SEQ ID NO: 47)
5-ATGATCCGATGGCTGGAAATAATGCGGATATG-3

Reverse primer (394R)
                                        (SEQ ID NO: 48)
5-TAGCGGTCTGAGGCTGTGCCTCCGATGTA-3
```

The PCR products thus obtained were treated with the restriction enzyme PmeI (NEB), and cloned to a pBluescript II vector (Stratagene) at the same restriction enzyme site to give a recombinant vector pBS-ZMO0390394.

Subsequently, regions of the pBluescript II vector which were positioned, respectively, upstream and downstream of each of the ORFs ZMO0390~ZMO0394 were selectively amplified by reverse-transcription PCR. The primers used in the reverse-transcription PCR (del 394F and del 390R) were shown as follows. PCR was performed in the same manner as in Example 1, with the exception that 10 min was given to the extension step.

```
Forward primer (del 394F)
                                        (SEQ ID NO: 49)
5-CATCCATTTTGGATATTATTTTTAAATTAATCC-3

Reverse primer (del 390R)
                                        (SEQ ID NO: 50)
5-CGGTAAGTGCCTTTCACCGCTTCCACGACAG-3
```

The resulting PCR products were treated with the restriction enzyme PmeI (NEB), ligated to the sp-DlmesC2 gene of Example 1 in the presence of T4 DNA ligase (NEB), and used to construct a recombinant vector pBS-Del 390::sp-DlmesC2::394.

Example 3-4

Construction of Vector Devoid of Four ORFs of ZMO1786 to ZMO1789 and Carrying D-Lactate Dehydrogenase Gene A 3,450 bp DNA fragment (SEQ ID NO: 51) and a 3,100 bp DNA fragment (SEQ ID NO: 52) which were, respectively, positioned upstream of the 5'end and downstream of the 3' end of each of the four ORFs ZMO1786 to ZMO1789 were amplified by PCR using a pair of forward (1786F) and reverse primers (1789R) in the same manner as in Example 1, with the exception that the extension was performed for 10 min.

```
Forward primer (1786F)
                                        (SEQ ID NO: 53)
5-ACCAAAGCCGAAAAAAGGTCATCAAAAATACC-3

Reverse primer (1789R)
                                        (SEQ ID NO: 54)
5-GTTCAATTGCCACGCTTGAGGCTTTTGAAAATGC-3
```

The PCR products thus obtained were treated with the restriction enzyme PmeI (NEB), and cloned to a pBluescript II vector (Stratagene) at the same restriction enzyme site to give a recombinant vector pBS-ZMO0390394.

Subsequently, regions of the pBluescript II vector which were positioned, respectively, upstream and downstream of each of the ORFs ZMO1786~ZMO1789 were selectively amplified by reverse-transcription PCR. The primers used in the reverse-transcription PCR (del 1789F and del 1786R) were shown as follows. PCR was performed in the same manner as in Example 1, with the exception that 10 min was given to the extension step.

```
Forward primer (del 1789F)
                                  (SEQ ID NO: 55)
5-TATCTCGCTTGCAATAAAACATATTTTCAGG-3

Reverse primer (del 1786R)
                                  (SEQ ID NO: 56)
5-AGATTTTATCCGACAAAATCAATTCTATAAG-3
```

The resulting PCR products were treated with the restriction enzyme PmeI (NEB), ligated to the sp-DlmesC2 gene of Example 1 in the presence of T4 DNA ligase (NEB), and used to construct a recombinant vector pBS-Del 1786::sp-DlmesC2::1789.

Example 3-5

Preparation of ZM Strain with D-Lactate Dehydrogenase Gene Substituted for a Gene or Region Irrelevant to the Lactate Metabolism Pathway The vectors constructed in Examples 3-1 to 3-4 were transformed into *Zymomonas mobilis* ZM4 (ATCC 31821) by electroporation to prepare mutant strains in which the sp-DlmesC2 gene was positioned instead of genes irrelevant to the lactate metabolism pathway, as follows.

After transformation of the pBS-Del 87::sp-DlmesC2::89 vector of Example 3-1 thereinto, *Zymomonas mobilis* ZM4 was cultured an RM medium (glucose 20 g/l; yeast extract (DIFCO), 10 g/l; $MgSO_4$, 1 g/l; $(NH_4)_2SO_4$, 1 g/l; $KH_2PO_4$, 2 g/l; agar, 15 g/l; pH 5.0) supplemented with spectinomycin to obtain a *Z. mobilis* ΔZMO8789::sp-DlmesC2 strain, named MG6118, in which the ORF genes ZMO0087~ZMO0089 were replaced by the sp-DlmesC2 gene.

Likewise, *Z. mobilis* ΔZMO381384::sp-DlmesC2 (MG6119), *Z. mobilis* ΔZMO390394::sp-DlmesC2 (MG6120), and *Z. mobilis* ΔZMO390394::sp-DlmesC2 (MG6121) were prepared into which the pBS-Del 381::sp-DlmesC2::384 vector, the pBS-Del 390::sp-DlmesC2::394 vector, and the pBS-Del 1786::sp-DlmesC2::1789 vector constructed respectively in Examples 3-1 to 3-4 were introduced to replace the corresponding genes with the sp-DlmesC2 gene.

EXAMPLE 4

Preparation of ZM Strain with D-Lactate Dehydrogenase Gene Substituted for Gene Relevant to Lactate Metabolism Pathway To examine relationship between the introduction of a D-lactate dehydrogenase gene and the regulation of the lactate metabolism pathway, and the effect of the introduced gene on lactic acid production, *Zymomonas mobilis* (ATCC 31821) was modified to be devoid of a gene or genes involved in the lactate metabolism pathway, and to have the DlmesC2 gene having a nucleotide sequence as set forth in SEQ ID NO: 1 introduced at the same site. Briefly, mutant *Zymomonas mobilis* strains which lacked gene(s) involved in the ethanol and lactic acid production of the core metabolism pathway and had the DlmesC2 gene instead of the deleted gene(s) were prepared in the same manner. In this connection, DNA regions, each more than 3000 bp in length, which were respectively positioned upstream and downstream of each gene relevant to the metabolism pathway were used in cloning through homogenous recombination

Example 4-1

Construction of Vector Lacking Lactate Dehydrogenase Gene (ZMO0256) and Carrying D-Lactate Dehydrogenase Gene (DlmesC2)

A 4,879 bp DNA fragment (SEQ ID NO: 57) and a 4,984 bp DNA fragment (SEQ ID NO: 58) which were, respectively, positioned upstream of the 5'end and downstream of the 3' end of the lactate dehydrogenase gene (ZMO0256) in the genome (AE008692) of *Zymomonas mobilis* ZM4 (ATCC 31821) was amplified by PCR using a pair of forward (ldhAF) and reverse primers (ldhAR) in the same manner as in Example 1, with the exception that the extension was performed for 10 min.

```
Forward primer (ldhAF)
                                  (SEQ ID NO: 59)
5-TGGCAGTCCTCCATCTAGATCGAAGGTGC-3

Reverse primer (ldhAR)
                                  (SEQ ID NO: 60)
5-GTGATCTGACGGTGAGCTCAGCATGCAGG-3
```

The PCR product thus obtained was treated with the restriction enzyme NotI (NEB), and cloned to a pBluescript II vector (Stratagene) at the same restriction enzyme site to give a recombinant vector pBS-ZMO0256.

Subsequently, regions of the pBluescript II vector which were positioned, respectively, upstream and downstream of the lactate dehydrogenase (ZMO0256) were selectively amplified by reverse-transcription PCR. The primers used in the reverse-transcription PCR (ldhA-PmeI-2F and ldhA-PmeI-2R) were shown as follows. PCR was performed in the same manner as in Example 1, with the exception that 10 min was given to the extension step.

```
Forward primer (1dhA-PmeI-2F)
                                         (SEQ ID NO: 61)
5-AACTAGTTTAAACAAGAGCGAAGAATAGCAAAGAAT-3

Reverse primer (1dhA-PmeI-2R)
                                         (SEQ ID NO: 62)
5-CTCTTGTTTAAACTAGTTATGGCATAGGCTATTACG-3
```

The resulting PCR product was treated with the restriction enzyme PmeI (NEB), ligated to the sp-DlmesC2 gene of Example 1 in the presence of T4 DNA ligase (NEB), and used to construct a recombinant vector pBS-Del ZMO256::sp-DlmesC2.

Example 4-2

Construction of Vector Lacking Lactate Dehydrogenase Gene (ZMO1237) and Carrying D-Lactate Dehydrogenase Gene (DlmesC2)

A 3,656 bp DNA fragment (SEQ ID NO: 63) and a 3,848 bp DNA fragment (SEQ ID NO: 64) which were, respectively, positioned upstream of the 5'end and downstream of the 3' end of the lactate dehydrogenase gene (ZMO1237) in the genome (AE008692) of *Zymomonas mobilis* ZM4 (ATCC 31821) was amplified by PCR using a pair of forward (Dldh-F) and reverse (Dldh-R) primers in the same manner as in Example 1, with the exception that the extension was performed for 10 min.

```
Forward primer (Dldh-F)
                                         (SEQ ID NO: 65)
5-TGTTTCAGGCGGCCGCTATTTTAAGTC-3

Reverse primer (Dldh-R)
                                         (SEQ ID NO: 66)
5-TCTTTATCGCGGCCGCATCAATCACAA-3
```

The PCR product thus obtained was treated with the restriction enzyme NotI (NEB), and cloned to a pBluescript II vector (Stratagene) at the same restriction enzyme site to give a recombinant vector pBS-ZMO1237.

Subsequently, regions of the pBluescript II vector which were positioned, respectively, upstream and downstream of the D-lactate dehydrogenase (ZMO1237) were selectively amplified by reverse-transcription PCR. The primers used in the reverse-transcription PCR (Del-DldF and Del-DldR) were shown as follows. PCR was performed in the same manner as in Example 1, with the exception that 10 min was given to the extension step.

```
Forward primer (Del-DldF)
                                         (SEQ ID NO: 67)
5-TTTCTTTTGCAGTTAACTGTCAGCCTGAA-3

Reverse primer (Del-DldR)
                                         (SEQ ID NO: 68)
5-TGATCCTGTATGGTTAACAATTGTTGCC-3
```

The resulting PCR product was treated with the restriction enzyme PmeI (NEB), ligated to the sp-DlmesC2 gene of Example 1 in the presence of T4 DNA ligase (NEB), and used to construct a recombinant vector pBS-Del ZMO1237::sp-DlmesC2.

Example 4-3

Construction of Vector Lacking Lactate Dehydrogenase Gene (ZMO1236) and Carrying D-Lactate Dehydrogenase Gene (DlmesC2)

A 3,844 bp DNA fragment (SEQ ID NO: 69) and a 3,861 bp DNA fragment (SEQ ID NO: 70) which were, respectively, positioned upstream of the 5'end and downstream of the 3' end of the lactate dehydrogenase gene (ZMO1236) in the genome (AE008692) of *Zymomonas mobilis* ZM4 (ATCC 31821) was amplified by PCR using a pair of forward (Adh1-F) and reverse (Adh1-R) primers in the same manner as in Example 1, with the exception that the extension was performed for 10 min.

```
Forward primer (Adh1-F)
                                         (SEQ ID NO: 71)
5-ACTCAATGGAACTGCAGCATGATCTGA-3

Reverse primer (Adh1-R)
                                         (SEQ ID NO: 72)
5-ACCAAAGTAACATCTGCAGTGTTGATAATGG-3
```

The PCR product thus obtained was treated with the restriction enzyme NotI (NEB), and cloned to a pBluescript II vector (Stratagene) at the same restriction enzyme site to give a recombinant vector pBS-ZMO1236.

Subsequently, regions of the pBluescript II vector which were positioned, respectively, upstream and downstream of the D-lactate dehydrogenase (ZMO1237) were selectively amplified by reverse-transcription PCR. The primers used in the reverse-transcription PCR (Del-Adh1F and Del-Adh1R) were shown as follows. PCR was performed in the same manner as in Example 1, with the exception that 10 min was given to the extension step.

```
Forward primer (Del-Adh1F)
                                         (SEQ ID NO: 73)
5-TTGCGAATATAGTTTAAACGATTGC-3

Reverse primer (Del-Adh1R)
                                         (SEQ ID NO: 74)
5-ACCAGAAAGGTTTAAACTTTGTCGTC-3
```

The resulting PCR product was treated with the restriction enzyme PmeI (NEB), ligated to the sp-DlmesC2 gene of Example 1 in the presence of T4 DNA ligase (NEB), and used to construct a recombinant vector pBS-Del ZMO1236::sp-DlmesC2.

Example 4-4

Construction of Vector Lacking Lactate Dehydrogenase Gene II (ZMO1596) and Carrying D-Lactate Dehydrogenase Gene (DlmesC2)

A 3,986 bp DNA fragment (SEQ ID NO: 75) and a 3,868 bp DNA fragment (SEQ ID NO: 76) which were, respectively, positioned upstream of the 5'end and downstream of the 3' end of the lactate dehydrogenase II gene (ZMO15967) in the genome (AE008692) of *Zymomonas mobilis* ZM4 (ATCC 31821) was amplified by PCR using a pair of forward (Adh2-F) and reverse (Adh2-R) primers in the same manner as in Example 1, with the exception that the extension was performed for 10 min.

```
Forward primer (Adh2-F)
                                    (SEQ ID NO: 77)
5-CATAACCGACCTGCAGAATAGCCA-3

Reverse primer (Adh2-R)
                                    (SEQ ID NO: 78)
5-TGTACCCACTGCAGAAGAATGATG-3
```

The PCR product thus obtained was treated with the restriction enzyme Nod (NEB), and cloned to a pBluescript II vector (Stratagene) at the same restriction enzyme site to give a recombinant vector pBS-ZMO1596.

Subsequently, regions of the pBluescript II vector which were positioned, respectively, upstream and downstream of the D-lactate dehydrogenase (ZMO1596) were selectively amplified by reverse-transcription PCR. The primers used in the reverse-transcription PCR (Del-Adh2F and Del-Adh2R) were shown as follows. PCR was performed in the same manner as in Example 1, with the exception that 10 min was given to the extension step.

```
Forward primer (Del-Adh2F)
                                    (SEQ ID NO: 79)
5-CCTACATACTAGTTTAAACCAACAAC-3

Reverse primer (Del-Adh2R)
                                    (SEQ ID NO: 80)
5-CTGTCTTGATGTTTAAACAAACAATGC-3
```

The resulting PCR product was treated with the restriction enzyme PmeI (NEB), ligated to the sp-DlmesC2 gene of Example 1 in the presence of T4 DNA ligase (NEB), and used to construct a recombinant vector pBS-Del ZMO1596:: sp-DlmesC2.

Example 4-5

Preparation of ZM Strain with D-Lactate Dehydrogenase Gene Substituted for Gene Involved in the Lactate Metabolism Pathway The vectors constructed in Examples 4-1 to 4-4 were transformed into *Zymomonas mobilis* ZM4 (ATCC 31821) by electroporation to prepare mutant strains in which the sp-DlmesC2 gene was positioned instead of genes involved in the lactate metabolism pathway, as follows.

After transformation of the pBS-Del ZMO256::sp-DlmesC2 vector of Example 4-1 thereinto, *Zymomonas mobilis* ZM4 was cultured an RM medium (glucose 20 g/l; yeast extract (DIFCO), 10 g/l; $MgSO_4$, 1 g/l; $(NH_4)_2SO_4$, 1 g/l; $KH_2PO_4$, 2 g/l; agar, 15 g/l; pH 5.0) supplemented with spectinomycin to obtain a *Z. mobilis* ΔZMO0256::sp-DlmesC2 strain, named MG6118, in which the lactate dehydrogenase gene (ZMO0256) was replaced by the sp-DlmesC2 gene.

The pBS-Del ZM01237::sp-DlmesC2 vector constructed in Example 4-2 was transformed into the *Zymomonas mobilis* strain (*Z. mobilis* ΔZMO0256::tet), prepared in Example 4-1, which lacked the lactate dehydrogenase gene (ZMO0256), followed by culturing the cells in an RM medium supplemented with spectinomycin to select a transformant which lacked both the lactate dehydrogenase (ZMO0256) gene and the D-lactate dehydrogenase (ZMO1237) gene and carried the DlmesC2 gene, named *Z. mobilis* ΔZMO0256::cm, ΔZMO1237::sp-DlmesC2 (MG6112 strain).

The pBS-Del ZM01236::sp-DlmesC2 vector constructed in example 4-3 was transformed into *Zymomonas mobilis* ZM4 which was then cultured in an RM medium supplemented with spectinomycin to select a transformant, named *Z. mobilis* ΔZMO1236::sp-DlmesC2 (MG6113 strain), in which the alcohol dehydrogenase I (ZMO1236) was replaced by the sp-DlmesC2 gene.

Finally, after transformation of the pBS-Del ZM01596:: sp-DlmesC2 vector constructed in Example 4-4 thereinto, *Zymomonas mobilis* ZM4 was cultured in an RM medium supplemented with spectinomycin to select a transformant, named *Z. mobilis* ΔZMO1596::sp-DlmesC2 (MG6114 strain), in which the alcohol dehydrogenase gene II (ZMO1596) gene was replaced by the sp-DlmesC2 gene.

EXPERIMENTAL EXAMPLE 1

Assay for D-Lactate Dehydrogenase Activity (Enzyme Activity)

The D-lactate dehydrogenase gene-introduced strains prepared in Examples 1 to 3 were assayed for enzyme activity to examine whether they were able to exert D-lactate dehydrogenase activity on the substrate pyruvate to produce D-lactic acid.

In this regard, wild-type *Zymomonas mobilis* ZM4 (ATCC 31821) was used as a control. Each of the wild-type ZM4 and the D-lactate dehydrogenase gene-introduced ZM strains (MG6106, MG6115, MG6116, MG6117, and MG6118) was cultured in a stationary manner to a log growth phase in an RM medium (glucose, 20 g/l; yeast extract (DIFCO), 10 g/l; $MgSO_4$, 1 g/l; $(NH_4)_2SO_4$, 1 g/l; $KH_2PO_4$, 2 g/l; pH 5.0) in an incubator, and harvested (12,000 rpm, 5 min, 4° C.). The cells were lyzed by sonication, and centrifuged (15,000 rpm, 10 min, 4° C.), and the supernatant was used to measure enzyme activity.

The activity of D-lactate dehydrogenase was measured using two different kits (Lactic acid assay kits) (Megazyme, Sigma) according to the instructions of the manufacturers', and the results are summarized in Table 1, below.

TABLE 1

| Comparison of Enzyme Activity among D-Lactate Dehydrogenase Gene-Introduced Strains | |
|---|---|
| strains | Specific D-lactate dehydrogenase activity (U/mg of protein) |
| *Zymomonas mobilis* ZM4 | 0.012 |
| *Zymomonas mobilis* MG6106 | 1.306 |
| *Zymomonas mobilis* MG6115 | 1.205 |
| *Zymomonas mobilis* MG6116 | 1.035 |
| *Zymomonas mobilis* MG6117 | 1.062 |
| *Zymomonas mobilis* MG6118 | 1.556 |

As seen in Table 1, the control wild-type ZM4 had an enzyme activity of 0.012 U/mg of protein while all the D-lactate dehydrogenase gene-introduced ZM strains (MG6106, MG6115, MG6116, MG6117 and MG6118) exhibited more than 1 U/mg of protein with a maximum of 1.556 U/mg of protein. Therefore, the D-lactate dehydrogenase gene-introduced transformants were far superior to the wild-type in terms of enzyme activity.

EXPERIMENTAL EXAMPLE 2

Assay for D-Lactic Acid/D-Lactate Production Capacity

Experimental Example 2-1: Method of assaying D-lactic acid/D-lactate production capacity An examination was made of the D-lactic acid/D-lactate production capacity of the D-lactate dehydrogenase gene-introduced strains prepared in Examples 1 to 4. In this context, each strain was grown in an RM medium (glucose, 20 g/l; yeast extract (DIFCO), 10 g/l; $MgSO_4$, 1 g/l; $(NH_4)_2SO_4$, 1 g/l; $KH_2PO_4$, 2 g/l) adjusted into a pH of 5.0 at 30° C. for 20 hrs, and after removal of the cells, the culture supernatant was measured for metabolite level using HPLC under the following condition. The wild-type *Zymomonas mobilis* ZM4 (ATCC 31821) used in Experimental Example 1 served as a control while *S. cerevisiae* (Dequin and Barre, Biotechnology (New York). 1994. February; 12(2):173-177) and/or *S. cerevisiae* OC2 (Ishida et al., J. Biosci. Bioeng. 2006. February; 101(2):172-177) was used for comparison.

<HPLC Condition>//

Experimental Example 2-2

Assay for D-Lactic Acid/D-Lactate Production Capacity of Strains Transformed with Various D-Lactate Dehydrogenase Genes The strains prepared in Examples 1 and 2 (MG6106, MG6115, MG6116, and MG6117) were assayed for D-lactic acid/D-lactate production capacity in the same manner as in Experimental Example 2-1. The results are summarized in Table 2, below. As can be seen in Table 2, not only MG6106 anchoring the DlmesC2 gene therein, but also MG6115, MG6116, and MG6117 into which a *Leuconostoc cremoris* ATCC 19254-derived, D-lactate dehydrogenase-encoding ldhD-ATCC19254 gene (996 bp) (SEQ ID NO: 3), a *Leuconostoc mesenteroides* LMG 18811-derived, D-lactate dehydrogenase-encoding ldhD1-LMG18811 gene (996 bp) (SEQ ID NO: 5), and a *Leuconostoc mesenteroides* NBRC 3426-derived, D-lactate dehydrogenase-encoding D-ldh-NBRC3426 gene (996 bp) (SEQ ID NO: 7), all having an identity of 95% or higher with DlmesC2, were introduced, respectively, were observed to produce lactic acid at high yield and efficiency.

In addition to the DlmesC2 gene, various D-lactate dehydrogenase genes having an identity of 95% or higher with the DlmesC2 gene were regarded effective for producing lactic acid.

TABLE 2

Lactic Acid Production Capacity of Strains Transformed with Various Relevant Genes

| | | | D-lactic acid | | | byproducts | | | |
|---|---|---|---|---|---|---|---|---|---|
| stain | Sequence identity of gene[b] | Glucose (g/L) | D-lactic acid (g/L) | Yield (%) | Productivity (g/L/h) | Succinic acid (g/L) | Ethanol Organic acid (g/L) | pH | Fermentation time (hour) |
| ZM4[a] | 20 | 20 | 0.1 | ~0.50 | 0.02 | <5.0 | >9.5 | 3.8 | 4 |
| MG6106[a] | 100 | 20 | 21 | >99.9 | 0.88 | <0.2 | <0.2 | 5.0 | 24 |
| MG6115[a] | 99 | 20 | 18.4 | ~92.0 | 0.76 | <0.2 | <0.2 | 5.0 | 24 |
| MG6116[a] | 96 | 20 | 15.2 | ~76.0 | 0.63 | <0.2 | <0.2 | 5.0 | 24 |
| MG6117[a] | 99 | 20 | 16.7 | ~83.5 | 0.7 | <0.2 | <0.2 | 5.0 | 24 |
| *S. cerevisiae*[c] | | 20 | ~4 | ~20 | | | | | |

[a] *Zymonas mobilis* strain
[b] Sequence identity of gene: the sequence identity of amino acid sequence (%)
[c] Dequin and Barre, 1994

Experimental Example 2-3

Assay for Influence on D-Lactic Acid/D-Lactate of the Introduction Site of D-Lactate Dehydrogenase Gene and the Regulation of the Lactate Metabolism Pathway A comparison was made of D-lactic acid/D-lactate production capacity among the strains prepared in Examples 3 and 4 in the same manner as in Experimental Example 2-1. The results are summarized in Table 3, below. As is understood from the data of Table 3, the transformants produced lactic acid at a yield of approximately 95.0% to 99.9% irrespective of the gene or region at which the DlmesC2 gene was introduced. Further, as shown in Table 4, the lactic acid production of each of the strains anchoring the D-lactate dehydrogenase gene DlmesC2 therein was neither dependent on nor promoted by other metabolism pathways.

TABLE 3

Comparison of Lactic Acid Production Capacity among Strains Transformed with D-Latate Dehydrogenase Gene at Gene or Regions Irrelevant to the Lactate Metabolism Pathway

| | | D-lactic acid | | | byproducts | | | |
|---|---|---|---|---|---|---|---|---|
| stain | Glucose (g/L) | D-lactic acid (g/L) | Yield (%) | Productivity (g/L/h) | Succinic acid (g/L) | Ethanol Organic acid (g/L) | pH | Fermentation time (hour) |
| ZM4[a)] | 20 | 0.1 | ~0.50 | 0.02 | <5.0 | >9.5 | 3.8 | 4 |
| MG6106[a)] | 20 | 21 | >99.9 | 0.88 | <0.2 | <0.2 | 5.0 | 24 |
| MG6118[a)] | 20 | 20 | ~99.9 | 0.95 | <0.2 | <0.2 | 5.0 | 24 |
| MG6119[a)] | 20 | 20 | ~99.9 | 0.95 | <0.2 | <0.2 | 5.0 | 24 |
| MG6120[a)] | 20 | 19 | ~95.0 | 0.79 | <0.2 | <0.2 | 5.0 | 24 |
| MG6121[a)] | | 20 | ~99.9 | 0.95 | <0.2 | <0.2 | 5.0 | 24 |
| *S. cerevisiae*[b)] | 20 | ~4 | ~20 | | | | 5.0 | |
| *S. cerevisiae* OC2[c)] | 100 | 61.5 | 61 | | | | 5.0 | 72 |

[a)]*Zymomonas mobilis* strain
[b)]Dequin and Barre, 1994
[c)]Ishia et al,, 2006

TABLE 4

| | | D-lactic acid | | | byproducts | | | |
|---|---|---|---|---|---|---|---|---|
| stain | Glucose (g/L) | D-lactic acid (g/L) | Yield (%) | Productivity (g/L/h) | Succinic acid (g/L) | Ethanol Organic acid (g/L) | pH | Fermentation time (hour) |
| ZM4[a)] | 20 | 0.1 | ~0.50 | 0.02 | <5.0 | >9.5 | 3.8 | 4 |
| MG6106[a)] | 20 | 21 | >99.9 | 0.88 | <0.2 | <0.2 | 5.0 | 24 |
| MG6111[a)] | 20 | 19.8 | ~99.9 | 0.95 | <0.2 | <0.2 | 5.0 | 24 |
| MG6112[a)] | 20 | 20.0 | ~99.9 | 0.95 | <0.2 | <0.2 | 5.0 | 24 |
| MG6113[a)] | 20 | 19 | ~95.0 | 0.79 | <0.2 | <0.2 | 5.0 | 24 |
| MG6114[a)] | | 20 | ~99.9 | 0.95 | <0.2 | <0.2 | 5.0 | 24 |
| *S. cerevisiae*[b)] | 20 | ~4 | ~20 | | | | 5.0 | |

[a)]*Zymomonas mobilis* strain
[b)]Dequin and Barre, 1994

As described above, the lactic acid production of the strains into which the D-lactate dehydrogenase gene was introduced were neither dependent on nor stimulated by either the gene or region at which the gene was introduced or the metabolism pathway. Accordingly, the lactic acid production was dependent utterly on the existence of the D-lactate dehydrogenase gene itself, but indifferent of the gene or region at which the lactate dehydrogenase gene was introduced or the metabolism pathway. In contrast, *S. cerevisiae* transformed with the D-lactate dehydrognase gene was not effective in producing D-lactic acid/lactate in a condition irrespective of the metabolism pathway or in the presence of the core produce metabolism pathway (e.g., ethanol production pathway), indicating that the lactic acid production of the *S. cerevisiae* transformed with the gene of interest is dependent on the regulation of the metabolism pathway.

Accordingly, the strains transformed with the D-lactate dehydrogenase gene which can effectively D-lactic acid/lactate independently of the regulation of the metabolism pathway were found to have far better lactic acid production capacity.

Experimental Example 2-4

D-Lactic Acid/D-Lactate Production Depending on pH Condition

MG6106 prepared in Example 1 was assayed for lactic acid production capacity depending on pH condition. Its D-lactic acid/D-lactate production capacity was measured in the same manner as in Experimental Example 2-1. For D-lactic acid/D-lactate production capacity under a pH uncontrolled condition, the strain was cultured at 30° C. for 20 hrs in RM broth which reached a final pH of 3.0 without adjusting the pH with a base, and the culture supernatant from which the cells were removed was used. The results are given in Table 5, below.

TABLE 5

| Lactic Acid Production Assay-pH 5.0, pH Unadjusted | | | | | | | | |
|---|---|---|---|---|---|---|---|---|
| | | D-lactic acid | | | byproducts | | | |
| stain | Glucose (g/L) | D-lactic acid (g/L) | Yield (%) | Productivity (g/L/h) | Succinic acid (g/L) | Ethanol Organic acid (g/L) | pH | Fermentation time (hour) |
| ZM4[a)] | 100 | 0.2 | <0.40 | — | <8.0 | >25 | 3.8 | 4 |
| MG6106-pH 5.0[a)] | 65 | 65.6 | >99.9 | 1.09 | <0.1 | <0.1 | 5.0 | 60 |
| MG6106-unadjusted pH[a)] | 62 | 61.8 | 99.7 | 1.03 | <0.1 | <0.1 | 3.0 (unadjusted) | 60 |
| *S. cerevisiae* OC2[b)] | 100 | 61.5 | 61 | | | | 5.0 | 72 |
| *S. cerevisiae* OC2-unadjusted pH[b)] | 100 | 54.2 | 53 | | | | 2.8 (unadjusted) | |

[a)]*Zymomonas mobilis* strain
[b)]Ishida et al, 2006

As can be seen in Table 5, the strains transformed with the D-lactate dehydrogenase gene were observed to produce D-lactic acid/D-lactate at a yield of as high as 99.9% and 99.7% at pH 5.0 and in a pH unadjusted condition (acidic condition), respectively. *S. cerevisiae* OC2 was previously reported to have good D-lactic acid production efficiency both at pH 5.0 and in a pH unadjusted condition. However, *S. cerevisiae* OC2 was observed to produce D-lactic acid/lactate at a yield of 61% and 53% at pH 5.0 and in a pH unadjusted condition, respectively. Thus, the strains transformed with the D-lactate dehydrogenase gene guaranteed significantly high production yields of D-lactic acid/lactate in any pH condition.

EXPERIMENTAL EXAMPLE 3

Optical Purity of D-Lactic Acid/D-Lactate Depending on pH

The D-lactic acid/D-lactate produced by the MG6106 strain prepared in Example 1 was measured for optical purity in various pH conditions. In this context, the strains were cultured at 30° C. for 20 hrs in RM broth (glucose, 20 g/l; yeast extract (DIFCO), 10 g/l; $MgSO_4$, 1 g/l; $(NH_4)_2SO_4$, 1 g/l; $KH_2PO_4$, 2 g/l) which was maintained at pH 5.0 by adding a base or reached a final pH of 3.0 without adjustment with a base. The culture media from which the cells were removed were subjected to HPLC (high performance liquid chromatography), and the purified D-lactic acid/D-lactate was analyzed for optical purity (%) or enantiomeric excess (ee value, %). The results are summarized in Table 6, below. As in Example 2, the wild-type *Zymomonas mobilis* ZM4 (ATCC 31821) used in Experimental Example 1 served as a control while *S. cerevisiae* OC2 (Ishida et al., J. Biosci. Bioeng. 2006. February; 101(2):172-177) was used for comparison.

<HPLC Condition>

HPLC system: Hitachi HPLC system (model D-7000)

Column: Chirex 3126 column (Phenomenex)(250 mm×4.6 mm)

Column Temperature: 25° C.

Flow rate: 1.5 ml/min

Mobile phase (solvent): 1 mM copper sulfate (CuSO4) solution

Detector: UV detector (Hitachi D-4200)(254 nm)

Standard reagents D(−)-lactic acid (L0625, Sigma), L(+)-lactic acid (L1750, Sigma), and DL-lactic acid (L1250, Sigma) were used to discriminate and separate the enantiomers D-lactic acid and L-lactic acid from each other, and optical purity (%) and enantiomeric excess (ee value %) were calculated according to the following Math Formulas 1 and 2, respectively.

Optical purity of D-lactic acid (%)= $D/D+L*100$ [Mathematical formula 1]

*ee* value (%)= $D+L/D-L*100$ [Mathematical formula 2]

TABLE 6

| Optical Purity Assay of Lactic Acid-pH 5.0, pH Unadjusted Condition | | | | | | | |
|---|---|---|---|---|---|---|---|
| stain | Glucose (g/L) | Lactic acid (g/L) | pH | Yield (%) | L-LA (g/L) | D-LA (g/L) | Optical Purity (D-LA %) |
| ZM4[a)] | 20 | 0.1 | 3.8 | <0.40 | ~0.07 | ~0.03 | >33.3 |
| MG6106-pH 5.0[a)] | 65 | 65.69 | 5.0 | >99.9 | 0.00 | 65.6 | >99.9 |
| MG6106-unadjusted pH[a)] | 62 | 61.8 | 3.0 (unadjusted) | 99.7 | 0.00 | 61.8 | >99.9 |
| *S. cerevisiae* OC2[b)] | 100 | 61.5 | 5.0 | 61 | | | >99.9 |

TABLE 6-continued

| Optical Purity Assay of Lactic Acid-pH 5.0, pH Unadjusted Condition | | | | | | | |
|---|---|---|---|---|---|---|---|
| stain | Glucose (g/L) | Lactic acid (g/L) | pH | Yield (%) | L-LA (g/L) | D-LA (g/L) | Optical Purity (D-LA %) |
| *S. cerevisiae* OC2-unadjusted pH[b)] | 100 | 54.2 | 2.8 (unadjusted) | 53 | | | >99.9 |

[a)]*Zymomonas mobilis* strain
[b)]Ishida et al, 2006

As can be seen in Table 6, the lactic acid produced by the control wild-type ZM4 was as low as approximately 33.3% in optical purity whereas the strains transformed with the D-lactate dehydrogenase gene produced lactic acid with an optical purity of 99.9%, which was the same level as that in *S. cerevisiae* OC2. As for *S. cerevisiae* OC2, however, its lactic acid productivity depended on the regulation of the lactate metabolism pathway as demonstrated in Experimental Example 2-3. In contrast, the strains transformed with the D-lactate dehydrogenase gene could produce lactic acid of very high optical purity at very high yield without regulating the lactate metabolism pathway and limiting the pH condition, which is very advantageous over the control wild-type ZM4 and *S. cerevisiae* OC2.

What is claimed is:

1. A *Zymomonas mobilis* transformant, comprising a gene encoding a D-lactate dehydrogenase derived from *Leuconostoc* sp, wherein the D-lactate dehydrogenase comprises the amino acid sequence of SEQ ID NO: 2.

2. The *Zymomonas mobilis* transformant of claim 1, wherein the gene encoding a D-lactate dehydrogenase comprises the nucleotide sequence of SEQ ID NO: 1.

3. The *Zymomonas mobilis* transformant of claim 1, wherein the *Zymomonas mobilis* transformant is deposited under accession No. KCTC 11803BP.

* * * * *

SEQUENCE LISTING

```
<160> NUMBER OF SEQ ID NOS: 80

<210> SEQ ID NO 1
<211> LENGTH: 996
<212> TYPE: DNA
<213> ORGANISM: Artificial Sequence
<220> FEATURE:
<223> OTHER INFORMATION: Nucleotide sequence of D-lactate dehydrogenase
      gene (DlmesC2) of Leuconostoc mesenteroides

<400> SEQUENCE: 1

atgaagattt ttgcttacgg cattcgtgat gatgaaaagc catcacttga agaatggaaa     60

gcggctaacc cagagattga agtggactac acacaagaat tattgacacc tgaaacagct    120

aagttggctg agggatcaga ttcagctgtt gtttatcaac aattggacta tacacgtgaa    180

acattgacag ctttagctaa cgttggtgtt actaacttgt cattgcgtaa cgttggtaca    240

gataacattg attttgatgc agcacgtgaa tttaacttta acatttcaaa tgttcctgtt    300

tattcaccaa atgctattgc agaacactca atgattcaat tatctcgttt gctacgtcgc    360

acgaaagcat tggatgccaa aattgctaag cacgacttgc gttgggcacc aacaattgga    420

cgtgaaatgc gtatgcaaac agttggtgtt attggtacag gtcatattgg ccgtgttgct    480

attaacattt tgaaaggctt tggggccaag gttattgctt atgacaagta cccaaatgct    540

gaattacaag cagaaggttt gtacgttgac acattagacg aattatatgc acaagctgat    600

gcaatttcat tgtatgttcc tggtgtacct gaaaaccatc atctaatcaa tgcagatgct    660

attgctaaga tgaaggatgg tgtggttatc atgaacgctg cgcgtggtaa tttgatggac    720

attgacgcta ttattgatgg tttgaattct ggtaagattt cagacttcgg tatggacgtt    780

tatgaaaatg aagttggctt gttcaatgaa gattggtctg gtaaagaatt cccagatgct    840

aagattgctg acttgattgc acgtgaaaat gtattggtta cgccacacac ggctttctat    900

acaactaaag ctgttctaga aatggttcac caatcatttg atgcagcagt tgctttcgcc    960

aagggtgaga agccagctat tgctgttgaa tattaa                              996


<210> SEQ ID NO 2
<211> LENGTH: 331
<212> TYPE: PRT
<213> ORGANISM: Artificial Sequence
<220> FEATURE:
```

-continued

<223> OTHER INFORMATION: Amino acid sequence of D-lactate dehydrogenase
      gene (DlmesC2) of Leuconostoc mesenteroides

<400> SEQUENCE: 2

```
Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Ala Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ala Arg
        275                 280                 285

Glu Asn Val Leu Val Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330
```

<210> SEQ ID NO 3
<211> LENGTH: 996
<212> TYPE: DNA
<213> ORGANISM: Artificial Sequence
<220> FEATURE:
<223> OTHER INFORMATION: Nucleotide sequence of D-lactate dehydrogenase
      gene (ldhD-ATCC19254) of Leuconostoc cremoris ATCC19254

<400> SEQUENCE: 3

-continued

```
atgaagattt ttgcttacgg cattcgtgat gatgaaaagc catcacttga agaatggaaa     60

gcggctaacc cagaggttga agtggactac acacaagaat tattgacacc tgaaacagct    120

aagttggctg agggatcaga ttcagctgtt gtttatcaac aattggacta tacacgtgaa    180

acattgacag ctttagctaa cgttggtgtt actaacttgt cattgcgtaa cgttggtaca    240

gataacattg attttgatgc agcacgtgaa tttaacttta acatttcaaa tgttcctgtt    300

tattcaccaa atgctattgc agaacactca atgattcaat tatctcgttt gctacgtcgc    360

acgaaagcat tggatgccaa aattgctaag cacgacttgc gttgggcacc aacaattgga    420

cgtgaaatgc gtatgcaaac agttggtgtt attggtacag gtcatattgg ccgtgttgct    480

attaacattt tgaaaggctt tggggccaag gttattgctt atgacaagta cccaaatgct    540

gaattacaag cagaaggttt gtacgttgac acattagacg aattatatgc acaagctgat    600

gcaatttcat tgtatgttcc tggtgtacct gaaaaccatc atctaatcaa tgcagatgct    660

attgctaaga tgaaggatgg tgtggttatc atgaacgctg cgcgtggtaa tttgatggac    720

attgacgcta ttattgatgg tttgaattct ggtaagattt cagacttcgg tatggacgtt    780

tatgaaaatg aagttggctt gttcaatgaa gattggtctg gtaaagaatt cccagatgct    840

aagattgctg acttgattgc acgcgaaaat gtattggtta cgccacacac ggctttctat    900

acaactaaag ctgttctaga aatggttcac caatcatttg atgcagcagt tgctttcgcc    960

aagggtgaga agccagctat tgctgttgaa tattaa                              996
```

```
<210> SEQ ID NO 4
<211> LENGTH: 331
<212> TYPE: PRT
<213> ORGANISM: Artificial Sequence
<220> FEATURE:
<223> OTHER INFORMATION: Amino acid sequence of D-lactate dehydrogenase
      gene (ldhD-ATCC19254) of Leuconostoc cremoris ATCC19254

<400> SEQUENCE: 4

Met Lys Ile Phe Ala Tyr Gly Ile Arg Asp Asp Glu Lys Pro Ser Leu
1               5                   10                  15

Glu Glu Trp Lys Ala Ala Asn Pro Glu Val Glu Val Asp Tyr Thr Gln
            20                  25                  30

Glu Leu Leu Thr Pro Glu Thr Ala Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
```

-continued

```
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ala Arg
        275                 280                 285

Glu Asn Val Leu Val Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330
```

<210> SEQ ID NO 5
<211> LENGTH: 996
<212> TYPE: DNA
<213> ORGANISM: Artificial Sequence
<220> FEATURE:
<223> OTHER INFORMATION: Nucleotide sequence of D-lactate dehydrogenase gene (ldhD1-LMG18811) of Leuconostoc mesenteroides LMG18811

<400> SEQUENCE: 5

```
atgaaaattt ttgcttacgg catacgtgac gacgaaaagc catcacttga agattggaag     60

tcagctcatc caaatattga ggttggctat acacaagaat tgttaacagc tgaaacagca    120

acgttggcta agggttcagt ttcagctgtg gtctatcaac aacttgatta tacacgtgaa    180

gctttgacag ctttggctga ggtgggcgtt actaacttgt cattaagaaa tgttggtact    240

gataatattg atttcgaagc agcaaaagaa tttaatttta acatctcaaa cgttccagta    300

tattcaccaa atgctattgc ggaacactca atgattcaat tatcacgctt attacgtcgt    360

acaaaagcac ttgatgcaaa gattgctaag cacgatctac gttgggcacc cacaattggt    420

cgcgaaatgc gcatgcaaac agttggtgtt attggcactg gtaacattgg tcgtgttgca    480

attaaaattt tacaaggctt tggcgcaaaa gtagttgcct acgacaaatt tccaaatgct    540

gaaattgcgg aacagggttt gtatgttgac tcattagatg aactatatgc acaagctgat    600

gcggtttcac tatacgtacc aggtgtacct gaaaatcacc acatgattga tgcagcagcc    660

atttcaaaga tgaaagatgg tgttgttatt atgaacgcat cacgtggtaa cctaatggat    720

atcgatgcta ttatcgatgg cttaaattct ggtaaaattt ctgattttgg tatggatgtt    780

tatgaagaag aagttggttt gttcaatgag gattggtcag gtaaagattt tcctgatgcc    840

aaaatcgctg atttgatttc acgtgagaat gttttggtta caccccacac ggctttttat    900

acaacgaaag ctgttcttga gatggttcat caatcaatgg atgctgctgt tgcttttgct    960

aacggtgaaa cacctgcaat cgctgttaaa tactga                              996
```

<210> SEQ ID NO 6
<211> LENGTH: 331
<212> TYPE: PRT
<213> ORGANISM: Artificial Sequence

```
<220> FEATURE:
<223> OTHER INFORMATION: Amino acid sequence of D-lactate dehydrogenase
      gene (ldhD1-LMG18811) of Leuconostoc mesenteroides LMG18811

<400> SEQUENCE: 6

Met Lys Ile Phe Ala Tyr Gly Ile Arg Asp Asp Glu Lys Pro Ser Leu
1               5                   10                  15

Glu Asp Trp Lys Ser Ala His Pro Asn Ile Glu Val Gly Tyr Thr Gln
            20                  25                  30

Glu Leu Leu Thr Ala Glu Thr Ala Thr Leu Ala Lys Gly Ser Val Ser
        35                  40                  45

Ala Val Val Tyr Gln Gln Leu Asp Tyr Thr Arg Glu Ala Leu Thr Ala
    50                  55                  60

Leu Ala Glu Val Gly Val Thr Asn Leu Ser Leu Arg Asn Val Gly Thr
65                  70                  75                  80

Asp Asn Ile Asp Phe Glu Ala Ala Lys Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
    130                 135                 140

Met Gln Thr Val Gly Val Ile Gly Thr Gly Asn Ile Gly Arg Val Ala
145                 150                 155                 160

Ile Lys Ile Leu Gln Gly Phe Gly Ala Lys Val Val Ala Tyr Asp Lys
                165                 170                 175

Phe Pro Asn Ala Glu Ile Ala Glu Gln Gly Leu Tyr Val Asp Ser Leu
            180                 185                 190

Asp Glu Leu Tyr Ala Gln Ala Asp Ala Val Ser Leu Tyr Val Pro Gly
        195                 200                 205

Val Pro Glu Asn His His Met Ile Asp Ala Ala Ala Ile Ser Lys Met
    210                 215                 220

Lys Asp Gly Val Val Ile Met Asn Ala Ser Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Glu Glu Val Gly Leu Phe Asn Glu Asp Trp
            260                 265                 270

Ser Gly Lys Asp Phe Pro Asp Ala Lys Ile Ala Asp Leu Ile Ser Arg
        275                 280                 285

Glu Asn Val Leu Val Thr Pro His Thr Ala Phe Tyr Thr Thr Lys Ala
    290                 295                 300

Val Leu Glu Met Val His Gln Ser Met Asp Ala Ala Val Ala Phe Ala
305                 310                 315                 320

Asn Gly Glu Thr Pro Ala Ile Ala Val Lys Tyr
                325                 330


<210> SEQ ID NO 7
<211> LENGTH: 996
<212> TYPE: DNA
<213> ORGANISM: Artificial Sequence
<220> FEATURE:
<223> OTHER INFORMATION: Nucleotide sequence of D-lactate dehydrogenase
      gene (D-ldh-NBRC3426) of Leuconostoc mesenteroides NBRC3426

<400> SEQUENCE: 7
```

-continued

```
atgaagattt ttgcttacgg cattcgtgat gatgaaaagc catcacttga agaatggaaa     60
gcggctaacc cagagattga agtggactac acacaagagc tattgacacc tgaaacagtt    120
aagttggctg agggatcaga ttcagctgtt gtttaccaac aactggacta tacacgtgaa    180
acattgacag ctttagctaa cgttggtgtt actaacttgt cattgcgtaa cgttggtaca    240
gataacattg attttgatgc agcacgtgaa tttaacttta acatttcaaa tgttcctgtt    300
tattcaccaa atgctattgc agaacactca atgattcaat tatctcgttt gctacgtcgc    360
acgaaagcat tggatgccaa aattgctaag cacgacttgc gctgggcacc aacaattgga    420
cgtgaaatgc gtatgcaaac agttggtgtt attggtacag gccatattgg ccgtgttgct    480
attaacattt tgaaaggctt tggggcaaag gttattgctt atgataagta cccaaatgct    540
gaattgcaag cagaaggttt gtacgttgac acattagacg aattatatgc acaagctgat    600
gcaatttcat tgtatgttcc tggtgtgcct gaaaaccatc atctaatcaa tgcagaggct    660
attgctaaga tgaaggatgg cgtggttatc atgaatgctg cgcgtggtaa tttgatggac    720
attgatgcta ttattgatgg tttgaattct ggtaagattt cagacttcgg tatggacgtt    780
tatgaaaatg aagttggctt gttcaatgaa gattggtctg gtaaagaatt cccagatgct    840
aagattgctg acttgatttc acgcgaaaat gtattggtta cgccacatac ggctttctat    900
acaactaaag ctgttctaga aatggttcac caatcatttg atgcagcagt tgctttcgcc    960
aaaggtgaga agccagctat tgctgttgaa tattaa                             996
```

```
<210> SEQ ID NO 8
<211> LENGTH: 331
<212> TYPE: PRT
<213> ORGANISM: Artificial Sequence
<220> FEATURE:
<223> OTHER INFORMATION: Amino acid sequence of D-lactate dehydrogenase
      gene (D-ldh-NBRC3426) of Leuconostoc mesenteroides NBRC3426

<400> SEQUENCE: 8

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Val Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175
```

-continued

```
Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Glu Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ser Arg
        275                 280                 285

Glu Asn Val Leu Val Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330


<210> SEQ ID NO 9
<211> LENGTH: 28
<212> TYPE: DNA
<213> ORGANISM: Artificial Sequence
<220> FEATURE:
<223> OTHER INFORMATION: DLmesC2F

<400> SEQUENCE: 9

tggaggatcc catggtaaag atttttgc                                          28


<210> SEQ ID NO 10
<211> LENGTH: 28
<212> TYPE: DNA
<213> ORGANISM: Artificial Sequence
<220> FEATURE:
<223> OTHER INFORMATION: DLmesC2R

<400> SEQUENCE: 10

tgtttgatta ttcctgcaga aacccctc                                          28


<210> SEQ ID NO 11
<211> LENGTH: 370
<212> TYPE: DNA
<213> ORGANISM: Artificial Sequence
<220> FEATURE:
<223> OTHER INFORMATION: promoter region of adhB, ZMO1596

<400> SEQUENCE: 11

ttcataattt gcataagtct tgatgtaaaa aatacatatt tagaaagaac aagcagcctt      60

gctcatcacc gctgtcgcga gtagaaaaat ctcggctttc agaaaataga ggtcgcttcg     120

ttaaacagac tataaatgtg ctggaataaa gcgaacccct tgatctgata aaactgatag     180

acatattgct tttgcgctgc ccgattgctg aaaatgcgta aaattggtga ttttactcgt     240

tttcaggaaa aactttgaga aaacgtctcg aaaacgggat taaaacgcaa aaacaataga     300

aagcgatttc tcgaaaatgg ttgttttcgg gttgttgctt taaactagta tgtagggtga     360

ggttatagct                                                            370
```

-continued

<210> SEQ ID NO 12
<211> LENGTH: 1142
<212> TYPE: DNA
<213> ORGANISM: Artificial Sequence
<220> FEATURE:
<223> OTHER INFORMATION: spectinomycin resistant gene

<400> SEQUENCE: 12
gaaccctttg gcaaaatcct gtatatcgtg cgaaaaagga tggatatacc gaaaaaatcg 60
ctataatgac cccgaagcag ggttatgcag cggaaaatgc agctcacggt aactgatgcc 120
gtatttgcag taccagcgta cggcccacag aatgatgtca cgctgaaaat gccggccttt 180
gaatgggttc atgtgcagct ccatcagcaa aaggggatga taagtttatc accaccgact 240
atttgcaaca gtgccgttga tcgtgctatg atcgactgat gtcatcagcg gtggagtgca 300
atgtcatgag ggaagcggtg atcgccgaag tatcgactca actatcagag gtagttggcg 360
tcatcgagcg ccatctcgaa ccgacgttgc tggccgtaca tttgtacggc tccgcagtgg 420
atggcggcct gaagccacac agtgatattg atttgctggt tacggtgacc gtaaggcttg 480
atgaaacaac gcggcgagct ttgatcaacg accttttgga aacttcggct tcccctggag 540
agagcgagat tctccgcgct gtagaagtca ccattgttgt gcacgacgac atcattccgt 600
ggcgttatcc agctaagcgc gaactgcaat ttggagaatg gcagcgcaat gacattcttg 660
caggtatctt cgagccagcc acgatcgaca ttgatctggc tatcttgctg acaaaagcaa 720
gagaacatag cgttgccttg gtaggtccag cggcggagga actctttgat ccggttcctg 780
aacaggatct atttgaggcg ctaaatgaaa ccttaacgct atggaactcg ccgcccgact 840
gggctggcga tgagcgaaat gtagtgctta cgttgtcccg catttggtac agcgcagtaa 900
ccggcaaaat cgcgccgaag gatgtcgctg ccgactgggc aatggagcgc ctgccggccc 960
agtatcagcc cgtcatactt gaagctagac aggcttatct tggacaagaa gaagatcgct 1020
tggcctcgcg cgcagatcag ttggaagaat ttgtccacta cgtgaaaggc gagatcacca 1080
aggtagtcgg caaatagatg ccgctcgcca gtcgattggc tgagctcatg aagttcctat 1140
tc 1142

<210> SEQ ID NO 13
<211> LENGTH: 1401
<212> TYPE: DNA
<213> ORGANISM: Artificial Sequence
<220> FEATURE:
<223> OTHER INFORMATION: Nucleotide sequence of ORF ZMO0263

<400> SEQUENCE: 13
atgcctaaaa aataccaatt tcttctctac ccccttcttc taaacagcgt ccttctgtca 60
gaattaaaag ctgacaagcc tctcgtttct ccaaaattga tcgaacttct caagcaacaa 120
acacctgaag cgttaaaaaa cggtattgaa attcgaccag gtggagatga gatgcaaaag 180
ggactgttag agggaaatga cctactcatc gacaaagccg ccagtgaact agaaggcaat 240
aaccccatca gaatattcgc tgatatagat aaattacgcg tcaaaggcga ttaccagaat 300
gccaataaat tgctggatat atgcggtaaa actttttttc aaaaacccga tgatcctaat 360
ccattgcccc ctgtcagtgg cgtaggtatg acatgccaac aaattttagc gggtaattac 420
ttcttagatg gtaatctcaa agattggggt aaaattcttc attttgttag aaatgtctat 480
tatcccccca tccgaaaaat ttcaggatta gagcagttct cgcttacaga tattgaaatg 540
gggaggttgt ccgtttctcc ggattctata cccccattca ccattacagg catagatcac 600

```
cagcaaagca ttccactaca atacaatgta cagataaagg aagatcatcg gcgttttgct    660

gaaaatgttc cttccgcaat ggtttcgttg aacgggaaag aggtgccttt cttcttagaa    720

accggtgccg ctattggcaa actacctaaa gcatggagtc attcccctca tgtccatatt    780

atcggacatc tcgatagatc aaccaatgct gcatctgaat tttttagtgg cgatctcggc    840

atcgttgatg agctcaaaat tggaaaagcc gttttaaaga acgttccctt ccttttttacc    900

gatgtcagcc aatcctatct gggactcatg attttacaaa aattaggtaa aatcaaaata    960

gataaacagc agatgacctt tggcaaggat atcaattgta attgtcagca agatatccat   1020

cttggcagcg cattaggggg cgatttccaa accctcaaat atccgattac gtggcaaggt   1080

aaaaccagtc tagtcgcaat tgaccttact gaggataaca gcgactttac gctatggaca   1140

tttaaaccag atttcacaaa agaagaacaa gaaaccacat tccagttccc cacaaaagaa   1200

aataacaaaa ctgttctaag tcaaggacgc gttgtaaaat ctgatttatc cattgatggg   1260

atcaactatg gagcaagaaa agagcttatt ataaaagata ctatccgaaa tccagctacc   1320

gttatgggct tgtttatcct caacaaagtc actctttatc tcgacttcat caatcacaaa   1380

gcctgcctta aatcgataca g                                              1401
```

<210> SEQ ID NO 14
<211> LENGTH: 1452
<212> TYPE: DNA
<213> ORGANISM: Artificial Sequence
<220> FEATURE:
<223> OTHER INFORMATION: Nucleotide sequence of ORF ZMO0264

<400> SEQUENCE: 14

```
ttgttttatc ggaagcctat catgcctaaa aaataccgat ttcttctcta tccccttctt     60

ctaaacagcg tcctcctgcc gccattgaaa gctgacaagc ctctcatttc tgaaaaatta    120

atcgaatttc taaggagtac aacagcagaa gaacaacaaa agggtgtaga gctcaaccct    180

gggaataaaa ggcttgtaga tgcccttttc gaaggagaca gtctccttat tgaaaagatt    240

gctaatgagc cagaaacaac aaatatcgtc aaaaaattta caaaaattga agcgttgctc    300

gtcaaaggca attatgaaga ggtcaatcga caattagcaa tatgtaaaaa aaccttcttc    360

caagacccaa acacgcctac tctacttcct ccgattaata atgtggtgat gacctgcgac    420

cagatttctg ctggtaatta ttttttggaa ggtaatcttc ccgcttgggg tgaaaaactc    480

aacaacatca acaatactta ttatcctgtc atccgaaaat tcaagggact agaaaatttt    540

tccctttcag caacaaaaat gggaagtcta actgtatttc cctctttaat acccgctttt    600

acggttaccg gaatagatca taaacaatca ttaccgataa aatatcaaga tataaataag    660

aacaaaacct ggaagattcc ttatattaac gcctctttaa atggcaaaaa gacgattctt    720

cttctggata cggaatccgc gattagtaaa ttacccatag atttaaaaga ttcgccccat    780

gtccatattg ttggacatat caactatgcg gataatggga ctgctgaaat ttttagtggc    840

gatctcggta ttgttgatga actcaaaatc ggaacagccg ttttaaaaaa cgttcccttt    900

ctctttacta ctacaaaaaa agcctatttg gggctgatgg ttcttcaaaa actgggtaaa    960

atcaaaataa ataaacagca gatgaccttt ggcaaaaata tcaactgtaa ctgtcaacag   1020

gacattcatc ttggaagtac atttgaagga gattaccaag cactcaaata tcccattaca   1080

tggcaaggta gaaccgatct agttgccata gatctttctg aagaaaacat cgattttaat   1140

ttactacagt tcaaatctga atttacgcca gaagaacaaa tattatttga aaaacaaaag   1200

aaaattattg atgaattcac cgacattact aaagataaaa taactgatcc agcctatatc   1260
```

gtggaatcag atttatctat tgatgggatc aattatagaa aaagacaaaa attagtcctc 1320
aaagatacta gacggcgtcc tacgatgact atcggagcat ccatcctcga aaaagctgac 1380
ctctatctcg actttatcaa ccacaaagcc tgtctcatgc cgaacaactc ggacacacag 1440
cctatgccac ag 1452

<210> SEQ ID NO 15
<211> LENGTH: 1428
<212> TYPE: DNA
<213> ORGANISM: Artificial Sequence
<220> FEATURE:
<223> OTHER INFORMATION: Nucleotide sequence of ORF ZMO0265

<400> SEQUENCE: 15
atgcctaaga aataccgatt tcttctttac tcctttcttc taaacagtgc tctcctgcca 60
gaattaaagg ctgaagagcc ccttgtttcg ccaaaactga ttgaacttct taagcaaaaa 120
acgcctgaag atttaaaaaa tggtatcgaa ttgcgatcag gcggtaatga aatgcgaaaa 180
gggttatctg agggagacga cctgcttatt gacaaagtcg ctaaagattt aagcaacagt 240
caccttgtcc aaaaatatgc tgaaataaac aagcttcgca ttaaaggtga ttatcaaaat 300
gccaataaat tacttgatat atgcgataag actttctttc aaaaacccga tgcccccaac 360
ccacttccgc ccatcagtgg cgtagggata atatgcaaac aaacattggt cggtaattac 420
tttttggatg gtaatctgaa agattggggt aaaagtctta attttgttag aaatgtctat 480
tatccaccca tccgaaaaat ttcaggatta gaagaattct ctcttacgga tgctgaaatg 540
ggtagattgt cggtctctcc gaattcgata cccccccttca aggttactgg gacagatcac 600
cagcaacgca ttcaactgca atttgatgtt gctatagacg aagaacatag gcggagtgct 660
actaactacg ttccccacat aaccgcatcc ctaaacggaa agaacattcc tttctttttg 720
gaaaccagtg ccgccattgg caaattgcca gaagaatggc gtcattctcc ccatgttcat 780
atcgtcgggc atctcgatcg ggcaaagaat ggagcttctg aattttttag tggtgacatt 840
ggcattgtcg atgaaatcaa aatcggaaaa gccgttttaa aaaacgttcc cttccttctt 900
accaatgtca atcaggctta tctgggactc atgattttac aaaaactggg taaaatcaaa 960
ataaataaac agcagatgac ctttggcaaa aatatcaact gtaactgtca acaggacatt 1020
catcttggca gcgcattggg gggcgatttc caatcggtcc aatatccaat tacatggcag 1080
gggtacacgc gtttagtggt agttgacttc actcaagatg ataccgttta taatttaaca 1140
acttataagt cagaatttac gccacaagag aaagaacaat ctttcgaaga aagaccagac 1200
cccaataaca aagaattgaa gttttcagtt tatttcaata aaggcaattt gttcgtggat 1260
aatatggatt atgggcaaaa aaaagaaata gttatagaag atagtcgatc tcgattagcc 1320
acaatcatcg gattatctat cctcgaaaaa gctgatctct atctcgactt catcaatcac 1380
aaagcctgcc tcaagccgaa caattcggac gctacgccta taccgcag 1428

<210> SEQ ID NO 16
<211> LENGTH: 1425
<212> TYPE: DNA
<213> ORGANISM: Artificial Sequence
<220> FEATURE:
<223> OTHER INFORMATION: Nucleotide sequence of ORF ZMO0266

<400> SEQUENCE: 16
atgtctaaga aataccgatt tcttctctat gcccttcttc taaacagctt ttgcctaccg 60

-continued ccattgaaag ctgacaagcc tcttatctct ccaaggctca tcgaacttct caagcaacaa 120
acacctgaaa cgttaaaaaa cggtattgaa attcgactgg gtggcgatga aatacaagaa 180
ggggtattgg agggcgacag ccttctcatc gacaaagcca tcaatgcgct ggaaagcaat 240
aatcttgcca gccaatatgc tgaaataaac aagctccgca tcaaaggaga ctatcaaagc 300
gccaataaat tacttgatat ctgtgataag actttctttc aaaaaccaga cacctcagct 360
tcgttaccgc ctatcaatgc cataggcatg gtatgcaaac agattttagc cggtaattat 420
tttctggacg gtaatctcaa agattggggt aaaagcctcg attttattaa aaatatctat 480
tacccacccg ttcgaaaaat ctcaggatta caacaattct cccttgcgga tgttaagatg 540
ggagggctat ctgtctcccc gaacccaata caaccctta ctattacaga catagagtac 600
caacaaagca ttccactaca gtatcaaatt cctataaaag aaaactttag gcgtaatgcg 660
gaacatgtcc cttatgtaat agcctcccta aacgagaaag aagttccttt ctttttggaa 720
accagcgcag ctattggcaa attacccaaa gcatggagcc attcccctca tgtccatatc 780
gtcggacata ttgagagagc aaccaatgct gcatctgaat tttatagcgg tgatctcggc 840
atcgttgatg agctcaaaat tgggaaggct gttttaaaaa acgttccctt ccttttcacc 900
aatgtcagcc aagcctatct gggactcatg attttacaaa agctcggtaa aatcaagata 960
gataaacagc agatgatctt tggcaaggat atcaattgca attgtcaaca agatatccac 1020
cttggcagcg cgttagcggg cgacttccaa gcccttaaat atccgattac ttggcaaggc 1080
aaaactaatt tagttgccgt agactttact caagataata ccatattcaa cttattaacc 1140
tttaagcccc aatttacagc tgaagaaaaa aaacaatctt tcgaagaaga tgtgaattca 1200
aataaaaaaa cgattaaaat tgtcggttat ttgaataacg aaaatttatt tattgatgga 1260
atagaccatg gaaaaataaa ggcacttgcc gaagaagata atagacgcaa gccagtaata 1320
attataagta catctatcct agacaaaggc agtcttcatc tcgacttcat caatcataaa 1380
gcctgtctta aaccaaatat ttcggacaca cagcctatgc cgcag 1425

<210> SEQ ID NO 17
<211> LENGTH: 1446
<212> TYPE: DNA
<213> ORGANISM: Artificial Sequence
<220> FEATURE:
<223> OTHER INFORMATION: Nucleotide sequence of ORF ZMO0267

<400> SEQUENCE: 17
ttgttttatc gaaagccttt tatgttcaaa aaataccgat ctcttctcta ccccccttctt 60 ctaaacagcg ttctcctgcc acaattaaag gctgacaagc ctcttatttc tccaaggctc 120
atcgaacttc tcaagcaaca aacacctgaa acgttaaaaa atggtattga aattcgaccg 180
ggtgacgaag aaatgcaaag gggagtatta gagggagatg acctactcat cgacaaagcc 240
gccaatgcac taaaaggcaa taatctcgtc agccaatatg ctaaaataga taaattacgc 300
gtcaaaggcg actatcaaaa cgccaataaa ctgctggata tctgcggtaa aactttttttt 360 caaaaacccg atgatcctaa tccattgccc cctgtcagtg gcgtaggtat gacatgccaa 420
caaattttag cgggtaatta cttcttagat ggtaatctca aagattgggg taaaattctt 480
cattttgtta gaaatgtcta ttatcccccc atccgaaaaa tttcaggatt agagcagttc 540
tcgcttacag atattgaaat ggggaggttg tccgtttctc cggattctat acccctattc 600
accattacag gcatagatca ccagcaaagc attccactac aatacaatgt acagataaag 660
gaagatcatc ggcgttttgc tgaaaatgtt ccttccgcaa tgatttcgtt gaataggaaa 720
gaggtgcctt tctttttaga aaccggtgcc gctattggaa aactacccaa agcatggagt 780
cattcccctc atgtccatat tatcggacat ctcgatagat caaccaatgc tgcatctgaa 840 tttttagtg gcgatctcgg catcgttgat gagctcaaaa ttggaaaagc tgttttaaag 900
aacgttccct tcctttttac cgatgtcagc caagcctatc tggggctcat gattttacaa 960
aaattaggta aaatcaaaat agataaacag caaatgacct ttggcaagga tatcaattgt 1020
aattgtcagc aagatatcca tcttggcagc gcattggggg gcgatttcca aaccctcaaa 1080
tacccaatta cgtggcaagg taaaaccagt ctagtcgcaa ttgaccttac tgaggataat 1140
agcgacttta cgctatggac atttaaacca gatttcacaa aagaagaaca agaaaccaca 1200
ttccaattcc ccacaaaaga aaataacaaa actgttctaa gtcaagggcg cattgtaaaa 1260
tctgacttat ccattgatgg gatcaattat ggagtaagag aagagtttat tgcaaaagat 1320
actatccaag atccagctac cattatgggc ttgtttatcc tcaacaaagt cactctctat 1380
ctcgacttca tcaatcacaa ggcctgcctc aagccgaaca attcggatgc tacgcctata 1440
tcgcag 1446

<210> SEQ ID NO 18
<211> LENGTH: 1422
<212> TYPE: DNA
<213> ORGANISM: Artificial Sequence
<220> FEATURE:
<223> OTHER INFORMATION: Nucleotide sequence of ORF ZMO0268

<400> SEQUENCE: 18
atgcctaaga aataccgatt ttttctctac ccccttcttc taaacagctt tttcctgccg 60
ccattgaaag caacaaagag cctcccctct tccaaactgg ttgattttct aaaacagcaa 120
agccctcaaa ctttaaagga agggctaaag gtagcccccg gtggcgatga aagcacttta 180 gcccttacg aaggagatag ccttcatctc caaaaaatga tcgatgatcc caagcgcacc 240
agctttgaaa aaaaatttat aaatacagac ttactaagaa ccaaaggcga cttcaaagaa 300
gcggataggc agctcgagat ttgccataaa acctatttta tggagggaag cgggatacat 360
ctttcgccta taaatctggg cgcaatgatc tgtgatcaaa ttttggcagg aaattatttt 420
cttgaaggca atcttgctgc ttggggcaaa aaaattgatg acatcaaaaa tacttactac 480
cctccgatcc gaaaatttgt aggattagag caattttctc ttttcgatat taaaatgggt 540
agcctgtcag ttgccccaaa ttcaataccc cccttcaccg ttaccggaat agatcagcag 600
caaacactgc cactacaatc tcagaaactt acccaagaag gctataggcg cagcacttgg 660
aatgtccctt atttaacagc gtctttaaac ggaaccgatt tctcgttttt cttaggaaca 720
gataccgcaa ttagtttctt acccaaagcc ttaagccatt cgtctcacgt ccatatcgtc 780
ggacatattg aaatagcgac caatggacgt ggcgaagcct ataacggcga tcttggtatt 840
gttgatgagc taaaaatcgg gacgacggtt ttaaaaaatg tcccgttcct gtttacaaat 900
acagatgaag cttctcttgg cctgatggtt cttcaaaaat taggcaaaat aaaaataaat 960
cgacaacatt tcactttcgg aaaagatatt gactgtcact gccagaaaga cattcaactc 1020
ggcagcatat ttgacggccg tttttatgcc ctaagatatc cgatcacatg gcaaggaaag 1080
accgagatgg ctgctattga tcttagccag agcgatgccc gttttagctt tatgctcttc 1140
caacctgatt ttacccctga agaagaaaaa caatcttttg aaattagtaa agaaattgac 1200
ggaacgaaag taaccgcttc tatttattta aaagatggca atctttccat tgatggcatt 1260
gactacggta aaagacaaaa atctgtacaa aaagataaat tacgcatatt ttctaaagtc 1320
atgacaatta caattcttga aaaagctgac ctctatctcg acttcatcaa tcacaaagcc 1380
tgcctcaagc cgaacaattc ggacgctacg cctataccgc ag 1422

<210> SEQ ID NO 19
<211> LENGTH: 1419
<212> TYPE: DNA
<213> ORGANISM: Artificial Sequence
<220> FEATURE:
<223> OTHER INFORMATION: Nucleotide sequence of ORF ZMO0269

<400> SEQUENCE: 19
atgcctaaaa aatacagatt tcttctctac ccccttcttc taaacagtct tgtcctgcca 60
cccttaaaag caacaaagag ccttccctct cccagactag tcgatttact taaacagcaa 120
tcgcctcagg cgctacagga agggcttaaa ctatcgcctg gcggagatga atccgcagac 180
gctctttttg aaggtaatac ccttcgtctc cagagaatga ctggcgattc tagaatagaa 240
aactttgcca agaaatttgc cagtatagaa gccttgcgga taaaaggtga cttcgaagag 300
gcgaataagc agctttccat ctgtcataaa actttttta gagaagctgg cgaaccgccc 360
atttctccca tcaatctttc tgcaatggtc tgtgaccaac ttttggcagg aaattacttt 420
cttgaaggca atcttgccgc ttggggtaaa gaaattgatg gcatcaaaaa cacctattac 480
cccgctgtcc gaaaatttgc tggcctcgaa caattttccc ttttcgatat taaaatgggt 540
aacctgtcag ttgccccaaa ttcaataccc cccttcaccg ttaccggaat aaaccgccag 600
caaacattgc cactagaata tcgagaacct acggctaaag actgttgccg cacgttgaac 660
agcccttctc tcacagcctc tttaaacaag aaagatttac ctttcttcct agaaaccgat 720
acagccattg gcaaactacc caaagaatta agccgatcgc ctcatattca tattgttgga 780
catatagaga tagcaggcaa tggacgtggg gaggctttta atggcgacct tggcgttgtc 840
gatgaactca agatcgggga tgctgttcta aaaaatgttc cttttctctt cacgaataca 900
aaagaagcct ctcttggtct gatggttttc caaaaattag ggaaaatcaa aatagaccgg 960
caacatttca ctttcggaaa agatattgac tgccactgcc agcgagatat caagctaggt 1020
agcagcttta gcggtagcta ccacatgcta agatatccga tcacatggca aggcaacacc 1080
gaactggcgg ctattgatct tagccaaact gatgcgcgct ttagcctcat gactttccag 1140
cctaatttca cgccagaaga agaaaaacaa tcttttgaaa ttaacggcga gattgagggc 1200
gaaaaaataa ctgcccgcgc ctatttagaa gaaggcaatc tttctatcga cggtatcgac 1260
tatggtaaaa aacaaaaatt cgtagaaaaa gctagctcgc gcgtcccttc taagctcgta 1320
actattacaa tcctagataa agcaagcctc tatctcgact ttattaatca caaagcctgc 1380
ctcaagccga acaattcgga cgaacagccc ataccgcag 1419

<210> SEQ ID NO 20
<211> LENGTH: 1479
<212> TYPE: DNA
<213> ORGANISM: Artificial Sequence
<220> FEATURE:
<223> OTHER INFORMATION: Nucleotide sequence of ORF ZMO0270

<400> SEQUENCE: 20
atgtaccttt ctagaatgca gcatgaatgc ttcattgctc taaaaacgga aatatttatg 60
ctaaaaaaat atctatttct tactctattt cttttttctg aacttttagc cttttctaaa 120
ggcaaagcag cagagagtct tccctcttcc aaactggttg attttctaaa acagcaaagc 180
cctcaaactt taaaggaagg gctaaaggta gcccccggtg gcgatgaaag cactttagcc 240
ctttacgaag gagatagcct tcatctccaa aaaatgatcg atgatcccaa gcgcaccagc 300
tttgaaaaaa aatttataaa tacagactta ctaagaacca aaggcgactt caaagaagcg 360
gatagacagc tcaagatttg ccataaaacc tatttcatgg agggcagcgg gatacatctt 420
tcgcctataa atctgggtgc catgatctgt gatcagctct tggcgggaaa ttacttcctc 480
gaaggcaatc ttgctgcatg gggtaaagaa attgatgaca tcaaaaacac ctactaccct 540
ccgatccgaa aatttgcagg attagagcaa ttttctcttt tcgatattaa aatgggtagc 600
ctgtcagttg ccccaaattc aatacccccc ttcaccgtta ccggaataga tcagcagcaa 660
acactgccgc tacaatctca gaaacttacc caagaaggca ataaaagtat tacttggaat 720
gtcccttatt taacagcgtc tttaaacgga accgatttct cattttctt aggaacagat 780 accgcgatta gtttcttacc caaagcccta agccattcgc ctcatgtcca tatcgtcgga 840
catattgaaa tagcgaccaa tggacgtggc gaagcctata atggcgatct tggtattgtt 900
gatgagctaa aaatcgggac ggcgattcta aaaaatgtcc cgttcctgtt tacaaataca 960
gatgaagcgt cccttagcct gatggttctt caaaaattag gcaaaataaa aatagatcgg 1020
caatatttca ctttcggaaa agatattgat tgtcactgcc agaaagacat ccaacttggc 1080
agcatatttg acggccgttt tcatgcttta agatatccaa tcacatggca aggaaagacc 1140
gagatggctg ccattaatct tagactcact gatgcccatc ttagttttat ggtcttccaa 1200
cctgacttca cccccgaaga ggaaaaacaa tcttttgaaa tggatcgcga aataaatgga 1260
aagaaaataa tttcttctat ttatttaacg gatggtaatc tttccattga tggcatcgac 1320
tacggcaaaa gactaaaatc tgtagaaaaa gacgaattac atatcccggc taaagttata 1380
ggcgtgtcga tcctagacaa aggcagcctc tatctcgact tcatcaatca caaggcctgt 1440
cttaaaccta atacttcgga cactacgcct atgccgcag 1479

<210> SEQ ID NO 21
<211> LENGTH: 4468
<212> TYPE: DNA
<213> ORGANISM: Artificial Sequence
<220> FEATURE:
<223> OTHER INFORMATION: Nucleotide sequence of upstream of ORF ZMO0263 - ZMO0270

<400> SEQUENCE: 21
ggaatcagga aagtctagcc gatcatctag aacatcaagc cagattatgc ctaacgggtg 60
aaaagctggc gattgcctgt catctgatcg acctgattga cgaagccgga tatctgaccg 120
agcctttatc ttccatcgcc tcgcatctta atattacaga agacgaaacg ttggaggttt 180
taaaggtcat tcagggcttt gacccgaccg gtgttggcgc tcgcaatctg gcagaatgtc 240
tgatgcttca agcggaagaa gccgacaggc ttgatccggc gatgcgaaaa ctgattacca 300
atctcgaatg gttgtcacgc ggagcattgc cccgtttaaa aaagctctgt caggtcgatg 360
acgaagactt cgccgacatg attcaggaat tacgaaatta caaccctaaa ccggggctaa 420
aatttggttc cgcaccgatc cagtcggtta caccggatat ttatattaaa cggatgaaag 480
acggctgggc gatcgaactc aataatgcca cacttccgaa attgctggtc aatcgtgctt 540
attattccga attaaaagcc cagaaaaccg acaaagccga acaaaaaagc tggctagatg 600
aaaaattggc gagcgccaac tggctggtaa gggcattgga tcaacgcgcc cgcacgatca 660
tcaaggtaac agaagccatt gtccaatatc aggaaggctt ttttctaaaa ggtatcgaac 720

-continued

```
agctcaaacc gctgacgcta cggcaggtag ccgaaaccat caacatgcat gaatcaacgg    780
tcagtcgggt taccaacaac aaatattttt cctgcgaaca gggaatattc gaattaaaat    840
atctcttctc cagcgggata caatccagcg gttccgaaga aggtgctgcg gccgaagccg    900
ttaaaagcca tattgcccgc ttcatcgctc aagaaggcgc agaaatccta tccgatgaca    960
agctggttga acttctaaaa gccaaaggct tcgccatcgc tcgccgaaca gtcgccaaat   1020
atcgagaagc tatcggccta ggctcctcag tgcaacgccg ccgccaaaaa gcgatcagcg   1080
cttcacaaaa agcctaacct gcaaaaaagc ctgcctcctt ttttaggaaa caggcttttt   1140
caaaggataa tgtcaaaaga caattccaag atcaggcaaa agccgctttc agcttatcaa   1200
ccagatcgag tttttcccac gggaagaaat caccatcggc tttacgaccg aaatgaccat   1260
aagcggcaga aggcttatag atcggcttgt tcaacttcag atgggtgcga atacccttcg   1320
gtgtcaaacg gatcagcttc ggcaagactt cttcaatctt ggcttcatca accgtgccgg   1380
tgccatgggt atcgacataa agcgacaaag gttcagaaac accaatggca taagaaagct   1440
ggatcgtcac tttcttggcc aaaccggcgg ccacgatgtt tttggcaaga tagcgggcaa   1500
cataagcggc agaacgatcg accttggtcg gatctttacc ggagaaagca ccaccaccat   1560
gaggcgctgc accgccatag gtatcaacga taatcttacg acccgttaaa ccggcatcac   1620
catcagggcc cccgatttca aacaagccgg tcggattaac gaaaatggct ttgtcatccg   1680
gcatccagcc tttaggcaga acatcttcat aaaccgattt gacatagtcg cgcagcttag   1740
cctgaccttc tttcgagctc aaagctggac tatgctgggt ggacagaacc aaagcagaag   1800
ctctgaccgg cacaccattt tcataaacca aagtcacctg acttttggca tcaggttcca   1860
gaaaatcgac tttttctgg tgacggtctt cagccagacg ttccagaata cgatgggcat    1920
aataaagggt cgctggcata tagtcaggcg tttcatcggt agcaaaaccg aacataatac   1980
cctgatcgcc cgcgccttcg tctttatctt caccggcatc gacaccttgg gcgatatcgg   2040
cagactgcgc atggagatgg ttagcgaatt cagccgttct ccaatcaaat ccggtctgct   2100
cgtaaccaat ttcacgtacg gtttcacgaa ccgtcttttc gatttcttct tcactgaccg   2160
gaacagccga acggacttca ccgccgataa tgatgcgctg tgtggtaacc agcgtttcac   2220
aggcgacgcg ggcttccggg tcacgggaaa gatacaaatc gacgatggca tcagaaattt   2280
ggtcagcaac cttatcggga tggccttcgg acacgctctc ggacgtaaac aggtagttgc   2340
tacgcataga aaaaggattt tccttatctg ttaaacctaa aaatgaagct ggcctgacag   2400
tttcccgatc agaaagagga aaaaataaac atctcgccct ttatggcaga tttttcttcc   2460
ccaaagccaa tccccatcta aaagtgacac gctatagaaa gatagaatat aaagatataa   2520
atctttcctt atatcaagac tagcgtaact taatacgccc aaacagggca atgagcaaca   2580
gagccgtggc aaaaagcaca ctaatcaggt tgccgtagcg ggcaaaaaag gtcggttgca   2640
acgctttcgg catcaccgct aaaagccgtc cttcggtatt ttcaggcaaa aattgcagga   2700
tacgcccttc tgcatcaatc accgcagaaa taccggtaga agtggctcgc gcgataggca   2760
gcccctcttc aatcgcccgc aatcgcgctt gtgccaaatg ttggggcggg cccgatcgac   2820
caaaccagct atcattggac aaattgaaaa tgaaatcggg gcgatgggtg cgatcaacta   2880
ctcgaccgga aaaaacgatt tcataacaaa tctgaatccc gaccagacca aaaggcacca   2940
gatcaagact ttcaggctgc gccccttcgg tgaattctat atcaccagcg accaaccgcc   3000
ctaatccgac ataggccgcc catttccgaa aaggcatata ttccccaaac ggcaccagat   3060
```

-continued gggctttgtc atagcggtct aaaatatcgc ccttggcatc aaggacaaat aaactattcc 3120
gaaccgaagc gatatgaccg gaattatcgg ggatcaaagc atcgcccccc gtcaacaaca 3180
gatcattttt gcccaataaa cggctcaaag ccgcccgtgc caaaggctct tcttcaagat 3240
agctttgaac cgcatcttcc ggccataaaa tcaggcgggg atgatgggga tcacccttcc 3300
ctgacaattt ctcgaaaata gcatcatgac gagatttata acggagatcg tatttttcat 3360
cctgcgggat attcggctgg acaatcacca catgagcagg cggtcgctcg gctttttgcc 3420
aatggatgtc atgaccatcg accaacgccc atcctaaaaa aggtaaagcc atccagaacg 3480
ccggaaggag cgaccggata gcctgcctcg cctgtctttt ctctatggct aacttgattc 3540
cgtcataaca agataatcct ataccggcgg caataaccac aagagccgac aaaccgtaac 3600
tcccgatcca tcgggcgata tgcgctatgg gcaggatatt cagccagatt gcccctaatg 3660
gactccatgg gaatccagta aaaacccatg attttatcca ttcgccccat gtcaaacatc 3720
ccgccaaggc cagcgtcaaa cgccaaagcg gtatttgcga caaagatata ttgaaaacag 3780
gcacagacca aaaagcagca gacccagcaa aaaaacggct tttcatcgtc ccttcacgcg 3840
ctaccgccgc gtcattctca acaggaaaaa gacgggaagg aatagcatcg atatcctcgg 3900
aatccgcacc atccccaatc ccatcagacg actgaaaaga atccactctt ttttcgcctc 3960
gccggaaaga aagacataag aaacgaaggg gcaaagtaaa aagagaaata taacaggcca 4020
aataacagga taataaaggt accgcgaccc aacccaacca tgacggcatc gcagcctgat 4080
gggtaaaaga agtcgcaatc cagtccagcc ctaaccagaa aaagccgaaa gcaaagagcc 4140
aactaagggc aaaaatctgc caagtctttt gggtttgtcg caataaggcc agccatccag 4200
ccacagccac aagactgcat ccccaaagat tataaggctg taatcccaag gccgcgacca 4260
atccggccag aaatgcaaaa atccaagtca caaaattggc tatctcaata gaataagaaa 4320
aaggcaagcc agttcagcca cccatcacca catgaaccaa tatctcaaat aaaaatgtta 4380
tttcatataa taattgttgg ataaaaacag atacaccact ccatatcact tttattgatg 4440
aatggagtat aaaattggac aacaactc 4468

<210> SEQ ID NO 22
<211> LENGTH: 4935
<212> TYPE: DNA
<213> ORGANISM: Artificial Sequence
<220> FEATURE:
<223> OTHER INFORMATION: Nucleotide sequence of downstream of ORF
ZMO0263 - ZMO0270

<400> SEQUENCE: 22
ataagccttt tacccatctt gtccgacgcg caaagcggca ccgatgacaa aaggcgcgac 60
agcgagcaaa aacaacgaac aagccgccaa taataggaag gccccaggct gatgaccatc 120
aacagccccc gcgccaaata taaggagcgg cacggccaaa ggcaataaaa gtaaagcagc 180
caacccactt ccggacttta tccttgccgt caaagcggca atcataaccc ccaaagaggc 240
cagtccagga gtagccaata aaaatccggc ttccaatttc cagaaaacag accaatccaa 300
agatagcaaa gccgaggcgg gtaacaacgc caccattaaa gggacagcaa aactcaccca 360
atgggcgata atacgcgcca cagctatcca ttcttcgcta atcccgcgca ccgcataatg 420
atcgaaaaag ccattttcga catcgggaat aatcaaacgg tcaatgggta acaaagaagc 480
caacagagct gcaacccata atattccgct accagtacgc gataaaatta tagcgtcact 540
gcccaccgcg aaagggaata gaacggcaac caataaaaaa aacaagacag gtagaaatac 600

-continued

```
ccctgccccg atcaaaatcg agcaatcccg acgaattaac aaaacaagcc ggatcaagag    660
aaatgacttt catccaaaag gtcaaagaaa cctgatgact ggccagaatt cgctacgaaa    720
ttttctaaag acaaggtttt ataatcagcc atatcaagcc cttgatgact aacagccaaa    780
ataatcccgc ccttttggcg atggtgctct atcatttcga tcaaagccct aacagaagcc    840
gcatcaagcc cgtttgccgg ttcatccaac aaccagatag cagcctggct tgccaacaaa    900
cgcgccaaca cagctctttt acgctgccca gtggagagca aacggacagg tgaatccgcc    960
aatatatcaa gagccatcac cgccattgct tctttttcag cgcccaaaac accatctaaa   1020
gccgcccaat aagccaaggc tttttctaaa ggcaaatgcc gatccattgc caaagcctca   1080
tccgcaaaag ccacccgacc ccatttttca atatgacccg aaaaaggttt cagaaaaccc   1140
gccaacagac gcaaaaggct gcttttacca ataccatttg cccccgttat taaaacggcc   1200
tcaccagcct tcacttcaaa agacaaatgg gtaaacagta agcggtcgcc tctcaaacaa   1260
ctcacgtcat gacacgccag ccttgcattc ccgaaatcgg acagcctttt tctccccaac   1320
aagatcccgt caaagggata gaaaacaata tcaaaaatct atgtcttcac actaccccaa   1380
gctaaagcac tttaacgcca cagaaaaacc aagagagcaa aaagataccg tttcaaaata   1440
atactttgtc tatcagaaca gacaaatagc agggctatgc aaaacccttt atgcggatcc   1500
catcaaatcg tgaatttaat gtactgatgg caatgccaga cggacaaaca ggccacctaa   1560
atcttcactt tcttccaaag taacactgcc gccataaatt tcgaccacat cgcgaacaat   1620
tgccaacccc aacccagtcc cgggtttatc tgtatccaaa cgcgccccgc gtttaaacaa   1680
ctgcccacgg agattttcag gaatacccgt gccatcatct tcaatcagga tttcaaccga   1740
cttaccctgt ttttctaccg taacaaaaac gcgtccctga ccatatttag cagcattttc   1800
tataagattt cccaaaatct cgtccagatc ttgtctttct attctgacaa cagcgtcctt   1860
aactcctgca agatcaatcg ttgcatgagg ataaagccga gtaaccgcgc gttctaccgc   1920
cagtaaagca ggccatacct ctgcttggct ttgggcattg ccccgccgtc caatagcccg   1980
cgctcgcgcc aaatgatgat cgacatgccg ccgcatggtc atcacctccc gcaaaacaac   2040
ttctttcaag gcatcgctat tggcattcgc ctcattagtc acaaccgtta atggcgtttt   2100
caaggcatga gccagattac cagcatgtcg cctagcctct tcggcttgcc gttcgttatg   2160
agacaacaaa gcgttcaatt cttcaatcaa aggggcgact tcattcggca tccggtcatg   2220
aatacgcgaa gcctgaccat tacggacagc actaatctcg cgccttaatt tccgcagcgg   2280
ccataatccg atcgtcacct gtaaaacggt aataacaatc aaccccgtgc ctaaaatcaa   2340
aaaggctttc acaagggtat ggcgtaattt tttaatctga ttgtctaaag aagtacgaat   2400
ttcagcgact tggaatcgcc ataaaacaga cgaaccgggt aagcggacat cccgttccat   2460
cactcgcaaa gtgccatcag aaaattcgtc gctatcatat gtccgcacca attgcccttt   2520
aggcatcgga ttgacttgta gcgagcgatc ccaaagtgaa ggggacggaa atctttcata   2580
tccgctaccg ctcacctgaa aataaagccc gctatgggct tccaaaaaac gctggtcacc   2640
caaaggccga ttcagtcgaa ccgccccttc gggatcaatt tcagaagaag cgatcatcgc   2700
cgccaaaaca taatcaagct ggctgtcaaa attatcggtg acggcttggg tcagcacccg   2760
atccaaggtt acgccgccgc ccgatagcag gataaatatc cacaaagccg aaatagcaat   2820
caaccggcgg gtcaaagaac cggtaggacg tattaccggc tcctgactgt tattttctcc   2880
gaccggattt ccgctttttt cgattttttt ccggcgaaag aaacgactaa aaaaacgctt   2940
tcggccaccg ctaggggaag aagcggaagc cataatcagc cgttattccg atcctctggg   3000
```

-continued

```
tcgttcaaag cataacccaa accgcgaata gtcgtaataa catcctgccc cagtttctta   3060

cgaatacggg ttacaaagac ttcgatcgta ttagaatcgc gatcaaaatc ctgatcgtaa   3120

atatgctcga tcatttcggt gcgactgaca actttgcctt tatgatgcat cagataggaa   3180

agcagcttat attcctgcgc cgtcaatttg acaggctcac ccgctaaagt cactttgccg   3240

gaacgagtgt caagccggac atcacctgcc gtcaattcag aagacgcatt accggaagcc   3300

cgtcggatca aagcccgcaa acgggcaatc aattcttcgg tctggaaagg cttggtcaga   3360

taatcatcag caccagcatc aagaccagca actttatcag accagctatc ccgtgcagtc   3420

agaaccagaa ctggcatttc gcggccttct ttgcgccaac gatcaagaac ggtgagaccg   3480

tcgacttcgg gcaaaccgag atcaaggaca acggcatcat aattttcgct cgagcctagg   3540

aaatggccat cttcgccatc tgtcgccaga tcgacagcat agccagcccc ttccaaagtt   3600

gttcgcaact gacgggaaag cgtcggctca tcctcaacga ttaaaacgcg cataccgttc   3660

tctttctcgc ttccttcttt ttattcttgc aaggctaaac cccaagcctc gttttcggtt   3720

gcatgcgtta ggaaaaggca acctgaaaac agctattata gatattttca ggctgacaga   3780

acactgcaaa agaaaagaaa ggtcggaata accttttttcc ccgaaatcaa tcagaaagca   3840

ttattttgta aaatataata tttatagcag cttaactatc tccaataagc ggccttgctg   3900

gtatgaccaa ttcccggatt aaaagaattc gtcgggtcta attcgtgata atgcgtcttc   3960

aggctgtctt tggcgtaata gagatgcccg acattatgtt ctgctggata ttcggcatgg   4020

cggctgtcca aaattttcca catagcatgt tcgatatcag cgcaatttcc accttttttg   4080

acgatataat cctgatggaa cacctgacaa aagaaatggc cataatataa aatatggctg   4140

attttatcag taatttcaga cgggagatgc tcttcccacg ccctgttatt acgcggcaaa   4200

gcaatatcca acgcaacgat atcttcgact tcatcctgat gaacgtcacg atagcggata   4260

gccgccccag cggcggcaaa acgatgcaga aaagcctttt tcccttcttc atcgctacat   4320

tcaaaataac caccacttgc cttttcgaaa aagtctttca gaaaactgcg cgcttcttca   4380

gttccttctt cggacacttt caaaatcaga tgatgttcat agcggtcacg gaaatcatcc   4440

attcgcttag gcagatgatg cgggaacaga gtggacgcaa attgcatcac ccgatcgctc   4500

aaataacgcg gcaagaaact gacacggttg tttaaaccat caaaccaacc cttcatggcg   4560

aaaagctgcg gcaagcgatc ggtgccgaga tattcaatcg ctaagaaagt atcttttccg   4620

tatttcgccg caatatcata agcatggcga tgcatatatt cgcctgaaat tggcaaatat   4680

ttgaaagact tcaacacctg ccgtcgaagc tcggttaatt catcaggatc attggtgccg   4740

atataaaaaa ccttggcatt tttttgctgc ggaaaagtat caagtcgcac cgcaaaaacc   4800

gccacttttc cggcactacc agaagattca taaagacgag acgggtcagc attaaagcgc   4860

gcgggtgtct ctgcctcaat atcgcgaata tgattatgat attcacagtc ggaagcatgt   4920

ttgctttcgt cattg                                                    4935
```

```
<210> SEQ ID NO 23
<211> LENGTH: 23
<212> TYPE: DNA
<213> ORGANISM: Artificial Sequence
<220> FEATURE:
<223> OTHER INFORMATION: L-270F

<400> SEQUENCE: 23

ggaaagtcaa gcttatcatc tag                                             23
```

<210> SEQ ID NO 24
<211> LENGTH: 34
<212> TYPE: DNA
<213> ORGANISM: Artificial Sequence
<220> FEATURE:
<223> OTHER INFORMATION: L-270R

<400> SEQUENCE: 24
gtgagttgtt aaccaatttt atactccatt catc 34

<210> SEQ ID NO 25
<211> LENGTH: 25
<212> TYPE: DNA
<213> ORGANISM: Artificial Sequence
<220> FEATURE:
<223> OTHER INFORMATION: R263F

<400> SEQUENCE: 25
gacaatacaa agtactgata aagga 25

<210> SEQ ID NO 26
<211> LENGTH: 33
<212> TYPE: DNA
<213> ORGANISM: Artificial Sequence
<220> FEATURE:
<223> OTHER INFORMATION: R263R

<400> SEQUENCE: 26
ataagcctgt taacttaccc atcttgtccg acg 33

<210> SEQ ID NO 27
<211> LENGTH: 30
<212> TYPE: DNA
<213> ORGANISM: Artificial Sequence
<220> FEATURE:
<223> OTHER INFORMATION: ATCC19254F

<400> SEQUENCE: 27
catatgaaga tttttgctta cggcattcgt 30

<210> SEQ ID NO 28
<211> LENGTH: 22
<212> TYPE: DNA
<213> ORGANISM: Artificial Sequence
<220> FEATURE:
<223> OTHER INFORMATION: ATCC19254R

<400> SEQUENCE: 28
ttaatattca acagcaatag ct 22

<210> SEQ ID NO 29
<211> LENGTH: 29
<212> TYPE: DNA
<213> ORGANISM: Artificial Sequence
<220> FEATURE:
<223> OTHER INFORMATION: LMG18811F

<400> SEQUENCE: 29
catatgaaaa tttttgctta cggcatacg 29

<210> SEQ ID NO 30
<211> LENGTH: 28
<212> TYPE: DNA
<213> ORGANISM: Artificial Sequence
<220> FEATURE:
<223> OTHER INFORMATION: LMG18811R

<400> SEQUENCE: 30
ctgcagtcag tatttaacag cgattgca 28

<210> SEQ ID NO 31
<211> LENGTH: 29
<212> TYPE: DNA
<213> ORGANISM: Artificial Sequence
<220> FEATURE:
<223> OTHER INFORMATION: NBRC3426F

<400> SEQUENCE: 31
catatgaaga tttttgctta cggcattcg 29

<210> SEQ ID NO 32
<211> LENGTH: 28
<212> TYPE: DNA
<213> ORGANISM: Artificial Sequence
<220> FEATURE:
<223> OTHER INFORMATION: NBRC3426R

<400> SEQUENCE: 32
ctgcagttaa tattcaacag caatagct 28

<210> SEQ ID NO 33
<211> LENGTH: 3168
<212> TYPE: DNA
<213> ORGANISM: Artificial Sequence
<220> FEATURE:
<223> OTHER INFORMATION: Nucleotide sequence of upstream of ORF ZMO0087 - ZMO0089

<400> SEQUENCE: 33
tgaaatggcc tctgcgatat atcgaataaa ccgataaaga cgcttttttt tatctgaata 60
atcacccgca aaaactcgga aattctttgc agagcaatcg tttccttatc aaaactaccc 120
tcgcccctaa tcaaaaggca acgtcctcag gacagattgc tttctctttc gggcatagag 180
gattcaatga aaggaagaag atggttaaaa ttgatctcac cggcaaaaca gctattgtca 240
ccggatcatc cgaaggcatc ggcctaggca ttgctattcg tctcgccgaa gcaggtgcaa 300
aggtcattgt taatggccgt catcaagaaa aattgaatag tgcaattgcc gaagtcaaaa 360
aagccgctcc agaagccgaa gttgttggct tcgtcggtga tcttggacag gccgaaggct 420
gcgatgcctt ggtcaaagcg catccggctt gcgatattct ggtcaataac gtgggtattt 480
tcagccccca aggcaatttc ttcgatatcg gcgatgattg ctggcagaat ttctttgaca 540
tcaatgtaat gtccggcgtt cgtctctccc gtgcctatgc caagaaaatg gctgaaaaag 600
gctggggtcg ggtgctgttt atttcgtcgg aatctggctt caatattcca gaagaaatgg 660
tgcattacgg cttcagcaaa accgcccaga ttgcaatcgc ccgtggcctt gccaaaacgc 720
tggcaggaac cggcgttacc gtcaattctg tcctacctgg gcccacgctc tcggatggct 780
tgaaaaaaat gctggaaccg gaagtcaaaa aaaccggaaa aagctacgaa gaagcggcag 840
ccgattttac caaaaacctt cgcccttctt ccattattga acgcgccgct agtgtcgaag 900
aggtcgccaa tatggtgctc tacgccgcct cacctttggc ttctgccacg accggagccg 960
ctctccgcgt tgaaggcggt atcctcaatt atctctaaaa atacagcgat aaccgcaaaa 1020
agggctgccc tttagcagcc cttttttttta cctcacatct caataactcg atagcctgaa 1080
aaaggcataa tggcttcggc ctcttccact acgcagaaag ctatttctat tttacattca 1140
caaaaaccgt cattcgatca tcacctactc tcaaataacg ttccatcgac ctccgcatct 1200

```
cctcgagacc taaagactac ctaacgacaa tctctcactc tcctctaatc acctctacat   1260

tagagaactc tttacttctg tttcaaagta taaatgaatt aaatattcag tcaccagtga   1320

cgttattaaa aatataaata attaccacaa aataatgcac ttaatatcca atgatttttc   1380

atgggtaaat aatatcatat tatcaaaatc attggatttt taaaggatac agcaatgcct   1440

ttatccaata tcacctactg gccgagcatc aatctcactc tatataaagg gaatacagca   1500

tccacccaaa aaaccgataa tgcggcttca aatacgacgt cacaaaatca ggaaaactct   1560

gtccagatat cagataaagc ccaatctctc tctgatacag aaaatgcaca gccctctctt   1620

aaatcaagaa ttaacgccct tttcaaagaa gcccgcgatg aaggttcctt catcactttt   1680

gactcttcca aaggaggcga atggatcgat ttttcttctt ttacagatga cgaattagct   1740

caaattggaa aagatagaaa tcacgatttt tcagaagcgt tatcaaaaca tgccatcgcc   1800

acattggcag agcgcgtcac catatccttg gaaccatttg aggctacgat tggatatggc   1860

gattttcgag gcgatgcaaa ggctataaga accttatata gccatatgag tcaggatgtc   1920

cgtgatgttc tggggtggac agaaagcatg gtagaagccg cagaaaagtt agccgaaaag   1980

aatacagaaa aatcagacga ttttaatatg gatgccctct gggaaatgtt gatggaggcc   2040

gctaaaaaag gcggcatttt gctccctaaa aagaacatcc tatcgacctc ggcggcatcc   2100

tttgaagatt taaacactca acaataaccc gtttacctct atcatataat tatatctaag   2160

ttataggccc ctttacttct gtttcaaagt ataaatgaat taaatattca gtcaccagtg   2220

acgttattaa aaacataaac acttaccaca aaataataca cttaatatcc aatgattttt   2280

catgggtaaa taatatcata ttgcccaaat cattggattc ttaaaggata catcaatgcc   2340

tttatccaat atcaccccgg gaccaaggga taacttactt ttatataagg ctagccaaaa   2400

tataaatgtc agaacaacag cttcaaaggt aatccaaccc acatcgaatt catcagaaaa   2460

tagcgtccaa atatcagaag aggccaaagc cgcttttaaa agccagaaaa tgtctaatac   2520

tgaaaacgct gacaattcta tcaaatcaag acttaacaag ctcttccaag aagcccgcga   2580

tgaaggttcc ttcatcacct ttgactcttc taaaggcggc gagtggcttg atgtatcgtc   2640

tttcacagat gatgaattgg ctcaaataac gaataataag gaaggcagct tttcaaaaga   2700

tttgtcaata tatgcccaag ccatgctagc tcaacgtgca aaactgtctt tggaaccgtt   2760

tgaagccgcg attggatatg gagattttcg gggagaggca gcggcaatca ggacattata   2820

taaccatatg agccaaaatg tccgcgatgc tctcggatgg acagagagca tggttgaagt   2880

cggtgaggaa atggccagcc attccggcaa agcccttaat aaatcacatt taaaaacgct   2940

ctgggacatt ctgctagaag tcgcccaaca aggcggatta tctattcaaa atagccctaa   3000

tcaagacaac ctacaaaaat ccgatgataa agctatatag cagcgttaaa ataataccct   3060

gaacatcatt acatcatttg ttacgattat tactcaaatg gacaatttac aaacaatctt   3120

atctcaccct atatctccta aaaagatcat atttgtagga attttatg                3168
```

```
<210> SEQ ID NO 34
<211> LENGTH: 3159
<212> TYPE: DNA
<213> ORGANISM: Artificial Sequence
<220> FEATURE:
<223> OTHER INFORMATION: Nucleotide sequence of downstream of ORF
      ZMO0087 - ZMO0089

<400> SEQUENCE: 34

taacccgttt acctctatca tataattata tctaagttat aggccccttt acttctgttt     60
```

-continued

```
caaagtataa atgaattaaa tattcagtca ccagtgacgt tattaaaaac ataaacactt    120
accacaaaat aatacactta atatccaatg atttttcatg ggtaaataat atcatattgc    180
ccaaatcatt ggattcttaa aggatacatc aatgccttta tccaatatca ccccgggacc    240
aagggataac ttacttttat ataaggctag ccaaaatata aatgtcagaa caacagcttc    300
aaaggtaatc caacccacat cgaattcatc agaaaatagc gtccaaatat cagaagaggc    360
caaagccgct tttaaaagcc agaaaatgtc taatactgaa aacgctgaca attctatcaa    420
atcaagactt aacaagctct tccaagaagc ccgcgatgaa ggttccttca tcacctttga    480
ctcttctaaa ggcggcgagt ggcttgatgt atcgtctttc acagatgatg aattggctca    540
aataacgaat aataaggaag gcagcttttc aaaagatttg tcaatatatg cccaagccat    600
gctagctcaa cgtgcaaaac tgtctttgga accgtttgaa gccgcgattg gatatggaga    660
ttttcgggga gaggcagcgg caatcaggac attatataac catatgagcc aaaatgtccg    720
cgatgctctc ggatggacag agagcatggt tgaagtcggt gaggaaatgg ccagccattc    780
cggcaaagcc cttaataaat cacatttaaa aacgctctgg gacattctgc tagaagtcgc    840
ccaacaaggc ggattatcta ttcaaaatag ccctaatcaa gacaacctac aaaaatccga    900
tgataaagct atatagcagc gttaaaataa taccctgaac atcattacat catttgttac    960
gattattact caaatggaca atttacaaac aatcttatct caccctatat ctcctaaaaa   1020
gatcatattt gtaggaattt tatggataat atcatcaaca tcatcgcagg cgtgattgca   1080
ctctatttca tcgccgcgat gctcatgttt ttctactggc tctattttca taaaggcagc   1140
ctgaaaaagg ccttaatcca tatcgttgtt tccttgggat tactttgcct tctggtgggg   1200
ggtcaaatgc tccgctggaa aagcatcaat gcccaaaatg cagcagaaca ggcagcaaaa   1260
atgccaaaag ctgttaccat tcagcctgac cttttagcga tattgcaggc taatcccgat   1320
cctgcttccg ttgaaccgac aaaactcgct gccatcgcta atttagccga gcaacattta   1380
ggcgaagctg gtaaagaata tgaagcgcct ttgaagaaat atttcgtcta ttacaacagc   1440
catattgcat ccgaaaaact gcctgacaca atggccgcta tcaaattcga tgcacaacgc   1500
cgcaatgctg aacgcggttt ttaatctccc aatttcaaga taatcagcga tgatatagcc   1560
tcggaaagcg ccctcaatcg cttccgaggc gaattgatag attacccgac aataacagcc   1620
tttcaaaaag acagatttcg gcctcacaaa aaaaattgcg cttcatgtga atgaaggctt   1680
gcaatatgtt gaaatcctcc gcaattttat ctccgtgttg agacaatatg aactagtcga   1740
tcgggtttta agctacgatc caaacgccga tgaagcgttg ataaaccgcg cctatgtttt   1800
cgccatgaaa gcgcatggca atcaaaaaag ggcaagcggc gatccctatt tcagccaccc   1860
gctagaggtg gccggaatcc tgaccgatat ccatatggat gccgaaacga tcataacggc   1920
catcctgcat gatactgtcg aagacactgg aacgaccagc gaagagctgg caaaactctt   1980
tggttcagcg gtggctcgtc tagttgatgg tgtcacgaaa ttatcgcgaa tcgaggcaca   2040
atccgtcacc gaacgcgcgg ctgaaaatct cagaaaattc ctgctcgcca tgtcagacga   2100
catccgcgtt cttctggtca agctggcaga ccgtctgcat aatatgcgga cattgcattt   2160
cattaaaaag gaagaaaaac gccgccgtat cgcgcgtgaa accatggata tctacgcccc   2220
gttggcagaa cggatcggca tgtatgaatt catgcgtgag atgcagacac tttccttcca   2280
atttttggaa ccggaagcct atgcttcgat cacaaaaagg ctggaacaac tcaacaaggg   2340
tgatacgggt caaatcaaac gtatcatcaa tggcatcgag gaattacttg agaaagccgg   2400
```

```
tatcaaagcc aaggtctcag gccgccaaaa acaccccta t tctatctgga aaaaactgga   2460

agaacgccat atcagctttg accagctttc agatgtcatg gcctttcggg tcattgtcga   2520

taatacagaa gattgctatc gggcattagg cattttgcat ggcaaatggc caatggtgcc   2580

ggggcgtttc aaagactata tttcgacacc gcgccgcaac ggttacagct cgcttcatac   2640

tgcggtcatt cacaatgaaa atctccgtat cgaaatccag atacggtcac aagcgatgca   2700

cgaacaggcc gaatatggcc ttgctgccca ttgggcgtat aaacagaaaa cggtgccgga   2760

caaattccag caaagcggct ggattcgcga tttggtcgaa attctggaca atgctgaaag   2820

cccagaagag ctactcgagc ataccaaaat ggcgatgtat aaagaccgta tcttcgcctt   2880

caccccaaca ggtgagctta tacagcttcc cttgggggca acaccggtcg attttgccta   2940

tgccgttcac acggatttgg gcgaccaaac cgtgggtgcc aaagtcaatg gccgcgtggt   3000

gccattaggc acgcgcgttg aaaatggcga tcaagtcgaa attctgcgtt cagccgcgca   3060

aacgccccaa atttcatggc tcaattttat taccacaggt aaagcccgcg cggctattcg   3120

ccgttttgtc cgccataaag agcggagcga taccctta c                         3159
```

<210> SEQ ID NO 35
<211> LENGTH: 28
<212> TYPE: DNA
<213> ORGANISM: Artificial Sequence
<220> FEATURE:
<223> OTHER INFORMATION: 87F

<400> SEQUENCE: 35

```
tgaaatggcc tctgcgatat atcgaata                                        28
```

<210> SEQ ID NO 36
<211> LENGTH: 31
<212> TYPE: DNA
<213> ORGANISM: Artificial Sequence
<220> FEATURE:
<223> OTHER INFORMATION: 89R

<400> SEQUENCE: 36

```
gtaagggtat cgctccgctc tttatggcgg a                                    31
```

<210> SEQ ID NO 37
<211> LENGTH: 30
<212> TYPE: DNA
<213> ORGANISM: Artificial Sequence
<220> FEATURE:
<223> OTHER INFORMATION: del 89F

<400> SEQUENCE: 37

```
taacccgttt acctctatca tataattata                                      30
```

<210> SEQ ID NO 38
<211> LENGTH: 30
<212> TYPE: DNA
<213> ORGANISM: Artificial Sequence
<220> FEATURE:
<223> OTHER INFORMATION: del 87R

<400> SEQUENCE: 38

```
cataaaattc ctacaaatat gatcttttta                                      30
```

<210> SEQ ID NO 39
<211> LENGTH: 3140
<212> TYPE: DNA
<213> ORGANISM: Artificial Sequence
<220> FEATURE:
<223> OTHER INFORMATION: Nucleotide sequence of upstream of ORF
ZMO0381 - ZMO0384

<400> SEQUENCE: 39

```
gaagaagcgc agaccctatc tcaacgatct ttggagcttt taaggccaac catcagaacg     60
attgattcag aattatggtt ttcgtggaat cctcgtttca aaactgatcc ggttgaccgg    120
atgttgcgcg gcgaaacgcc accgaccggt gcggttgtgg ttcaagctaa ttgggaaaat    180
aatccgtggt ttccctcgcc gttggatcaa gaaagacggg attgcctgac gaatgatcct    240
gataaatacc gccatatatg ggaaggggga tatgcggaga taaccgaggg ggcttattat    300
gcccaagcct tggccaaagc ccgatctgaa aaacggatag ctgtcgttgc cgctgacccg    360
ttaatgacct tgcgggcggt ttgggatatc ggcggcacgg gtgccaaagc tgatgctacc    420
gcgatatgga ttgtccaata tgtcggacgg gaaatccgtt tcctcgatca ttatgaagcg    480
caagggcagc ccttatctgc ccatcttcat tggttgcgtt cgcatgatta tggcggggct    540
ttatgtatct tacctcatga tggcgcgcag catgataaaa tcgcctcaac aacctatgaa    600
ggcgcgttgc gtgaagccgg attttcggtg cgggttattc ctaatcaggg agccggagcc    660
gcaatgcagc ggattgaagc agctcgtcgg ttatttcccc agatgtggtt tgatgaaaat    720
cactgccgtg gcggtttgga agcccttgga tggtatcacg aaaaacggga cgaaatacga    780
gggatagggt taggacccga tcatgattgg tcaagtcatt ccgcggatgc tttcggtttg    840
gcggctattg cttgggaacc gcccgtaacg agccggaaaa tcacctatag caataaagga    900
atattttaat gaaacgggct gaaaagagct ttctgccccg aagggggcgc tatgtctttg    960
gatattgata gcaatataga tttgaaagaa aaacagacgg atttcttgct ttctaaccat   1020
gagttattag cggtcttgca cgaaaaagcc gatcaagcag aaagctggca taatagttta   1080
ctggctgaag atcaggccaa tgctatcgat ttttatgaag cgcgaccctt tggggatgaa   1140
gaggacggtc ggagtcaggt cgttagtccc gatgtcgccg aggtagtcga ttatatgacg   1200
atcagcctgt tacggacgat tgtgtcaggc gatcgcgtga ttgaatttga gccgatagcc   1260
gccgagcaag cgcaagatgc cgatgatgcg accgaggcgg tcagctatgc ttttatgcat   1320
gggcaggacg gctataaaat cctgcatgac tggatccagt cgggattgat tgaaaaaata   1380
ggcattatca aaaccgcagt cctatcggaa agacgtgcta caatccgcca tattactgtc   1440
gatgatgatg ccttggcggc tttgttgatg gaggccgagg ataatcccga tattcagatt   1500
accttgaata atgacgatgg tagcggccaa tatgaggtaa ccgttacccg ttatcagctt   1560
caaaaacgct atgtcgatat gccgattccg tccgaagaat atcgcgtttc ggccagaact   1620
cgccatgaag atgatgctga ttatcaggcg catgtcagtt ataaaacgct gtctgatctt   1680
atttcgatgg ggttcgatcg cgatattgtc gagagcctgc caagtgataa gagttttccc   1740
aatagcgatg gccgttctga tgccagatgg cgggatgaat cctttctgtc cggcagtagc   1800
gatcaagcca atcgcgaagt tctcttatat gaagaatatg tccgcatcga tcgggatggc   1860
gatggcattg ctgaattatt gcagattttt cgggtaaaag atgtcttact ttcgattgaa   1920
gaagtagacg aagcgccctt tgtcgtttgg acacctttcc cgcgcgccca tcggatgatt   1980
ggtaattctt tggccgagaa ggttatggat atccagcggg ttaagtcagt gctgatgcgt   2040
caggctttgg atggggttta ccagaccaat gcgccccgta tggcggtaaa tgtcgatggt   2100
ttaaccgaag atacttttga cgatttattg acaattagac ccggggcgat tgtccgttat   2160
cggggtggca ttccaccaac gccgttaaat gccggtttcg atatccaaaa atctttgggt   2220
```

-continued

```
atgatcgaat atatgcagtc ggctcaggaa agccggacgg ggattacccg tcttaatcag   2280

ggattggatg ctgacagtct taataaaacc gcgaccggtc aggccttgct tcaggcgcaa   2340

gggcagcaaa tggaagaata tgttgcccgc aattttgcac aaagtcttgg gcggttattc   2400

caaaagaaat tatggctgat gattgcatcg ggcgatccga tggcgatcaa ggttgaaggt   2460

ctgtataaaa cggttgatcc ggctttgtgg ccgccggata tgcgcgtgcg tgtcacggtc   2520

ggattgggat cggggcgaaa agatcagcgt ttggcctatc gtcagcagtt gttatcgatt   2580

cagcaacagg cgttggccgt tggtttaacc ggttccaagc agatttataa taatatcgcc   2640

gcaatgatcc gagattgtgg tttgggtaat ccgactgatt atttgattga tcctgatatt   2700

cgcttggcag gtaatcaggc tgaaaatcct gtgaataata attcggctgc ggcgcaaaat   2760

tcttctggca gtgtaggaaa taatcccgat tatacagagt tgaaagcccg acaagatatc   2820

aatcttcaag ggcagaaaat ggctgctgat caggaacgga gtatggccga atttgctttg   2880

aaaaagcagg aaaccgaggc caagctggcg atgcaacagg aagagcataa acagcgtttg   2940

gccttggtgc gcgaaaaagc cgaagaagag gccattttag caaggcaacg ttccgatttt   3000

gaagcctcgc ttgccaagga aacagccgat cgtaattacc agatcgcttt gaaattggca   3060

gaagctggga aaaatattcc agcggataaa aagggggata gggtgccgca aaacaaagca   3120

gggggcgcat tggataaata                                               3140
```

<210> SEQ ID NO 40
<211> LENGTH: 3212
<212> TYPE: DNA
<213> ORGANISM: Artificial Sequence
<220> FEATURE:
<223> OTHER INFORMATION: Nucleotide sequence of downstream of ORF ZMO0381 - ZMO0384

<400> SEQUENCE: 40

```
tgtagtttat acgctgcatt aaatgaaaag gcggtgaatt cgggggacgt ccaaccgtca     60

tagacgagga taatcccgag ccaagcttga ggtgaaaatc tcttgaaggt gtaacgacta    120

acagccgagc ctaccgacaa aaaacgataa aactgatgcc gttatttctg aaaaagaagc    180

gggtatgatt ctttgcattt ttactgaaaa tgccggaaat ttcggaagaa atatttcagt    240

ctttttgtc catggcagta atgctgacac gagtgccgcc cgcgaaagcg atgatatagt    300

ctgagccttg caggaatgta aggaagcaag ggataaagag cctttgcggt aacaatctgg    360

aaacaccttt tgtaacagct atcggtcaaa cgacagccaa aaatacctat accgaatggc    420

agaccgacaa tcttgccagc gctaatgccc agaataaaca ggtcgaagga gctgatcttg    480

ccaatgaaag ccgccagcca acggttcggg tcggcaatta tacccagatc atgaccaaag    540

ttgtcgggac atcgacgacc gatcgggcgg tgcataatgc cggacgcggt gatgaacatg    600

cctatcagtt ggcacgtgct ggtcaggaat tgaaacgcga tattgaggcg cgctttactg    660

gtaattttgc agccattccc ggagatgggg cagtcgtcgc gcgtgaaaca gcaggagctt    720

tggcatggct gcgcagtaat gcccatcgtg gcgacggcgg tgccaatccg gtgatgtccg    780

gtggcgacaa tggcagcggt tatccgacaa cagcggcgac cacaggtaag gcgcggcttt    840

ataccgaggc tttgttaaaa gaagttttgg gcgatatctg ggtcagtggt ggtcagccaa    900

atatggtgat tacctctttg aaactgaaac agacagcggc agcctttccg ggttggcttt    960

ccaaccggcg cgatacgggc gaccagaaag cgcgtattat tgccggtgcg gatatctatg   1020

tttccgatgt cggcgaagtc cagtttgtac ctgatcgttt ttgcgacaat agcagcgctt   1080
```

tggtcattga ccctgaatat tggtcggttg cgaccttaga tccgattcag aaacggtctt 1140
tggcaacaac ggggctggct gatcgtgatg ccctttatac tgaaattgcc ttgcgctgcc 1200
ataatgaagc agcctccggt gttttggcag atttaagcgc tgcctgattt tcgtgatcgg 1260
gaggatgtct tcttgcaaga catcttcccg taaaaattcg gaaagggaat attccatggc 1320
tttttcttct gccttggtcg cctttttcaa aaaaaaggtc gggctgggct tgaaatgcgg 1380
ctttgatatt cgagggcatg atggctgctg aacgcttgtt atcctataat ccggtgacgg 1440
ggcttaaaag ttggttttcc tcttcagagg agaatcaggg cagttggcat atccgctatg 1500
aacaggattg ttctgcggct ttggaagcca ataaacaggc acaaaatgaa gatttttgatc 1560 ggcgttcttc gatgtggcac gccgcccatg ttccagccgt cgttttgatg gaatggctgg 1620
tgaaatatgg tgtccgatat tgggacaaaa atcacgcgcc tgccgttcgc cgtttactca 1680
atcatcctga ttatcgctat ttgcgcgtta atcactttat tatgtgagca tggctgatgg 1740
ctctttttat tgatgcccaa aatctggaca gtctcacccg ttatgatggc ctcttaaagg 1800
cgattgcctt gtggttggaa cgcgatgatc tggccgatga aatcccttat ttcgtgcaac 1860
tggcagaagc ccgttttcgg cgattgttga ctaatcccga attggaaacc gaaataacgg 1920
tagcggcagg ctgtcctgtt acgttgccgg atgattttga ggccttgcgc ctgctttatc 1980
cggcaggcgg tcgtcgcgat cgggcttttt tgcagctgtc gccagatgtt tttcagcagg 2040
gcaagcatca gaataaatct gttttcaccc tgatggcagg gcaattatgg atatcgcctc 2100
ttcctgaaac agaaacggct ttttcgttgg tctatcgtgc ggctttgccg tctttatcct 2160
tgaatcgcca gagtaactgg ctgttggcct cccatcccga tatttattta ttcgggtcgt 2220
tattacaggc cgagttcttc ggatggaatg acagccgttt gccggtcatt aaatcggcgc 2280
tggatgaagc cttgggcgag ttaaataaag caggattgcg caagcgttat gcagaaagca 2340
ccttggttgc gccatcgcct gtcgtggaag cggtgaaagg cacttaccga tggtaagtca 2400
gcgtctttta ttcggggctt atgaacccga tcaaccaccg tatatgagtg gatcactgcg 2460
ccatttaagc aatgcctatg ccacgacaaa tggatatcgt ccagtcggag gcttcaagcc 2520
ttttgcggcg gcgttgccag atatttttat gggggctgcg gctttttag ggtcagatgg 2580 ttcgacttta ttggtcgctg gcaccaaaga cagtctttac cgctatgttt ccggtaattg 2640
ggaggccttg gtaacagcct tgccggctta tggacgatgg catttcaccc aatttgggga 2700
tcgcattatt gccgttaacg gcagtgccac ccgaaaaata gatatcctta ctggaaaagc 2760
cgacagcata gcagatgccc cgacagctga aatggtgacg actattcggg attttgtggt 2820
gtatggccgc gcttctgccc agaagaatct aatccaatgg tcgggcttta ataacgaaaa 2880
cagcaatgtc atcggcacca atcaggccgg ttatcaaccg atgctgactg gtggcgacat 2940
aatgggcatt atgggcggcg aatatggcgt tattatccag cgttcccgca ttgtccgtat 3000
gagttacacg ggggacagct atatctggca gtttgatgag atcagcgcca atatcggggc 3060
gattgcgtca ggctctatag cacaagctgg gcatcaggtt ttctttctgt ctgatcgggg 3120
tttcatgatg acagacggcg tttctgtcac accgatcggc aatgaacggg ttgaccggtg 3180
tttttttgaa agctggccaa gggacagttt gg 3212

<210> SEQ ID NO 41
<211> LENGTH: 32
<212> TYPE: DNA
<213> ORGANISM: Artificial Sequence
<220> FEATURE:

-continued

<223> OTHER INFORMATION: 381F

<400> SEQUENCE: 41
gaagaagcgc agaccctatc tcaacgatct tt 32

<210> SEQ ID NO 42
<211> LENGTH: 33
<212> TYPE: DNA
<213> ORGANISM: Artificial Sequence
<220> FEATURE:
<223> OTHER INFORMATION: 384R

<400> SEQUENCE: 42
ccaaactgtc ccttggccag ctttcaaaaa aac 33

<210> SEQ ID NO 43
<211> LENGTH: 31
<212> TYPE: DNA
<213> ORGANISM: Artificial Sequence
<220> FEATURE:
<223> OTHER INFORMATION: del 384F

<400> SEQUENCE: 43
tgtagtttat acgctgcatt aaatgaaaag g 31

<210> SEQ ID NO 44
<211> LENGTH: 27
<212> TYPE: DNA
<213> ORGANISM: Artificial Sequence
<220> FEATURE:
<223> OTHER INFORMATION: del 381R

<400> SEQUENCE: 44
tatttatcca atgcgccccc tgctttg 27

<210> SEQ ID NO 45
<211> LENGTH: 3280
<212> TYPE: DNA
<213> ORGANISM: Artificial Sequence
<220> FEATURE:
<223> OTHER INFORMATION: Nucleotide sequence of upstream of ORF
ZMO0390 - ZMO0394

<400> SEQUENCE: 45
atgatccgat ggctggaaat aatgcggata tgccgccatc cgatcaggca tccgacgatc 60
agagcaatat gggcgcaacg gcagcaggaa atggtgccaa tcaaggaaat ggtcagccgg 120
atatgagtgc ggcttggcaa gaacattgtc gggccttgca ttaccattat gccgaccagc 180
ttgctaaata tgccgaagcg attaccccga aaaaacctga tccgcagtta ttggtcagtg 240
atccggcaag ctatgccgca caattggcaa gttatgaaga cttaacggcc aagcgtgacc 300
aaattgttca ggaagttatc cagatttctc gccagaatga aatggctgaa ctggctgcca 360
gaagggcatg ggcgcagggc gaacatcagc gtttgatatc gcttttgcct gaatggggcg 420
atgataatca gagaccggct atcttggcgg cttttgaaga aacgggacgg catctcggtt 480
atccagatca tgttttggcc gaggctgatt ccaacgacat tatggctttg aaaaaagccc 540
atgaatggcg aagaaaatcc gaaaaatggg atgccctaca acagggtaag gcggcggcta 600
tcaaatcagc caaaacatcg agaaaaaccg cagttccagg aacgtcccag ccttatggcg 660
cggccaaaag ccggaaacta aatgaatcat tggggcagct tcgcgaaact ggcgatgtcc 720
ggtcagccgc tgcggcgatg aacgcccttt ttaaataatc tacttttcaa ggaattttga 780

-continued

```
attatgtctg ttgcctctaa taccgtccaa acctattcgc gtgtcggtat tcgtgaagat    840
ctttccgata ttatttataa tatcagcccg actggagtct tggtccgtta atgtagttta    900
tacgctgcat taaatgaaaa ggcggtgaat tcgggggacg tccaaccgtc atagacgagg    960
ataatcccga gccaagcttg aggtgaaaat ctcttgaagg tgtaacgact aacagccgag   1020
cctaccgaca aaaaacgata aaactgatgc cgttatttct gaaaaagaag cgggtatgat   1080
tctttgcatt tttactgaaa atgccggaaa tttcggaaga aatatttcag tctttttgt    1140
ccatggcagt aatgctgaca cgagtgccgc ccgcgaaagc gatgatatag tctgagcctt   1200
gcaggaatgt aaggaagcaa gggataaaga gcctttgcgg taacaatctg gaaacacctt   1260
ttgtaacagc tatcggtcaa acgacagcca aaaataccta taccgaatgg cagaccgaca   1320
atcttgccag cgctaatgcc cagaataaac aggtcgaagg agctgatctt gccaatgaaa   1380
gccgccagcc aacggttcgg gtcggcaatt atacccagat catgaccaaa gttgtcggga   1440
catcgacgac cgatcgggcg gtgcataatg ccggacgcgg tgatgaacat gcctatcagt   1500
tggcacgtgc tggtcaggaa ttgaaacgcg atattgaggc gcgctttact ggtaattttg   1560
cagccattcc cggagatggg gcagtcgtcg cgcgtgaaac agcaggagct ttggcatggc   1620
tgcgcagtaa tgcccatcgt ggcgacggcg gtgccaatcc ggtgatgtcc ggtggcgaca   1680
atggcagcgg ttatccgaca acagcggcga ccacaggtaa ggcgcggctt tataccgagg   1740
ctttgttaaa agaagttttg ggcgatatct gggtcagtgg tggtcagcca aatatggtga   1800
ttacctcttt gaaactgaaa cagacagcgg cagcctttcc ggggttggct tccaaccggc   1860
gcgatacggg cgaccagaaa gcgcgtatta ttgccggtgc ggatatctat gtttccgatg   1920
tcggcgaagt ccagtttgta cctgatcgtt tttgcgacaa tagcagcgct ttggtcattg   1980
accctgaata ttggtcggtt gcgaccttag atccgattca gaaacggtct ttggcaacaa   2040
cggggctggc tgatcgtgat gccctttata ctgaaattgc cttgcgctgc cataatgaag   2100
cagcctccgg tgttttggca gatttaagcg ctgcctgatt ttcgtgatcg ggaggatgtc   2160
ttcttgcaag acatcttccc gtaaaaattc ggaaagggaa tattccatgg ctttttcttc   2220
tgccttggtc gcctttttca aaaaaaaggt cgggctgggc ttgaaatgcg gctttgatat   2280
tcgagggcat gatggctgct gaacgcttgt tatcctataa tccggtgacg gggcttaaaa   2340
gttggttttc ctcttcagag gagaatcagg gcagttggca tatccgctat gaacaggatt   2400
gttctgcggc tttggaagcc aataaacagg cacaaaatga agattttgat cggcgttctt   2460
cgatgtggca cgccgcccat gttccagccg tcgttttgat ggaatggctg gtgaaatatg   2520
gtgtccgata ttgggacaaa aatcacgcgc ctgccgttcg ccgtttactc aatcatcctg   2580
attatcgcta tttgcgcgtt aatcacttta ttatgtgagc atggctgatg gctcttttta   2640
ttgatgccca aaatctggac agtctcaccc gttatgatgg cctcttaaag gcgattgcct   2700
tgtggttgga acgcgatgat ctggccgatg aaatccctta tttcgtgcaa ctggcagaag   2760
cccgttttcg gcgattgttg actaatcccg aattggaaac cgaaataacg gtagcggcag   2820
gctgtcctgt tacgttgccg gatgattttg aggccttgcg cctgctttat ccggcaggcg   2880
gtcgtcgcga tcgggctttt ttgcagctgt cgccagatgt ttttcagcag ggcaagcatc   2940
agaataaatc tgttttcacc ctgatggcag ggcaattatg gatatcgcct cttcctgaaa   3000
cagaaacggc tttttcgttg gtctatcgtg cggctttgcc gtctttatcc ttgaatcgcc   3060
agagtaactg gctgttggcc tcccatcccg atatttattt attcgggtcg ttattacagg   3120
ccgagttctt cggatggaat gacagccgtt tgccggtcat taaatcggcg ctggatgaag   3180
```

```
ccttgggcga gttaaataaa gcaggattgc gcaagcgtta tgcagaaagc accttggttg   3240

cgccatcgcc tgtcgtggaa gcggtgaaag gcacttaccg                         3280


<210> SEQ ID NO 46
<211> LENGTH: 3008
<212> TYPE: DNA
<213> ORGANISM: Artificial Sequence
<220> FEATURE:
<223> OTHER INFORMATION: Nucleotide sequence of downstream of ORF
      ZMO0390 - ZMO0394

<400> SEQUENCE: 46

catccatttt ggatattatt tttaaattaa tccttaaaat gttggattta ttataagaat     60

atcacaatag atactttggg tatcgggatt ttttgtaagt aaaatccaat gtaatcgaaa    120

tgtaatcatt aaaatattta tttattttat gctcttataa ggaggggtag ggctgcgcta    180

tgtctttttc ggactggtcg caaaatgcag atagtaacag caatattggc gggatcagta    240

ttgctgaagg ctgtccaccg ggcaatctta acaatgcctt gcgcgagata atggctgaaa    300

tgcggtctgc tatcaatcag gctatggata cggccttgag ctcggctgat atggcgagtt    360

ttcgtcaggc tattggggct ttggcgaata gtggtgacac tattgacggc gttttgcgcc    420

gtaaaggtca gggggttttc ccttattttg ccgatggttc tttttccggt ggccggattt    480

atgtgaccaa tagtcaagcg gctgacccga caagtcagcc gggggatatc tggttggtct    540

atgtatgact atcagcctta aagatcagga taatttttcc cgcgagataa gagctgtttc    600

aatcagggga gccgatggcg tgcttcattc tgtcggatct attcgtatcc gtgggcagga    660

tgaaagcttg catgaggtct tttgccacaa gctggatgtc tcggtttctg acgctttgat    720

agaaagctat tcccgtcata atcctgtgat ttcttctgcg gtgacggttc aggtttcggg    780

cggtgttccg ccttatcaac atcgctggtc tttggtgagt agcgatagag ccgatagcgt    840

gatggctctt tctccttttt cggcaacaac gacttttcga gccgatggcg tgcctcatca    900

ccatgccgca tcagcctatt tgcgtgacga tgttaccgat cagaatggct ttgccggttc    960

ggttgaagtc cattgtattt ttacgaggta atttcatgcg taaatatttt gacagcgtgg   1020

cgagcgcgct tgacgggaag ccggtcatgg gtgccttgat tttcgtctat aaaacagacg   1080

gtagtctggc ttcccttttt tctgatgatg gaacgaccgc tatttcccag cctttgcgga   1140

cggatagtct cggatatttc gaattttatg ttgcggatgg tctttatgat ttgaccattt   1200

cctatggcgg caaaattcgg acgcgccttt ctggcgttca aatttatgat gaatcccatc   1260

tgcaaggggg cggggcagcc ttgcccgacg gcacccgtat tgccgaattg ccggtcgcag   1320

ccatgaacaa ggctttgggt gcggccggaa acttagccca atttatcaaa aactattcta   1380

ataattctat ggagtgatgc catgtctact ttaacgattt cggaaatgac cgatgcagga   1440

tcggttaccg aagatgattt gattgaaatt tcccgtccgg ttgccaatgg ttatgcaacc   1500

tataaagcca aaatcggcta tattaaaaat ctgacgacca attatgattc cgtcattgcc   1560

gctttggggc atgaaccggt gagcgttgat ttaagcaatt ttaacgccgc aactttccag   1620

cagaaagtag cgatttctta cggccagatt accaaaggcc tcggctatga gccgatgaat   1680

gtcgatttca gtaatttcaa cggatccact ttccagcaga aagtgacgct gtcctatggc   1740

cagattaccg gtggtctggg atatgaaccg gccaataaag acttgtctaa tattgatggt   1800

atgggtctgg tttcaaaaat caatgctgtc cgaggtgctg caccggtttt gacgaccggg   1860

ggtgaactga ctggtaatct caatccggct tcagatggtg tgattacctt gggacagccc   1920
```

aaccgaaaat gggctgaaat ctatgcttcg aatggggcaa ttaacacctc ggatgcccgt 1980
cagaagatgg atattgcttc tgtccctgat gaggttctgg atgtctgggg caatctgtca 2040
tggcggcagt ttaaattcag aaaagcggtt gagaccaaag gctttgataa ggcgcgctgg 2100
catttcggtc tgatcgctca agaagtcgaa gatgcctata aaaatgcggg cttggatgcc 2160
gaaagtctgg gcatgatttg tcatgaccat tgggaagccc atactcgccg tgaaaaaact 2220
ggtaatatgg gtaaaaatgg caagccggtc tatcgcgatg tcttggtgcc agccggtgaa 2280
gcctatggtt tgcgctatag cgaatgtcag gcgatcgaag ccgcatggca gcggcgtgaa 2340
atcattcggc agcaggctga aattgacgct ttgaaagcgc agctcaccca agcacaggct 2400
taagataatg acagcttctc cggcaccttt tattcctgac catcctgata tctatctgct 2460
ttccggcgat gggctggttc gcaataacat gcatgtcgaa gacgggcggg caggctatct 2520
gcctaatgat acttcgacca gtgaaagtca ggctttgtta gcgcgtggat atgcccgtta 2580
ttatctcgct tcgggggata taaaagccct caataatgct cgaaaattgg cggacgccgc 2640
attgagttac ttctttgccg gaaaaacgcc ccctgcaagc gggttatggt atcatcattg 2700
ggtggtgaat gcagggcagg gctttaacgt caaaggcccc tctaatccca atggtcatgc 2760
ctatgacggg aatgtcggag aaactgttac ctttaaggac gggaaggctc aacttcccgc 2820
cagtcttgcc aatgtttata atgtttttca gggagaacta agctggcaaa atgtctatgc 2880
cgatctatcc aaagggcagt tttttgatat agattatttt gttgatcgtg atggctatat 2940
tttccgctgg caaagcggat atgcggcgga tgttgttttt acatcggagg cacagcctca 3000
gaccgcta 3008

<210> SEQ ID NO 47
<211> LENGTH: 32
<212> TYPE: DNA
<213> ORGANISM: Artificial Sequence
<220> FEATURE:
<223> OTHER INFORMATION: 390F

<400> SEQUENCE: 47
atgatccgat ggctggaaat aatgcggata tg 32

<210> SEQ ID NO 48
<211> LENGTH: 29
<212> TYPE: DNA
<213> ORGANISM: Artificial Sequence
<220> FEATURE:
<223> OTHER INFORMATION: 394R

<400> SEQUENCE: 48
tagcggtctg aggctgtgcc tccgatgta 29

<210> SEQ ID NO 49
<211> LENGTH: 33
<212> TYPE: DNA
<213> ORGANISM: Artificial Sequence
<220> FEATURE:
<223> OTHER INFORMATION: del 394F

<400> SEQUENCE: 49
catccatttt ggatattatt tttaaattaa tcc 33

<210> SEQ ID NO 50
<211> LENGTH: 31
<212> TYPE: DNA

<213> ORGANISM: Artificial Sequence
<220> FEATURE:
<223> OTHER INFORMATION: del 390R

<400> SEQUENCE: 50
cggtaagtgc ctttcaccgc ttccacgaca g 31

<210> SEQ ID NO 51
<211> LENGTH: 3450
<212> TYPE: DNA
<213> ORGANISM: Artificial Sequence
<220> FEATURE:
<223> OTHER INFORMATION: Nucleotide sequence of upstream of ORF
ZMO1786 - ZMO1789

<400> SEQUENCE: 51
accaaagccg aaaaaaggtc atcaaaaata cctttggcag caagaccaat cgcgatacca 60
ccgataccaa gaccggcaac caatccagtg acattcacac ctagattatc gagaacgaca 120
acagaggcga tagcgaagag agccaccgtt acaagaagcc ggataagatt aagcgcgcta 180
tccaaattgc ggttgctatt attcgattgc tcgacccgat agctaatgag tcctaaaatg 240
agctgacgcg cccaagtcgc aaattggaaa gtgctggcaa tgacccataa gaactggaca 300
acatccgaaa ggcgcgagct atggtcaaaa tatgcggtga ccaatcgaat ggtcagaata 360
gccaagaaaa aagcatgagt ccgaccaatg gcttcaccgg caagagtcgt ccattcactt 420
aaaaaggcac tgcgcttcaa aaaattttcg gcaaagcgtc taaaggaaag caaagcgaaa 480
aagagaacaa cccctacccc aatagcgcag agtagctgga tataatgtcc taaaaaccat 540
tcactgattt gatggttcaa agcggctatc tcctgaggcg aagtcagaat agcggcatga 600
ttttgttcct gcattctttt tcctgaaaaa aattatccgg taaaatcagc tttcaagtga 660
aggaatattc acgttagaaa atctttatca cagcaggata atagattttt tcttaaatac 720
gccagaatgc aatgttaatt atttaatcgt ttttatccgc tagacttata gaattgattt 780
tgtcggataa aatctatgga gaaagctgaa atggcaggct caacgccaat ggaaggaaaa 840
aaggaaaaac gtcttatcgt tctttcttcc gctatgtttt ctatagctgt catttttttc 900
tggatggcta tgccgcctga aatttttacc cgactgaccc atgatactgc cattacttgg 960
ctgacaggag aggacggcag tgcgccttta ttatccagag cgcggctggc ctttcccctt 1020
ggtattgttt taggcgggat tatcgccttc atcgaacagt tctgactaga agaaaattaa 1080
agttaaataa agcatagcat ctaaatacta ttgagtttta aaaattaaaa tttctaatta 1140
ttttttgata tatcactcaa atattgctct actagaatat gagtgatact agcatggctt 1200
taattttatc tgactaattg agcttggtaa atcaagagat aatggctatc atatctatcc 1260
cagtgaacac gctatggaat cgtctaaata aagcggcatc aacatcttcc acggcgttgt 1320
ttgcaattat taccggatgt tatgcgcctt atctcggatt gctagctatt ctagcaattc 1380
ctttcggtga tattgttacc gcatcatgtc aatgggattg ctactggtat cttgatatca 1440
gtcggaatgg ttattcatct tttcccttga ttgttaaaaa tgctattggt gaagcaaact 1500
gggcattctt cccgctttac cctttacttg tgcgtgaagc atctgggata acaggcattt 1560
cagtcgagaa tatggcattc ttattgaatg ctttaggatt tccagtagtc atttttatgg 1620
cagtgaagac tcttattaaa cgagatctta cgcgcgagcc gattgcatgc atactgattt 1680
ttttactctt ccccttttaat gtttggtaca cagctcaata ttcagaatgt atctatgcgt 1740
taataatact tgtttatact agtgctattc ataaaaatca gattagcacg gcagcattct 1800

-continued

```
ccagtttttg tcttgcttta acccgtccaa caggattaat tgtgtcaatt gctggttcag   1860

tctggcaaat atttttttca agaaaggaaa tactttctag tcgatttgca aatgctattc   1920

ttatcatagg atgtgctggc tttgcggtat caatctttgc attacatctt caccatgtaa   1980

tgggtgatgg tttagccttt gctcatgtgc aaattgcatg gaaacgccat tccagcatta   2040

tatttgttca tatcattcgc tttatgacaa agttgcaccg aattcctttt cttatctatt   2100

tcattatgtc atgttttctt cttaaagaaa tggcaagaga cgccaaatgg cgacttgaat   2160

ttattatttt gctttcaacg ctactaattt ccgtaacaac cagccttatt tctattgaaa   2220

gaattatttt tggaaaccct ttggctatac aatacattgc cacacgcttg accgatcgat   2280

ttaaaaatcg cctgccgcga ctcctcatca tattagcaat cattcacacc cttgggaccc   2340

ttgcgtggta ctgtggatac agggtactgt tgtaatgcgg cgtacagtaa ttataataaa   2400

ggccaccata gggttattgc tggtcttatt cgatgcttat agctttttta cttgcaaatc   2460

tgctcaagta aacagctgct accgacaata ttatctcgaa caatcgataa acgccgcctc   2520

ttttgcgcgc tgtgaacaaa aaatgctgcc gccagaggag gtcaaaaacc aagcaaagca   2580

gaatccttcg cggtagcctt agtatccttc cagctgatca aatcgccctt catgaagggc   2640

tgatcaaaga taatcaccaa agccgaaaaa aggtcatcaa aaataccttt ggcagcaaga   2700

ccaatcgcga taccaccgat accaagaccg gcaaccaatc cagtgacatt cacacctaga   2760

ttatcgagaa cgacaacaga ggcgatagcg aagagagcca ccgttacaag aagccggata   2820

agattaagcg cgctatccaa attgcggttg ctattattcg attgctcgac ccgatagcta   2880

atgagtccta aaatgagctg acgcgcccaa gtcgcaaatt ggaaagtgct ggcaatgacc   2940

cataagaact ggacaacatc cgaaaggcgc gagctatggt caaaatatgc ggtgaccaat   3000

cgaatggtca gaatagccaa gaaaaaagca tgagtccgac caatggcttc accggcaaga   3060

gtcgtccatt cacttaaaaa ggcactgcgc ttcaaaaaat tttcggcaaa gcgtctaaag   3120

gaaagcaaag cgaaaaagag aacaacccct accccaatag cgcagagtag ctggatataa   3180

tgtcctaaaa accattcact gatttgatgg ttcaaagcgg ctatctcctg aggcgaagtc   3240

agaatagcgg catgattttg ttcctgcatt ctttttcctg aaaaaaatta tccggtaaaa   3300

tcagctttca agtgaaggaa tattcacgtt agaaaatctt tatcacagca ggataataga   3360

ttttttctta aatacgccag aatgcaatgt taattattta atcgttttta tccgctagac   3420

ttatagaatt gattttgtcg gataaaatct                                    3450
```

<210> SEQ ID NO 52
<211> LENGTH: 3100
<212> TYPE: DNA
<213> ORGANISM: Artificial Sequence
<220> FEATURE:
<223> OTHER INFORMATION: Nucleotide sequence of downstream of ORF
      ZMO1786 - ZMO1789

<400> SEQUENCE: 52

```
tatctcgctt gcaataaaac atattttcag gcttttcagc gcaagccggt tttaaaggga     60

ctcttcataa atatctttat cgaaggggca aaagaatcag ggataaaatc gtgaagcaag    120

cgacaaaagc aacgccgaaa aagagaaaga cgcttggcca gctccgaatg ctttggcaat    180

ttgccagccg ttatccgata tggattttcg gggctctgtt ggctttgctc ctttcttcga    240

cagcaacgat tgcgatacct gccgctttca aaatggtgat tgatcgcggt tttggcggcg    300

atagtggcgc ccatgatatc aatctttatt tttgctatat gctgggcatc attcttttac    360
```

-continued

```
tggcgcttgc aactgctgcc cgattttatt gtgtttcatg gttgggtgag cgggttattg    420
ccgatattcg gatggctatc agccgccatt taatgcaaat gccccctgct tttttgaag    480
agaatcggcc ttctgaaatt gcttcccgct taaccactga tacgactctg attgaccaga    540
ttgtcagttc tacggcgtcg gtcgctcttc gtaatttgat tactggcctt ggcggcaccg    600
cctatctttt tatgctggcc cctcatttaa ccgccatgtt gttgggcggt attccgattg    660
tggtcttccc tattattttt atcgggcggc gattacagcg attgtcccga aaaagtcagg    720
atcggatagc tgatctcagc agcctgatta ccgaaacctt gggcgcgatg aaaattgttc    780
aggcttttgg tcaggaagat cgggaatccg accgttttgg tcaggctgtt caactcactt    840
ttgagacagc aaaaaaacgg attacgctgc gggctttcat gaccgctttg gtcattttgc    900
tgatttttac ggcgattatc ctgattatgt ggcgtggtgc gctagatgtc gccgcgggtt    960
tggtgtcagg cggcaccatt gctgcttttg tgctgacagg cggggtcgtt gccggtgcgt   1020
ttggtgcgtt aagcgaggtc tatggtgatt tacttagggg tgccggtgcc gccagccgat   1080
tgaatgatct gctcgctgaa aaaccggcta ttctttctcc tgctcatccc aaggccttac   1140
cccacagcac agagggatgt ttaacttttc aggatgtctc tttccgctat ccctcgcgtc   1200
ctgatacaga agccttaagc cattttagtc ttgaactgaa agccggcgaa cggctggctg   1260
tcgttggctc ttcgggtgcc ggaaaaacaa cattatttca gcttatccaa cgcttttacg   1320
atccgacatc aggcgtgatt tctatggaag gtgtggattt aaaagaagcc gatttaagcg   1380
atatccgctc tcatatcgcg gttgtgcccc aagaaacggt tatttttgcc gcctctgccc   1440
gcgacaattt aagatatggg cgatgggatg ccagcgacga agagctatgg caggcggctc   1500
gtgcggctca tgccgaagaa tttttaaaag cccttccaga aggactggat agctttcttg   1560
gtgaaggcgg cgcacgcctt tcgggggggac aacggcaacg gattgcaatt gcccgcgcta   1620
ttctacggga tgctccgctg ttactattgg atgaggccac ctctgcactg gacgcagaat   1680
cagaacaagc ggttcaacag gctttagaaa aactgatgaa aggacgtagt tcgatcatca   1740
ttgcccatcg tctggcgact gtccgccatg cggacagaat catcgttatg gataaaggta   1800
agattgtcga ggaaggcagc catgaccagc ttatccaaaa aaatggtctc tatgcccgtc   1860
tcgcacagct ccaattcagc gatcagaaaa tagcttaatt actcattcaa aaaaacatga   1920
ccaataaaat aatcgggtaa ggcgtgaaac ttctttcaaa tttacagcga tctgccagca   1980
tctcataatg ctggcagaac aggctgataa ctttaacgcc gttcgagctg attgacatct   2040
cgaactgccc cacgggcagc gtttgtcgtc aaagctgcat aggctttcaa agccgaagaa   2100
atcggacgat tacggttttg cggtttccat gctgccgccc ccttggcttc catgcgggca   2160
tgacgatcgg caataacagc atcatcaaca tccagatgga taatccgttc aggaatatcg   2220
ataacaattg tatcaccggt ttcgaccaaa gcgatcaagc cgccctcggc cgcttcagga   2280
gaaacatggc cgatggataa accagagcta ccaccagaaa aacgaccatc ggtaatcaga   2340
gcgcagagtt tacccaaacc tttcgatttc agatagctgg tcggatacag catttcctgc   2400
ataccggggc cacctttggg accttcatag cgaacgatca ccacttcacc agcttcgaca   2460
tcattgccaa gaataccggc aacggcggct tcctgacttt cgtaaacctt ggctttaccg   2520
gtgaatttca gaatagactc atccacaccg gcagttttga caatactgcc ttcaggagca   2580
agattgccaa ataagacggc cagaccacca tccgtcgaaa aagcatgatt tttagaacga   2640
atcacacctt tttcgcggtc agtatccagc gcttcatagc gagaagactg gctgaaagcc   2700
ttttgagtcg gaacaccccc cggagccgcg cgatagaata actgcgcttc ttcagaacaa   2760
```

-continued ctgtcacggc tgatatccca tgcgtccaat gctgcgccta aagtcggaga atgaatggtg 2820
cgcaagctgg tattgatcaa tccggcacga tcaagctggc ctaaaatggc cataacgccc 2880
cctgcccgat gaacatcttc catatggaca tcatttttgg ccggtgcgac cttgcataag 2940
caagggacat gacgggaaag acgatcaata tccgccatag tgaaaggcac gttgccttcc 3000
tgcgcgaccg ccaacagatg caaaaccgta ttggtggaac cacccatggc gatatcaaga 3060
ctcatcgcat tttcaaaagc ctcaagcgtg gcaattgaac 3100

<210> SEQ ID NO 53
<211> LENGTH: 32
<212> TYPE: DNA
<213> ORGANISM: Artificial Sequence
<220> FEATURE:
<223> OTHER INFORMATION: 1786F

<400> SEQUENCE: 53
accaaagccg aaaaaaggtc atcaaaaata cc 32

<210> SEQ ID NO 54
<211> LENGTH: 34
<212> TYPE: DNA
<213> ORGANISM: Artificial Sequence
<220> FEATURE:
<223> OTHER INFORMATION: 1789R

<400> SEQUENCE: 54
gttcaattgc cacgcttgag gcttttgaaa atgc 34

<210> SEQ ID NO 55
<211> LENGTH: 31
<212> TYPE: DNA
<213> ORGANISM: Artificial Sequence
<220> FEATURE:
<223> OTHER INFORMATION: del 1789F

<400> SEQUENCE: 55
tatctcgctt gcaataaaac atattttcag g 31

<210> SEQ ID NO 56
<211> LENGTH: 31
<212> TYPE: DNA
<213> ORGANISM: Artificial Sequence
<220> FEATURE:
<223> OTHER INFORMATION: del 1786R

<400> SEQUENCE: 56
agattttatc cgacaaaatc aattctataa g 31

<210> SEQ ID NO 57
<211> LENGTH: 4879
<212> TYPE: DNA
<213> ORGANISM: Artificial Sequence
<220> FEATURE:
<223> OTHER INFORMATION: Nucleotide sequence of upstream of Lactate
dehydrogenase (ZMO0256)

<400> SEQUENCE: 57
tggcagtcct ccattcagat cgaaggtgcc agccttgacg ggaaagaatt gccagtcaaa 60
gagctcccga cattacagcc gccacgctgt gtcaaaaata ccgaaaacaa accgatgacc 120
ttctttgcct attcggaaga ccccgaatgt cagactttat cgcttaatgc cggaaaaggg 180
caggtgacta tgtcgggtgt ttgtcagaaa aatggtaaaa atctgacaac cattgaagcc 240

-continued

```
aaaggcgact atcacctccg cgattattct atggcctata ttatgcgaag tgaagaaaac    300
ggccataaat tagaagtccg tggacatatg tctgggcatt ctatcggctt atgccctgcc    360
aaagatagca atgccgatga tatcaccttg gggaacaaaa accactaata cgggtgttcg    420
tttggcgata agactattta gcaatcatag gcttccgtca taaccgctaa aatcatggca    480
gggatcgacc ttacggactt cttccatgcc tttctttgat agcaaggcat tgtaggggca    540
tatcggggca aaatatatcc cgatcacaag ggcgaccttt gtaggacag atatgcctaa    600
aactctaatg acgacaggcg taaaatccta aagactttcc gtttccgata tctgatttat    660
catttttct gatgagtagt tgctgcgtcc aattcgctga tttcaggatt ggagtcaggt    720
cagggtataa ccctataatg atagctacgg gatagaacgc ttatcatcag cttctatctt    780
tgtggcagat tcctgtcgca gggaaagata gtgcagaagc tatcttgacc atatccctgt    840
catgatagca ccccgttcca gatgccagat gccagatgcc agatgccaga tgccagatgc    900
cagatgccag atgccagatg ccagatgcca gatgccagat gccagatgcc agatgctcga    960
attatatctg gcaaaaccct ctcacagaaa aagggcatca cccctcaatc gcagacccga   1020
aatagatctg acgcagacat taaaaaaggc caatggaaac ccattaggcc tttttttattc   1080
tatcaggaaa ggatccggtt aaaaccggat acccttatta accctgacgg gctttaaagc   1140
ggcgaaccgt tttattgatg atataagtgc ggccacgccg gcgaatcacc cgattgtcgc   1200
gatggcgccc ctttaaggat ttgagcgagt tgcggatttt catggccgga ctacctgcct   1260
tcatcttaaa aattgggaaa gaaaatgagg cctctgccta tgcgctgaat tattataagt   1320
caaggaaaat tctgatatat cggaaatatc cttgaaagaa aaatccgata tctcttcatc   1380
aaaacagcca aagaccattg gaatacaggc tttttcgtt actttttca cgattacaaa   1440
aaaggctata attcttttt gaaatattat gatatccgtt aaagatcata gccacagcaa   1500
ccacccttca taaccggatg gcttgacgga gactatcttg aggcatctca tcacgatatc   1560
acagcccgca ataccgcaag acgtgaccaa taaagacggt cacaaggcaa aaaaacagct   1620
ccggtgcaaa ggcatctatc ccttttttatg gatgttttc tttgcggcgg cgcttccgtt   1680
acaggcgacc cagccgatag aagtcactcg ctttcacaaa agcgatatgg ctacaaccgg   1740
catcgtcaac attatgcctc atgacccgac cttacggaat acgctggaat atcagcgcta   1800
cacggccagc atcgcccgca atctcacaag aatcggtttc caagtcacgg acaacccgca   1860
acaagccgaa tatacgatga tgtatgacgt gatgcgggga acgcattaca gagacaacgg   1920
ccaaacgccc ccgcgtgata ctcgccctca tggtggcatc agccttggcg gtggttatgg   1980
tggcggaggc ggctttggag gcggcggtgt cggctggggc ggcggcggaa gtggtatcag   2040
tatcggaggc ggtggcgggg gtggccgcgg cttcggaggt ggcggaggcg gtatcagtgc   2100
cggtatttct gtccctgtcg gtaacggcta tcataccagc aacaaggtcg aaaccattct   2160
aacggcacaa ctcagccgca gggatacgca tcaggctatc tgggaaggcc gcgcccgaac   2220
ggaagctaaa agtaacaaag ccgaaagcac gcccgatatt gcggtggaca gattagccac   2280
agccatgttc ggccagtttc ccggtgaatc aggtgaaacg gaaaaagtaa aatgaccctt   2340
caaatcaatg ccgcctttga tggcggaaat atccatgttg tcgaacaaga cggaaaccgg   2400
atttatctgg aaattatcaa agataaccag tcggatttct tccaatggtt ctatttcaag   2460
gtaaccggtg ccaaagatca ggccttggaa ctggttgtca ccaatgccag cgattccgcc   2520
tatccggccg gctggcctga ttatcaggct cgcgtttccg aagaccgcca agactggcaa   2580
```

-continued

```
atgacagaaa cggattatcg cgacgggatg ctgaccatcc gttatacgcc gcgtagtaat   2640
atcgcttatt ttgcctattt cgccccttac tcaatggaac ggcaccatga tctgattgcc   2700
cgtatggctg gcaagtcagg ggtcggttac gaaatgttgg gtaaaagcct cgatggtcaa   2760
agcatggatt gcctgacgat gggggaaggg cggcgctcta tctggttgat cgcacggcaa   2820
catccgggcg aaaccatggc cgaatggtgg atggaaggcg ctttggaaag gttaaccgat   2880
gaaaatgact cggttgcgcg cctgcttcgc caaaaagccc gctttcatat catgcctaat   2940
atgaatccgg acggttcttg ccgtggtcat ttgcggacga atgcttgtgg tgccaatctc   3000
aatcgtgaat gggcagaacc cacggctgaa cgcagccccg aagtgttgga cgttcgcaat   3060
catatggaca aaacgggcgt tgattttgtc atggatgttc atggcgatga agctattccg   3120
catgtattcc ttgccggttt tgaaggtatc cccgatctcg acaaggcaca ggataaatta   3180
ttccgccgct accggaataa attggccaaa tacacgcccg attttcaacg tcattacggt   3240
tatgaaaatg acgagccggg gcaggccaat ctagccttgg cgactaacca attagcctat   3300
cgttacaagg cggtttcgat gacgcttgaa atgcctttca aagatcatga cgatatgcct   3360
gatttgaaaa aaggttggtc accggaaagg tcaaaacaat taggccgcga ttgtctcgct   3420
atcttggctg aaatgattga tcagctcccg atctctggca aagatctcgc gtaataaaac   3480
tatcaggcgc aatcgtaatt ttgcgtctga tagagctttt cataaaggct ataaccgcta   3540
ttgccaaaag ccataggcct gcataatctg acggcgaata attttcctga aagattggcg   3600
gccatttttg ctgaccgcac agattgtcag cgttaattat acatggcttc ttttgttgat   3660
tcgggaactg caagcgttta ccggaacaac acataacgaa gagatattga aaaggagtgg   3720
aatatgccca cgctcgtttt gtcccgtcac ggacagtccg aatggaacct tgaaaaccgt   3780
ttcaccggtt ggtgggatgt taacctgact gaacagggtg ttcaggaagc aacggccggt   3840
ggtaaagctc tggctgaaaa gggttttgaa ttcgatatcg ctttcaccag cgttctgacc   3900
cgcgccatca aaaccaccaa tcttattctc gaagccggta aaaccctttg ggttccgacc   3960
gaaaaagatt ggcgtttgaa tgaacgtcac tatggtggtc tgaccggtct gaacaaggct   4020
gaaaccgccg ctaaacatgg tgaagaacag gttcatattt ggcgccgttc ttatgacgtt   4080
ccgccgcccc cgatggaaaa aggcagcaag ttcgatctgt ctggcgatcg ccgttatgat   4140
ggtgtcaaga ttcctgaaac ggaaagcctg aaagacaccg ttgctcgcgt gctgccttat   4200
tgggaagaac gcattgcccc tgaactgaag gctggcaagc gcgtcctgat cggtgcgcat   4260
ggtaactcac tgcgcgctct cgttaagcat ctgtcgaaat tgtcggacga agaaatcgtc   4320
aaattcgaat tgcccaccgg tcagccgttg gtctacgaat tgaatgatga tctgactccg   4380
aaagatcgtt acttccttaa cgaacgttaa tagccttggg cttttaaagc cttttggttt   4440
gttaaccgtt ttttcggcca gagttttctc tggccgaaaa tttatgtcta tccctttgtt   4500
tttctatccc catcacctcg gttttgttga caaaaaaagg tggccactaa attggctttc   4560
cgcaccgatg ggatgatttt tattctttgc tattcttcgc tctttgccca attcattaaa   4620
agcggaaatc atcaccaaag atagaagacg cagccttcac catttcagat tgcccttctc   4680
gggcattttc tgctgctaga atcctcttaa aaatattaaa ttccactcta ttggtaatat   4740
gtttccctct ttagggaaca aataaagccc ttctttgttc tataaaagtt agcttaccga   4800
ttttacaaaa aataataccg cttcattcaa tcggtaatac atatcttttt tcttcaaaaa   4860
acttttcaag agggtgtct                                                4879
```

<210> SEQ ID NO 58
<211> LENGTH: 4984
<212> TYPE: DNA
<213> ORGANISM: Artificial Sequence
<220> FEATURE:
<223> OTHER INFORMATION: Nucleotide sequence of downstream of Lactate dehydrogenase (ZMO0256)

<400> SEQUENCE: 58

```
tagacaagcg acaattaacc ttttgaagat cataatgatc aaatttttgg gttaattcgg     60
tagttatggc ataggctatt acgcgctaat tgatatcaaa aaaaagcata gccggacatc    120
ataccggcta tgttttttat taggaaaaaa tttcctttca ccttgcttag ccatcgccgc    180
attatttaat caatatgccg agtttttctt gaaatcccta tcttacacca aggccaacaa    240
gggaatcatc catactcggt gtcctatcct atgacttttt aaatttttctc caaatttact    300
aaaatcacgc catctcagcg gctgctattt tcaaaaagcg cctctcaaaa ccgctttttc    360
ctgctcaaat atcggatccc aaaattccct caaaaaaggc agggtatttt ttacaaaatc    420
gcccctaata tctctcaatc cgctgccttg ttcatatgtt tttgcaaatg atttttatta    480
aacttttttta ggcgtatttt tatcaagaaa atttaaataa tcacattttt attattttag    540
atttaagtat tgatacaagt gatatctata aatgttttta taactttctg gatcgtaatc    600
ggctggcaat cgttttccct atattcgcaa gatgtatgtc agccgcagat ttgtcgactg    660
acctctatct ctccgagata tatcaacaaa aggtagtcac catgaaagca gccgtcataa    720
ctaaagatca tacgatcgaa gtgaaagaca ccaaattacg ccctctgaaa tacggggaag    780
cgcttttgga aatggaatat tgcggggtat gtcataccga tctccacgtg aaaaacgggg    840
attttggcga tgaaaccggc agaattaccg gccatgaagg catcggtatc gtcaagcagg    900
tcggggaagg ggttacttct ctgaaagtcg gtgaccgtgc cagtgttgca tggttcttca    960
aaggctgcgg ccattgcgaa tattgtgtca gtggaaatga aacgctttgc cgcaacgttg   1020
aaaatgccgg ttatacggtt gacggcgcta tggcagaaga atgcatcgtc gttgccgatt   1080
actcggtcaa agtgccagat ggtcttgatc ctgcggttgc cagcagcatc acttgcgcgg   1140
gtgtaaccac ctataaagca gtcaaagttt ctcagataca gccgggacaa tggctggcta   1200
tctatggctt gggcggttta ggcaatctag cccttcaata tgccaagaat gttttcaacg   1260
ccaaagtgat cgcgatcgat gtcaatgatg aacagctcgc ttttgccaaa gagctgggcg   1320
cagatatggt catcaatccg aaaaacgaag atgctgccaa aatcattcag gaaaaagtcg   1380
gcggcgcaca tgcgacggtg gtgacagctg ttgccaaatc cgcctttaac tcggctgttg   1440
aggctatccg cgcgggtggc cgtgttgtcg ccgttggtct gcctcctgaa aaaatggatt   1500
tgagcattcc tcgcttggtg cttgacggta tcgaagtctt aggttctttg gtcggaacgc   1560
gggaagattt gaaagaagcc ttccagtttg cagccgaagg taaggtcaaa ccgaaagtca   1620
ccaagcgtaa agtcgaagaa atcaaccaaa tctttgacga aatggaacat ggtaaattca   1680
caggccgtat ggttgttgat tttacccatc actaggtttc cgtgaaggcg gaagcataaa   1740
cggaaaaagc ctttctctta ccagaaaggc tttttctttg tcgtctgata aaaattttca   1800
tacagaattt aatacagcaa tcggtgctat aagccgctat ccaagctttt ttcttctcat   1860
gccttctatt cggcaatcgc tatttaaagg ctgtttttat ggggcattcg ccctatatat   1920
aaggatatta gcgtttatat ataatagaag gaaatctggc cttgggtgaa acaaccctcc   1980
aagcagcgcc ccatgcccat attcaacata gcggctccga tttattggaa gcggccaagg   2040
cggctttatt gaaatcgggt gagcaatgga cagccatgcg tgcctccgtt tacaaagcct   2100
```

-continued

```
tggcacaaac caacaagcca agttcagcct atgatattgc cgatattgtc tctcaatccg   2160
aaggacgcag agtagctgcc aacagcgttt atcgcatcct cgacatcttc gtcagtagca   2220
atctcgcgca tcgggtcgaa agcgctaacg cctatatcgt caacgcccat cctgaatgtc   2280
gtcatgactg cctttttctc gtctgcgacc aatgtggggg tgtgattcat atagatgatg   2340
acaagatcag ccgcttttta aaagaatcgg cagaaaaaaa cgattttgtt gcagaaaggt   2400
ctgttttaga aatacggggt aaatgttcac attgtctttc ccattaacct aaatgtacct   2460
caggttaacc tgttgcaatg actctattac ctgctatgat tttgtaactt ttatgtcgca   2520
gtcagggctt atcttggcta atttgggttc ctgctgttca cctttagggc gaattgtttt   2580
actaaacagg cttaaatttc ggtttgattt aaggccctaa gcttatgttt ccgaatgaca   2640
agacgccgct gttagacaag atcaagacac cggcagaatt gcgtcaatta gatcgcaaca   2700
gcctccggca attggcggat gaattacgga aagagaccat ctcggcagtg ggtgtgaccg   2760
gcggacatct cggttccggt ctgggggtta tcgaattaac ggtagccctt cactatgttt   2820
tcaacacgcc caaagacgct ttagtctggg atgttgggca tcaaacctat cctcacaaga   2880
ttttaacagg tcgccgcgat cgtattcgga cattgcggca acgtgacggc ttatcgggct   2940
ttacgcagcg cgcggagagc gaatatgacg cttttggagc cgcgcatagt tcgacttcta   3000
tttctgcggc gctcggcttt gcgatggcca gcaaattatc cgacagcgac gacaaagcgg   3060
ttgcgattat cggtgatggc tcgatgacgg caggcatggc ttatgaagcc atgaataacg   3120
ccaaggcggc gggtaagcgc ctgattgtca ttttgaatga caatgaaatg tcgatttcac   3180
cgccggtggg tgccttatcg tcttatttga gccgcctgat ttcctcacgg cctttcatga   3240
atttgcgcga tatcatgcgc ggcgttgtta accggatgcc aaaaggcttg gcaacggctg   3300
cccgcaaggc tgatgaatat gcgcgtggta tggcaaccgg tggcaccttc tttgaagagc   3360
tgggctttta ctatgttggc cccgtggatg gtcataattt agatcagctc attccagttt   3420
tagaaaatgt ccgcgatgcc aaggacggcc ccattttggt gcatgtcgtc actcgcaaag   3480
gccaaggcta tgctccggct gaagcggcca aggacaaata tcacgccgtg cagcgcttgg   3540
atgtggtttc cggtaagcag gcgaaagcgc ccccgggacc tcccagctat acctctgttt   3600
tttcggaaca gctgatcaag gaagctaagc aagacgataa gattgtgacc attacggcag   3660
ctatgccgac tggcaccggt cttgatcgtt ttcagcaata ttttcctgaa agaatgtttg   3720
atgtcggtat tgccgaacaa catgccgtaa cctttgcggc tggtttggcg gctgccggtt   3780
acaagccttt ctgttgtctc tattcgacct tcttgcagcg cggctatgac cagttggtgc   3840
atgatgtcgc tatccagaat ttgccggtgc gcttcgccgt cgatcgtgcg ggtcttgtcg   3900
gtgccgatgg ggcaacccat gcgggtagct tcgacctcgc ctttatggtt aatctcccga   3960
atatggtcgt gatggcgcct tccgatgaac gggaattggc caatatggtg catagcatgg   4020
cgcattatga ccaaggcccg atctcggtgc gttatccgcg tggtaatggt gtgggtgtct   4080
ccttggaagg tgaaaaggaa attctgccta tcgggaaagg tcgcctgatc cgtcgcggta   4140
aaaaggttgc tatcctatct ctcggcactc gattggaaga atccttgaag gctgctgatc   4200
ggcttgatgc tcaaggtttg tcgacatcgg ttgctgatat gcgttttgct aagcccttgg   4260
atgaagcgct gacccgccaa cttttgaaaa gccatcaggt cattattacc attgaagaag   4320
gcgctttggg tggttttgca acccaagtcc tgacgatggc ttcggatgaa ggcctgatgg   4380
atgacggatt gaaaatccgc accctgcgtc tgccggatcg gttccagccg caagacaagc   4440
```

-continued aagaacggca atatgccgaa gccggtcttg atgctgatgg catcgttgct gcggttatct 4500
ccgcattgca tcgtaattct aaacccgtgg aagtcgtcga aatggcgaat atgggtagca 4560
tcgctcgcgc ttaatttgct attagggagc ctcggctccc gacaatagta aagagatcat 4620
atataatgct acatccggtt gttttgtgtg gtggttcagg tacacgtctt ttcccgttat 4680
cccgccggag ccatcccaaa caactcctca gcttgatggg cgaaaatagc ctgtttcagg 4740
acgctgtcgc acgtgtaaca gattcttctc tattcacggc acctcttgtt atctgcaatg 4800
aagaataccg ttttactatt gcagaacagt tgcaggaaat gggcgttaag gctcaagaga 4860
ttgtccttga gccagaaggc cggaacacag cgcccgcgat tgctttagcg gcgtcaatga 4920
ttgcagataa agatcctgat gcctgcatgc tgatcttacc gtcagatcac gttatccggg 4980
atgt 4984

<210> SEQ ID NO 59
<211> LENGTH: 29
<212> TYPE: DNA
<213> ORGANISM: Artificial Sequence
<220> FEATURE:
<223> OTHER INFORMATION: ldhAF

<400> SEQUENCE: 59
tggcagtcct ccatctagat cgaaggtgc 29

<210> SEQ ID NO 60
<211> LENGTH: 29
<212> TYPE: DNA
<213> ORGANISM: Artificial Sequence
<220> FEATURE:
<223> OTHER INFORMATION: ldhAR

<400> SEQUENCE: 60
gtgatctgac ggtgagctca gcatgcagg 29

<210> SEQ ID NO 61
<211> LENGTH: 36
<212> TYPE: DNA
<213> ORGANISM: Artificial Sequence
<220> FEATURE:
<223> OTHER INFORMATION: ldhA-PmeI-2F

<400> SEQUENCE: 61
aactagttta aacaagagcg aagaatagca aagaat 36

<210> SEQ ID NO 62
<211> LENGTH: 36
<212> TYPE: DNA
<213> ORGANISM: Artificial Sequence
<220> FEATURE:
<223> OTHER INFORMATION: ldhA-PmeI-2R

<400> SEQUENCE: 62
ctcttgttta aactagttat ggcataggct attacg 36

<210> SEQ ID NO 63
<211> LENGTH: 3656
<212> TYPE: DNA
<213> ORGANISM: Artificial Sequence
<220> FEATURE:
<223> OTHER INFORMATION: Nucleotide sequence of upstream of D-lactate
dehydrogenase (ZMO1237)

<400> SEQUENCE: 63

-continued

```
tgtttcaggg aaccggtatt ttaagtcaat taaaagccgc cagccatgct gtcgatgccg     60
cccatgcgcg gcaacaaacc gctttattgg aagcccataa caagctccgt tcgattcatg    120
cggcggcgat gggttctatg gcaagaatag gtgttctgca aagtcgtctg aaaaccatta    180
tcgaagcccg cgatctttat cgcgatcaat atcgtttggg ctctcgttct ttggttgatc    240
tgctgaatag tgagcaggaa atttatcagg cgcgcaccga aaatatcaat gcaaggcatg    300
atttgtgggt gagtgaagcc gatcaggtcg ccgcatccgg tcgggcaaga gccgtctatg    360
gcattgacca caccgtcgtt cagggattgg agatattgcc atgatggcgc agggtggaga    420
agaaaaacgc caatcccttc ttttatggga agcctggctg gatgccatga ttgcgattgc    480
ccgtcattat acccttccgg tttcagtcga gcatgttcgg aatatcatgt catgggataa    540
ggctgaatct gatgaaggtc gcctatccgt tatggcgcgt catttaggtt taggattccg    600
tttggaatcc ggcgaaaaag ccgaaggcgc cgtgcgttcg ggtgtcgcgt taccctttat    660
tgcccattgg gatgatggcc gtattggttg tgtgatgacc aatgatggtg acgggcattt    720
agcggttcgc ttttcgggcg aaggcgatct ggaaacgccg gttgaaattg actggttagc    780
cgatcacgtt attgaaatcg cttatttgcg gccattgcgc tctatacccg atgggcgggt    840
cgatgattat atccagcctt atcgtcccca ttggttccgc cgtttggcct tggctgattg    900
gcgacgtttc ggggaagtta ttgtcgcctc gctttttatc aacctttttgg ctttgtcttc    960
gactctgttt tcaatgcaga tttacgatcg cgttgtgcct gcccaatcag agccaacctt   1020
atgggttttg ttttcgggcg tgatgatggc ggtctttttt ggattactgt taaaggttgc   1080
ccgcacccga ttattggatg tgatcgggaa aaaagccgat ttgcggattt cagagcatgt   1140
ctttggtcat gcgatccgtc tggtttacga tgcccgtccg aaagtcgccg gtagttttat   1200
tgcccagctt cgcgaattgg aacatgtccg cgaattattg accgcgacca gtatcgccat   1260
gattaccgat ctacccttct tttgcctgtt tttaggtatt ttatggatgg ttggcggtaa   1320
tttgatttgg gtggcgttgg ccgctgtgcc tttgttgctt atccccggta ttctggtgca   1380
atatccgctt gcccgcctgt cacaacaggg aatgcgtgaa tccgctttac gcaatgcttt   1440
gctgatcgaa gcggttgatg gttttgaaga tattaaattg atgcgtgccg aacctcgttt   1500
tgaaagacgg tggaaccatg tccattcggt ggccgcctcc attgccatgc ggcagcgttt   1560
ctataccgga ttgatggtga catggagtca ggaaatccaa accatcattt atgccctgat   1620
tttattggtc ggctgtttcc aagtcatgaa gggaacgatg acaacgggtg ctttggtcgg   1680
atgttctatt ttgacttccc gcatgattgc cccttttggca caattagcgg gtttcttttt   1740
gcgttttcaa caagcacgcg ttgcccgtga agggctggat tctttgatga gccgtccggc   1800
ggatcgtgcg gatcaggcgc aattagtgca attacccagc attcgcgggc aatatcaatt   1860
tgaaggcgtt cgtttcctgc atgacccaaa atcgggacga cctgatctcg atattcctaa   1920
gctggttatc cgtcccggtg aaaaaatcgc cttattaggt cggaatggcg cgggtaaatc   1980
gacctttctg cggatgttat ctggcctcca tcagccttcc aatggccgga ttatgttaga   2040
tggtatcgct ttaccgacga tagatcccgc ggatttgcgg cgtgacattg gcttgatgac   2100
ccaagaagcc aaaatctttt atggtagttt gcgcgataac ctgaccatgg gcgcgccttt   2160
ggcgagtgat agtcaggttt tggcggcttt ggatatggtt ggattgaaaa ccattttgga   2220
tcagcgagcc gatggtctcg atatgttatt gaaagagggc ggtggtgaat tatccagagg   2280
acaacgccaa tcaatccttt tagcgcgttt gattttatca gagccttctg tcgttttatt   2340
ggatgagccg accgctcatt ttgatgaaat gtcagagcat catctgatta acaatctgac   2400
```

```
ccccttgggtg aaaacccgca gcttgatcgt ggcaacccat cgtcaaagta ttttgcgctg   2460

ggtcaatcgt attatcatcc ttgataaagg ccatatcgtt atggacggtg atcgggattc   2520

tgttctgaaa aggctgacca atggctaacc tttccttgtc cacccagagc atggtcgatg   2580

atcgtgaccc tttgcatctt ccggcacgga ttgtctgggt cgttgtggtg atgttgctgt   2640

gctttttat ttgggcagcc tgctttacgc ttgaagaagt ttcaaccgga acagggaagg   2700

tggtgccgtc ctcgcatgaa cagaccatcc aatctttaga aggtgggatt cttgtccgat   2760

tgaatgtcaa agagggcgat attgttcagg ccggacaaat gttggcgcag cttgatcgca   2820

cccgcaccca atcttcggtt gaagaaacgg ctgcgcgtgc tgtggccgca gaggcaacgg   2880

cggctcggtt gcgggcagag gtgaataata ccccgatttc ctttcccgat tctgtgaaag   2940

cctatcctgc tttggtgaaa tcagagactg atctttatcg ctctcgccgc aatagtttgg   3000

ctatgggatt gagcgatctt catcagcaat tggctttgat taaaaatgaa ttgacgatga   3060

ccgagccact ggtggcaagg ggggcggcta gtgatgtcga ggttttgcgt ttgaaacggc   3120

aggtaagcga aatcgacact cgcgccgatg atatgcaaaa tcaatatatg gtgaaggcca   3180

gagaagacct tgaaaaagcc gaggcagagg cgaaagccca gcaatcggtt acgaaagggc   3240

gttctgatat gttagatcgc ttgaccttta cttcgcccgt aaggggcatc gttaaggata   3300

tcgaagttac cacgaaaggc ggcgttattc cgcctaatgg tcgtttgatg acgattgtgc   3360

ctttggatga acaattattg gtcgaggcac ggatatcacc tcgggatatt gcttttattc   3420

atcccggtca gcgggcaacg gtcaaattga ccgcctatga ttacgctatt tatgggggct   3480

tgcctgcaaa agtgacggtt atctcaccgg ataccgtgca ggatgatgtc aggaaagata   3540

gctattatta tcgcgtctgg gtacgcacgg attccgatca tctaaccaat aaatctggcc   3600

ataaatttcc tattgttccc ggtatggtgg caacaattga tattcataca ggatca        3656
```

<210> SEQ ID NO 64
<211> LENGTH: 3848
<212> TYPE: DNA
<213> ORGANISM: Artificial Sequence
<220> FEATURE:
<223> OTHER INFORMATION: Nucleotide sequence of downstream of D-lactate dehydrogenase (ZMO1237)

<400> SEQUENCE: 64

```
tttcttttgc agtgttctgt cagcctgaaa atatctataa tagctgtttt caggttgcct     60

tttcctaacg catgcaaccg aaaacgaggc ttggggttta gccttgcaag aataaaaaga    120

aggaagcgag aaagagaacg gtatgcgcgt tttaatcgtt gaggatgagc cgacgctttc    180

ccgtcagttg cgaacaactt tggaaggggc tggctatgct gtcgatctgg cgacagatgg    240

cgaagatggc catttcctag gctcgagcga aaattatgat gccgttgtcc ttgatctcgg    300

tttgcccgaa gtcgacggtc tcaccgttct tgatcgttgg cgcaaagaag gccgcgaaat    360

gccagttctg gttctgactg cacgggatag ctggtctgat aaagttgctg gtcttgatgc    420

tggtgctgat gattatctga ccaagccttt ccagaccgaa gaattgattg cccgtttgcg    480

ggctttgatc cgacgggctt ccggtaatgc gtcttctgaa ttgacggcag gtgatgtccg    540

gcttgacact cgttccggca aagtgacttt agcgggtgag cctgtcaaat tgacggcgca    600

ggaatataag ctgctttcct atctgatgca tcataaaggc aaagttgtca gtcgcaccga    660

aatgatcgag catatttacg atcaggattt tgatcgcgat tctaatacga tcgaagtctt    720

tgtaacccgt attcgtaaga aactggggca ggatgttatt acgactattc gcggtttggg    780
```

-continued

```
ttatgctttg aacgacccag aggatcggaa taacggctga ttatggcttc cgcttcttcc    840
cctagcggtg gccgaaagcg ttttttagt cgtttctttc gccggaaaaa aatcgaaaaa    900
agcggaaatc cggtcggaga aaataacagt caggagccgg taatacgtcc taccggttct    960
ttgacccgcc ggttgattgc tatttcggct ttgtggatat ttatcctgct atcgggcggc   1020
ggcgtaacct tggatcgggt gctgacccaa gccgtcaccg ataattttga cagccagctt   1080
gattatgttt tggcggcgat gatcgcttct tctgaaattg atcccgaagg ggcggttcga   1140
ctgaatcggc ctttgggtga ccagcgtttt ttggaagccc atagcgggct ttattttcag   1200
gtgagcggta gcggatatga aagatttccg tccccttcac tttgggatcg ctcgctacaa   1260
gtcaatccga tgcctaaagg gcaattggtg cggacatatg atagcgacga attttctgat   1320
ggcactttgc gagtgatgga acgggatgtc cgcttacccg gttcgtctgt tttatggcga   1380
ttccaagtcg ctgaaattcg tacttcttta gacaatcaga ttaaaaaatt acgccatacc   1440
cttgtgaaag cctttttgat tttaggcacg gggttgattg ttattaccgt tttacaggtg   1500
acgatcggat tatggccgct gcggaaatta aggcgcgaga ttagtgctgt ccgtaatggt   1560
caggcttcgc gtattcatga ccggatgccg aatgaagtcg ccccttttgat tgaagaattg   1620
aacgctttgt tgtctcataa cgaacggcaa gccgaagagg ctaggcgaca tgctggtaat   1680
ctggctcatg ccttgaaaac gccattaacg gttgtgacta atgaggcgaa tgccaatagc   1740
gatgccttga aagaagttgt tttgcgggag gtgatgacca tgcggcggca tgtcgatcat   1800
catttggcgc gagcgcgggc tattggacgg cggggcaatg cccaaagcca agcagaggta   1860
tggcctgctt tactggcggt agaacgcgcg gttactcggc tttatcctca tgcaacgatt   1920
gatcttgcag gagttaagga cgctgttgtc agaatagaaa gacaagatct ggacgagatt   1980
ttgggaaatc ttatagaaaa tgctgctaaa tatggtcagg gacgcgtttt tgttacggta   2040
gaaaaacagg gtaagtcggt tgaaatcctg attgaagatg atggcacggg tattcctgaa   2100
aatctccgtg ggcagttgtt taaacgcggg gcgcgtttgg atacagataa acccgggact   2160
gggttggggt tggcaattgt tcgcgatgtg gtcgaaattt atggcggcag tgttactttg   2220
gaagaaagtg aagatttagg tggcctgttt gtccgtctgg cattgccatc agtacattaa   2280
attcacgatt tgatgggatc cgcataaagg gttttgcata gccctgctat ttgtctgttc   2340
tgatagacaa agtattattt tgaaacggta tctttttgct ctcttggttt ttctgtggcg   2400
ttaaagtgct ttagcttggg gtagtgtgaa gacatagatt tttgatattg ttttctatcc   2460
ctttgacggg atcttgttgg ggagaaaaag gctgtccgat ttcgggaatg caaggctggc   2520
gtgtcatgac gtgagttgtt tgagaggcga ccgcttactg tttacccatt tgtcttttga   2580
agtgaaggct ggtgaggccg ttttaataac gggggcaaat ggtattggta aaagcagcct   2640
tttgcgtctg ttggcgggtt ttctgaaacc tttttcgggt catattgaaa aatggggtcg   2700
ggtggctttt gcggatgagg ctttggcaat ggatcggcat ttgcctttag aaaaagcctt   2760
ggcttattgg gcggctttag atggtgtttt gggcgctgaa aaagaagcaa tggcggtgat   2820
ggctcttgat atattggcgg attcacctgt ccgtttgctc tccactgggc agcgtaaaag   2880
agctgtgttg gcgcgtttgt tggcaagcca ggctgctatc tggttgttgg atgaaccggc   2940
aaacgggctt gatgcggctt ctgttagggc tttgatcgaa atgatagagc accatcgcca   3000
aaagggcggg attattttgg ctgttagtca tcaagggctt gatatggctg attataaaac   3060
cttgtcttta gaaaatttcg tagcgaattc tggccagtca tcaggtttct ttgacctttt   3120
```

-continued

```
ggatgaaagt catttctctt gatccggctt gttttgttaa ttcgtcggga ttgctcgatt   3180

ttgatcgggg caggggtatt tctacctgtc ttgttttttt tattggttgc cgttctattc   3240

cctttcgcgg tgggcagtga cgctataatt ttatcgcgta ctggtagcgg aatattatgg   3300

gttgcagctc tgttggcttc tttgttaccc attgaccgtt tgattattcc cgatgtcgaa   3360

aatggctttt tcgatcatta tgcggtgcgc gggattagcg aagaatggat agctgtggcg   3420

cgtattatcg cccattgggt gagttttgct gtccctttaa tggtggcgtt gttacccgcc   3480

tcggctttgc tatctttgga ttggtctgtt ttctggaaat tggaagccgg atttttattg   3540

gctactcctg gactggcctc tttgggggtt atgattgccg ctttgacggc aaggataaag   3600

tccggaagtg ggttggctgc tttactttta ttgcctttgg ccgtgccgct ccttatattt   3660

ggcgcggggg ctgttgatgg tcatcagcct ggggccttcc tattattggc ggcttgttcg   3720

ttgtttttgc tcgctgtcgc gccttttgtc atcggtgccg ctttgcgcgt cggacaagat   3780

gggtaaaagg cttactgtat cgatttaagg caggctttgt gattgatgaa gtcgagataa   3840

agagtgac                                                            3848
```

<210> SEQ ID NO 65
<211> LENGTH: 27
<212> TYPE: DNA
<213> ORGANISM: Artificial Sequence
<220> FEATURE:
<223> OTHER INFORMATION: Dldh-F

<400> SEQUENCE: 65

```
tgtttcaggc ggccgctatt ttaagtc                                         27
```

<210> SEQ ID NO 66
<211> LENGTH: 27
<212> TYPE: DNA
<213> ORGANISM: Artificial Sequence
<220> FEATURE:
<223> OTHER INFORMATION: Dldh-R

<400> SEQUENCE: 66

```
tctttatcgc ggccgcatca atcacaa                                         27
```

<210> SEQ ID NO 67
<211> LENGTH: 29
<212> TYPE: DNA
<213> ORGANISM: Artificial Sequence
<220> FEATURE:
<223> OTHER INFORMATION: Del-DldF

<400> SEQUENCE: 67

```
tttcttttgc agttaactgt cagcctgaa                                       29
```

<210> SEQ ID NO 68
<211> LENGTH: 28
<212> TYPE: DNA
<213> ORGANISM: Artificial Sequence
<220> FEATURE:
<223> OTHER INFORMATION: Del-DldR

<400> SEQUENCE: 68

```
tgatcctgta tggttaacaa ttgttgcc                                        28
```

<210> SEQ ID NO 69
<211> LENGTH: 3844
<212> TYPE: DNA
<213> ORGANISM: Artificial Sequence
<220> FEATURE:
<223> OTHER INFORMATION: Nucleotide sequence of upstream of Alcohol
dehydrogenase I (ZMO1236)

<400> SEQUENCE: 69

```
cttactcaat ggaacggcac catgatctga ttgcccgtat ggctggcaag tcaggggtcg     60

gttacgaaat gttgggtaaa agcctcgatg gtcaaagcat ggattgcctg acgatggggg    120

aagggcggcg ctctatctgg ttgatcgcac ggcaacatcc gggcgaaacc atggccgaat    180

ggtggatgga aggcgctttg gaaaggttaa ccgatgaaaa tgactcggtt gcgcgcctgc    240

ttcgccaaaa agcccgcttt catatcatgc ctaatatgaa tccggacggt tcttgccgtg    300

gtcatttgcg gacgaatgct tgtggtgcca atctcaatcg tgaatgggca gaacccacgg    360

ctgaacgcag ccccgaagtg ttggacgttc gcaatcatat ggacaaaacg ggcgttgatt    420

ttgtcatgga tgttcatggc gatgaagcta ttccgcatgt attccttgcc ggttttgaag    480

gtatccccga tctcgacaag gcacaggata aattattccg ccgctaccgg aataaattgg    540

ccaaatacac gcccgatttt caacgtcatt acggttatga aaatgacgag ccggggcagg    600

ccaatctagc cttggcgact aaccaattag cctatcgtta caaggcggtt tcgatgacgc    660

ttgaaatgcc tttcaaagat catgacgata tgcctgattt gaaaaaaggt tggtcaccgg    720

aaaggtcaaa acaattaggc cgcgattgtc tcgctatctt ggctgaaatg attgatcagc    780

tcccgatctc tggcaaagat ctcgcgtaat aaaactatca ggcgcaatcg taattttgcg    840

tctgatagag cttttcataa aggctataac cgctattgcc aaaagccata ggcctgcata    900

atctgacggc gaataatttt cctgaaagat tggcggccat tttgctgac cgcacagatt    960

gtcagcgtta attatacatg gcttcttttg ttgattcggg aactgcaagc gtttaccgga   1020

acaacacata acgaagagat attgaaaagg agtggaatat gcccacgctc gttttgtccc   1080

gtcacggaca gtccgaatgg aaccttgaaa accgtttcac cggttggtgg gatgttaacc   1140

tgactgaaca gggtgttcag gaagcaacgg ccggtggtaa agctctggct gaaaagggtt   1200

ttgaattcga tatcgctttc accagcgttc tgacccgcgc catcaaaacc accaatctta   1260

ttctcgaagc cggtaaaacc ctttgggttc cgaccgaaaa agattggcgt ttgaatgaac   1320

gtcactatgg tggtctgacc ggtctgaaca aggctgaaac cgccgctaaa catggtgaag   1380

aacaggttca tatttggcgc cgttcttatg acgttccgcc gcccccgatg gaaaaaggca   1440

gcaagttcga tctgtctggc gatcgccgtt atgatggtgt caagattcct gaaacggaaa   1500

gcctgaaaga caccgttgct cgcgtgctgc cttattggga agaacgcatt gcccctgaac   1560

tgaaggctgg caagcgcgtc ctgatcggtg cgcatggtaa ctcactgcgc gctctcgtta   1620

agcatctgtc gaaattgtcg gacgaagaaa tcgtcaaatt cgaattgccc accggtcagc   1680

cgttggtcta cgaattgaat gatgatctga ctccgaaaga tcgttacttc cttaacgaac   1740

gttaatagcc ttgggctttt aaagcctttt ggtttgttaa ccgtttttc ggccagagtt   1800

ttctctggcc gaaaatttat gtctatccct ttgtttttct atccccatca cctcggtttt   1860

gttgacaaaa aaaggtggcc actaaattgg ctttccgcac cgatgggatg atttttattc   1920

tttgctattc ttcgctcttt gcccaattca ttaaaagcgg aaatcatcac caaagataga   1980

agacgcagcc ttcaccattt cagattgccc ttctcgggca ttttctgctg ctagaatcct   2040

cttaaaaata ttaaattcca ctctattggt aatatgtttc cctctttagg gaacaaataa   2100

agcccttctt tgttctataa aagttagctt accgatttta caaaaaataa taccgcttca   2160

ttcaatcggt aatacatatc tttttcttc aaaaaacttt tcaagagggt gtctatgcgc   2220
```

```
gtcgcaatat tcagttccaa aaactatgac catcattcta ttgaaaaaga aaatgaacat   2280

tatggccatg accttgtttt tctgaatgag cggcttacca aagagacagc agaaaaagcc   2340

aaagacgcag aagctgtttg tatctttgtg aatgacgaag ccaatgccga agtgctggaa   2400

attttggcag gcttaggcat caagttggtt gctcttcgtt gcgccggtta taacaatgtc   2460

gatctcgatg cggccaaaaa gctgaatatc aaggttgtgc gcgtgcctgc ctattcgccc   2520

tattcggttg ccgaatatgc agtagggatg ttgctcaccc tgaatcggca aatttcacgc   2580

ggtttgaagc gggttcggga aaataacttc tccttggaag gtttgattgg ccttgatgtg   2640

catgacaaaa cagtcggcat tatcggtgtt ggtcatatcg ggagcgtctt tgcccatatt   2700

atgacccatg gttttggtgc caatgttatc gcctataaac cgcatccaga ccccgaattg   2760

gcgaaaaagg tcggtttccg cttcacctct ctcgatgaag tgatcgagac cagcgacatc   2820

atttcgcttc actgtccgct cacgccagaa aatcatcaca tgattaatga agaaacactg   2880

gcaagggcaa aaaaaggctt ttacctcgtc aataccagtc gcggcggctt ggttgatacc   2940

aaggcggtga ttaaatcgct gaaagccaaa catctcggcg gttatgcggc ggatgtttac   3000

gaagaggagg ggcctttatt cttcgaaaat cacgctgacg atattatcga agatgatatt   3060

ctcgaaaggt tgatcgcttt cccgaatgtg gttttcacgg gacatcaggc ctttttgacg   3120

aaagaggcct tatcaaacat tgctcacagt attctacaag atatcagcga tgccgaagct   3180

ggaaaagaaa tgccggatgc gcttgtttag tagacaagcg acaattaacc ttttgaagat   3240

cataatgatc aaatttttgg gttaattcgg tagttatggc ataggctatt acgcgctaat   3300

tgatatcaaa aaaaagcata gccggacatc ataccggcta tgttttttat taggaaaaaa   3360

tttcctttca ccttgcttag ccatcgccgc attatttaat caatatgccg agtttttctt   3420

gaaatcccta tcttacacca aggccaacaa gggaatcatc catactcggt gtcctatcct   3480

atgacttttt aaattttctc caaatttact aaaatcacgc catctcagcg gctgctattt   3540

tcaaaaagcg cctctcaaaa ccgctttttc ctgctcaaat atcggatccc aaaattccct   3600

caaaaaaggc agggtatttt ttacaaaatc gcccctaata tctctcaatc cgctgccttg   3660

ttcatatgtt tttgcaaatg atttttatta aactttttta ggcgtatttt tatcaagaaa   3720

atttaaataa tcacattttt attattttag atttaagtat tgatacaagt gatatctata   3780

aatgttttta taactttctg gatcgtaatc ggctggcaat cgttttccct atattcgcaa   3840

gatg                                                                3844
```

<210> SEQ ID NO 70
<211> LENGTH: 3861
<212> TYPE: DNA
<213> ORGANISM: Artificial Sequence
<220> FEATURE:
<223> OTHER INFORMATION: Nucleotide sequence of downstream of Alcohol dehydrogenase I (ZMO1236)

<400> SEQUENCE: 70

```
accagaaagg ctttttcttt gtcgtctgat aaaaattttc atacagaatt taatacagca     60

atcggtgcta taagccgcta tccaagcttt tttcttctca tgccttctat tcggcaatcg    120

ctatttaaag gctgttttta tggggcattc gccctatata taaggatatt agcgtttata    180

tataatagaa ggaaatctgg ccttgggtga aacaaccctc caagcagcgc cccatgccca    240

tattcaacat agcggctccg atttattgga agcggccaag gcggctttat tgaaatcggg    300

tgagcaatgg acagccatgc gtgcctccgt ttacaaagcc ttggcacaaa ccaacaagcc    360
```

-continued

```
aagttcagcc tatgatattg ccgatattgt ctctcaatcc gaaggacgca gagtagctgc    420
caacagcgtt tatcgcatcc tcgacatctt cgtcagtagc aatctcgcgc atcgggtcga    480
aagcgctaac gcctatatcg tcaacgccca tcctgaatgt cgtcatgact gcctttttct    540
cgtctgcgac caatgtgggg gtgtgattca tatagatgat gacaagatca gccgcttttt    600
aaaagaatcg gcagaaaaaa acgattttgt tgcagaaagg tctgttttag aaatacgggg    660
taaatgttca cattgtcttt cccattaacc taaatgtacc tcaggttaac ctgttgcaat    720
gactctatta cctgctatga ttttgtaact tttatgtcgc agtcagggct tatcttggct    780
aatttgggtt cctgctgttc acctttaggg cgaattgttt tactaaacag gcttaaattt    840
cggtttgatt taaggcccta agcttatgtt tccgaatgac aagacgccgc tgttagacaa    900
gatcaagaca ccggcagaat tgcgtcaatt agatcgcaac agcctccggc aattggcgga    960
tgaattacgg aaagagacca tctcggcagt gggtgtgacc ggcggacatc tcggttccgg   1020
tctgggggtt atcgaattaa cggtagccct tcactatgtt ttcaacacgc ccaaagacgc   1080
tttagtctgg gatgttgggc atcaaaccta tcctcacaag attttaacag gtcgccgcga   1140
tcgtattcgg acattgcggc aacgtgacgg cttatcgggc tttacgcagc gcgcggagag   1200
cgaatatgac gcttttggag ccgcgcatag ttcgacttct atttctgcgg cgctcggctt   1260
tgcgatggcc agcaaattat ccgacagcga cgacaaagcg gttgcgatta tcggtgatgg   1320
ctcgatgacg gcaggcatgg cttatgaagc catgaataac gccaaggcgg cgggtaagcg   1380
cctgattgtc attttgaatg acaatgaaat gtcgatttca ccgccggtgg gtgccttatc   1440
gtcttatttg agccgcctga tttcctcacg gcctttcatg aatttgcgcg atatcatgcg   1500
cggcgttgtt aaccggatgc caaaaggctt ggcaacggct gcccgcaagg ctgatgaata   1560
tgcgcgtggt atggcaaccg gtggcacctt ctttgaagag ctgggctttt actatgttgg   1620
ccccgtggat ggtcataatt tagatcagct cattccagtt ttagaaaatg tccgcgatgc   1680
caaggacggc cccattttgg tgcatgtcgt cactcgcaaa ggccaaggct atgctccggc   1740
tgaagcggcc aaggacaaat atcacgccgt gcagcgcttg gatgtggttt ccggtaagca   1800
ggcgaaagcg cccccgggac ctcccagcta tacctctgtt ttttcggaac agctgatcaa   1860
ggaagctaag caagacgata agattgtgac cattacggca gctatgccga ctggcaccgg   1920
tcttgatcgt tttcagcaat attttcctga aagaatgttt gatgtcggta ttgccgaaca   1980
acatgccgta acctttgcgg ctggtttggc ggctgccggt tacaagcctt tctgttgtct   2040
ctattcgacc ttcttgcagc gcggctatga ccagttggtg catgatgtcg ctatccagaa   2100
tttgccggtg cgcttcgccg tcgatcgtgc gggtcttgtc ggtgccgatg gggcaaccca   2160
tgcgggtagc ttcgacctcg cctttatggt taatctcccg aatatggtcg tgatggcgcc   2220
ttccgatgaa cgggaattgg ccaatatggt gcatagcatg gcgcattatg accaaggccc   2280
gatctcggtg cgttatccgc gtggtaatgg tgtgggtgtc tccttggaag gtgaaaagga   2340
aattctgcct atcgggaaag gtcgcctgat ccgtcgcggt aaaaaggttg ctatcctatc   2400
tctcggcact cgattggaag aatccttgaa ggctgctgat cggcttgatg ctcaaggttt   2460
gtcgacatcg gttgctgata tgcgttttgc taagcccttg gatgaagcgc tgacccgcca   2520
acttttgaaa agccatcagg tcattattac cattgaagaa ggcgctttgg gtggttttgc   2580
aacccaagtc ctgacgatgg cttcggatga aggcctgatg gatgacggat tgaaaatccg   2640
caccctgcgt ctgccggatc ggttccagcc gcaagacaag caagaacggc aatatgccga   2700
```

-continued

```
agccggtctt gatgctgatg gcatcgttgc tgcggttatc tccgcattgc atcgtaattc   2760

taaacccgtg gaagtcgtcg aaatggcgaa tatgggtagc atcgctcgcg cttaatttgc   2820

tattagggag cctcggctcc cgacaatagt aaagagatca tatataatgc tacatccggt   2880

tgttttgtgt ggtggttcag gtacacgtct tttcccgtta tcccgccgga gccatcccaa   2940

acaactcctc agcttgatgg gcgaaaatag cctgtttcag gacgctgtcg cacgtgtaac   3000

agattcttct ctattcacgg cacctcttgt tatctgcaat gaagaatacc gttttactat   3060

tgcagaacag ttgcaggaaa tgggcgttaa ggctcaagag attgtccttg agccagaagg   3120

ccggaacaca gcgcccgcga ttgctttagc ggcgtcaatg attgcagata aagatcctga   3180

tgcctgcatg ctgatcttac cgtcagatca cgttatccgg gatgtcaaag cattccatga   3240

agcaatcaaa gatgccgaaa ctattgcccg taaagcaaag gcacttgtga cttttggcgt   3300

acgcccaacc tctcctgaaa caggttacgg ttatatcgaa atgggtgaag cgctacctat   3360

agcgggtggc tatcatatcg acagattccg tgaaaaaccg gatatcaaga cggctgaaga   3420

ttacttagcc agtggtcgtt ttctctggaa tagcgggatg tttctttttc ccgtatcgcg   3480

gatattagaa gattttgcgc tttatcaatc cgatattttg gatgccgtta aagcctcttt   3540

acgcaagagc caaaaagacc tcgattttac gcgcctagat gcagaatcct ttgcgaaagc   3600

gccctctatt tcaatagatt atgcgatcat ggaaccggcc cataacagag ccgttgtccc   3660

cgttaatatc ggatggagtg atgtcggatc atggtcgtcc ctttgggcaa tcagtgatca   3720

tgacgataat ggtaatgttt taatgggcga tgtggtcgcc gaagattctt ctaattgtct   3780

tatccgctct gaaaacggct tggtcgcgac acttggcgtt aaagacctaa ccattatcaa   3840

cacttcagat gttactttgg t                                             3861
```

<210> SEQ ID NO 71
<211> LENGTH: 27
<212> TYPE: DNA
<213> ORGANISM: Artificial Sequence
<220> FEATURE:
<223> OTHER INFORMATION: Adh1-F

<400> SEQUENCE: 71

```
actcaatgga actgcagcat gatctga                                         27
```

<210> SEQ ID NO 72
<211> LENGTH: 31
<212> TYPE: DNA
<213> ORGANISM: Artificial Sequence
<220> FEATURE:
<223> OTHER INFORMATION: Adh1-R

<400> SEQUENCE: 72

```
accaaagtaa catctgcagt gttgataatg g                                    31
```

<210> SEQ ID NO 73
<211> LENGTH: 25
<212> TYPE: DNA
<213> ORGANISM: Artificial Sequence
<220> FEATURE:
<223> OTHER INFORMATION: Del-Adh1F

<400> SEQUENCE: 73
ttgcgaatat agtttaaacg attgc 25

<210> SEQ ID NO 74
<211> LENGTH: 26
<212> TYPE: DNA
<213> ORGANISM: Artificial Sequence
<220> FEATURE:
<223> OTHER INFORMATION: Del-Adh1R

<400> SEQUENCE: 74
accagaaagg tttaaacttt gtcgtc 26

<210> SEQ ID NO 75
<211> LENGTH: 3986
<212> TYPE: DNA
<213> ORGANISM: Artificial Sequence
<220> FEATURE:
<223> OTHER INFORMATION: Nucleotide sequence of upstream of Alcohol dehydrogenase II (ZMO1596)

<400> SEQUENCE: 75
cataaccgac atgcaaaata gccacccgca ttttttggg cgtgacaaaa caagcaccat 60
agccaatcgc ctcaccggcg ctgacttctc ttacctgaat ggcttgggcg gcaatagcaa 120
cgacgggttt cagaatatct ttggattgcg gaacaggcag gccgccgtaa agcgccaagc 180
ccggacgcgc cagatcaaaa tgatagtctt tgctgagaaa aataccggca gaattagcca 240
aactatagcg ttttgcctgt tttctggcgg ctaaaatccg aaagcgttca agctgctttt 300
gattaagcgg gtgatctgcc tcgtctgcac aggccagatg gctcaaaata ttgtcgatag 360
aaagaccatc cagcaggcct gaacccgcct cttccatcga aagacccagc cgattcattc 420
cagtatcgac catgacatcg cagggacggt tcggcgcgtg agctttccag cgggcaatca 480
tcgctggact acataaaacc ggcttgaccg aagaattcag agcatagccg aggtcatctt 540
cccttaggcc atggagaaca gaaagggaga aatccttttc cgaactatcg agtaagcgag 600
cttcatccca actggaaaca aaaaaatcgc gacatccggc ctgtgccaga taatgacgaa 660
cgcgttcagc ccctaaacca tagccattag ccttgatcgc ggcaccacaa tgaccagccg 720
ttatccggtt caaactttgc cagtttgcca tcagggctga tttgtctaat tccagacgga 780
gaggagaaga aatctgcact ctttttaat aagactgaaa aagcagtcag gcaagcaccg 840
aaatcggctt tatacctgac tgcttttcat catggatcaa aattagtttt tggctgcgag 900
taaatcctcg agatagctat gggttttatc gattttctca aggcgcgggt aacgcaagcc 960
gtcataataa ggaatcgcga catcccgata attatcgcct tgcttgatga gcaatttgat 1020

```
cggcgtttta ttggccttgg catttttgat cgctgttttt agcagatcat tgctaaaggc   1080
atgaccatca accgcgacca attcacttcc tacggtcaat ccagcgttaa aggcagggct   1140
atcccacatc accgaagaga ctttgccttt ttcagaagtc gataatccca aagagaaaga   1200
caactcggcc atatggcgtg cgccttcaac acctttgatc cagtcggttg gctcatcact   1260
gtaaaccagt ttgtaaccgc cacggctgat ccagtccaaa ggcgcatggg tcgaacgctg   1320
attcaaacgc tggttaaaga aggctgccca gtcataaggc atgatgtcat ttaaggtttt   1380
gacgacatcg tcaaaattat aggttaactc accccaatca cggtcacgca ttccgaaaaa   1440
ggcttttgca aaatcgtcaa gcgaatgttt gccatgagtt tgttgccgga gcaggctatc   1500
aacatcaagc cagatcaact gaccttcact gtagtaatct tcggaacgtt gccagcttag   1560
ccagcctttg gggcggcgtt gcgaaataat cggatcatta gtggtatctt ccaccggacg   1620
ccaacggcgg cctgcccgat tgtcgtaagt ggcggccacc aaagccaagg cttccaaggc   1680
atctttttgc tgccacagac cggaacgcgc ggccaataca taaccccaaa actgggtttg   1740
accttcataa acccaaagga ggctatcccg catcggcgtt ttatagtccg gtgtccaaag   1800
atcagcgggg cggcgatatt taccattcca gctatggtta tattcatggg cgaggagatc   1860
acgaccaacg gctgatttat cccatttcga gaagtaatca gccccttccc catcttcgga   1920
agattggtga tgttctaaac caataccacc gagcttttcg gacaaagcca gcaagaaatc   1980
ataatggcta taatgttgtg cgccgtaaag ttttacggct tgggttatga gctggcgatg   2040
cgcgttaagc tgtttgtccg tcatcaccat atcttcgggt ttgtctgcta taagattgag   2100
acgaaccccg ggggcgagcg tttctgtccg cgtataacga cccgccatta ccggcgaatc   2160
aattagcgta tcaaaatcgg tagttttata ttggacgaca ttgggtgtct gtccatcagg   2220
cgtgatacca gaaatttcta aggcagaagc cgatttccaa cccgttggat aaataacggt   2280
cggctgtatc tggatttggc gggtaaaata tccggccgga tataaagcca gcgtattcca   2340
ctgcaaattg accatttccg gtgtggactg gattcttccc tgcgactccg aagtcgggga   2400
gagatattga tattgggcgg tgatttcggt cacgcctgcc ggaatatcaa gatgaaaggc   2460
ataaacatcg acagaatcgc gttgccaagg aataacctga ttattggcgg taacaatcaa   2520
acctgccaat ttttcgatgg gacctgatgg actatgatgt cccggcaacc attcaggata   2580
gagcaaagtc agcgcaccag cctgaacagg aatcgtttcc gttacccgaa caataccgcg   2640
ctgcgtgtct gtggcatcga cattaagacg aatgagaccg ctataaggtt tatcaaccgc   2700
agccggaatc gtttcagata tcgccatagg ttgaggtgca gaatttccag ctggtatcgc   2760
ttgtgcctgc caagcgatgg cactggtcgc tagcaaaaat agcaaggaac gcttcataaa   2820
aatatatccc cccgttgaat cattgtttcc aaaacagcat catcttactg atttttgttt   2880
aaaaacaaca aagattgtct cgtcgagact gtaaatagat aaaatatccg cttccacata   2940
aaagcggcaa aaattttcaa aatttctttt attttttcat taccgctgca attttttttg   3000
```

```
tctttttgcg ttttttgagg aaagcctgat ctgccatttt gagcagaaga aagaacaagc   3060

tgcttttgat gcagcgtttg agacaattga ttagatcaaa aatggaaacg ataattttct   3120

tttttttcta tttttattat ggatgaatat ccctatttcg gcagagcggg tggcggtagc   3180

acttcccccc cctcctcctc aagctaccgc gacccccata gcttcttttc ctgactattc   3240

ccctgcatcc ttacaaatta ttcttttatt tctttttcac aatctatttg gatatctgaa   3300

aatgtcttta ttttaatgtt gtgcaattta tacagtatat ttcgccatat acgatatttt   3360

cttgttttct atttacaatt tggcttttaa tatttgaaca ataaattgga atgaatacct   3420

aacaactatg ttatttttag tcttatcttt ctctaaaaag cctcaaaaac gaacaaaata   3480

acagattctt caaaatttcc tttcttaaaa tttaacataa atgttttatt ttaaaatatt   3540

tcgcctgaaa tttattattt taatttaaag gcaaaatcgg taaccacatc tcaattatta   3600

aacaatactt cataataaaa agacaacttt ttcataattt gcataagtct tgatgtaaaa   3660

aatacatatt tagaaagaac aagcagcctt gctcatcacc gctgtcgcga gtagaaaaat   3720

ctcggctttc agaaaataga ggtcgcttcg ttaaacagac tataaatgtg ctggaataaa   3780

gcgaacccct tgatctgata aaactgatag acatattgct tttgcgctgc ccgattgctg   3840

aaaatgcgta aaattggtga ttttactcgt tttcaggaaa aactttgaga aaacgtctcg   3900

aaaacgggat taaaacgcaa aaacaataga aagcgatttc tcgaaaatgg ttgttttcgg   3960

gttgttgctt taaactagta tgtagg                                        3986
```

<210> SEQ ID NO 76
<211> LENGTH: 3868
<212> TYPE: DNA
<213> ORGANISM: Artificial Sequence
<220> FEATURE:
<223> OTHER INFORMATION: Nucleotide sequence of downstream of Alcohol dehydrogenase II (ZMO1596)

<400> SEQUENCE: 76

```
ctgtcttgat tttcaagcaa acaatgcctc cgatttctaa tcggaggcat ttgtttttgt     60

ttattgcaaa aacaaaaaat attgttacaa atttttacag gctattaagc ctaccgtcat    120

aaataatttg ccatttaaag cctattatca ggattttcgc cccgatttca gccatggcag    180

aaatcttttc gggtttaata gcgggaaatt ctttgatagc tggccttttg ctcgcctgct    240

ttattatttt tacatccagg cggtgaaagt gtacagaaaa gccgcgtttg ccttatgaag    300

gcgacgaaat atttttcaga taaagtcttt accttgttaa aaccgctttt cgttttatcg    360

ggtaaatgcc taatgcagag tttgatttca ggcctatgtt tccgaataaa aagacgccgt    420

tgttagacaa gatcaagaca ccggcagaat tgcgtcaatt agatcgcaac agcctccggc    480

aattggcgga tgaattacgg aaagagacca tctcggcagt gggtgtgacc ggcggacatc    540

tcggttccgg tctgggggtt atcgaattaa cggtagctct tcattatgtt ttcaacacgc    600

ccaaagacgc tttggtctgg gatgttgggc atcaaaccta tcctcacaag attttaacag    660

gtcgccgtga tcgtattcgg acattgcggc aacgtgacgg cttatcgggc tttacgcagc    720
```

```
gcgcggagag cgaatatgac gcttttggag cagcgcatag ttcgacttct atttctgcgg    780
cgctcggctt tgcgatggcc agcaaattat ccgacagcga cgacaaagcg gttgcgatta    840
tcggtgatgg ctcgatgacg gcaggcatgg cttatgaagc catgaataac gccaaggcgg    900
cgggtaagcg cctgattgtc attttgaatg acaatgaaat gtcgatttca ccgccggtgg    960
gtgccttatc gtcttatttg agccgcctga tttcctcacg gcctttcatg aatttgcgcg   1020
atatcatgcg cggtgttgtc aaccggatgc caaaaggctt ggcaacggct gcccgcaagg   1080
ctgatgaata tgcgcgtggt atggcaaccg gtggcacctt ctttgaagag ctgggctttt   1140
actatgttgg ccccgtagat ggtcataatt tagatcagct cattccggtt ttggaaaatg   1200
tccgcgatgc caaggacggc cccattttgg tgcatgtcgt cacccgcaaa ggccaaggct   1260
atgctccggc tgaagcggcc aaggacaaat atcacgccgt gcagcgcttg gatgtggttt   1320
ccggcaagca ggcgaaagcg cccccagggc ctcccagcta tacctctgtt ttctcggaac   1380
agctgatcaa ggaagctaag caagacgata agattgtgac cattacggca gctatgccga   1440
ctggcaccgg tcttgatcgc ttccagcaat attttcctga aagaatgttt gatgtcggta   1500
ttgccgaaca acatgccgta acctttgcgg ctggtttggc ggctgccggt tacaagcctt   1560
tctgttgtct ctattcgacc ttcttgcagc gcggctatga ccagttagtg catgatgtcg   1620
ctatccagaa tttgccggtg cgcttcgccg tcgatcgtgc gggtcttgtc ggtgccgatg   1680
gggcaaccca tgcgggtagc ttcgacctcg cctttatggt taatctaccg aatatggtcg   1740
tgatggcgcc ttccgatgaa cgggaattgg ccaatatggt gcatagcatg gcgcattatg   1800
accaaggccc gatctcggtg cgttatccgc gtggtaatgg tgtgggtgtc tccttggaag   1860
gcgaaaagga aattctgcct atcgggaaag gtcgcctgat ccgtcgcggt aaaaaggttg   1920
ctatcctatc tctcggcact cgattggaag aatccttgaa ggctgctgat cggcttgatg   1980
ctcaaggttt gtcgacatcg gttgctgata tgcgttttgc taagcccttg gatgaagcgc   2040
tgacccgcca acttctaaaa agccatcagg tcattattac cattgaagaa ggcgctttgg   2100
gtggttttgc aacccaagtc ctgacgatgg cttcggatga aggcctgatg gatgacggat   2160
tgaaaatccg caccctgcgt ctgccggatc ggttccagcc gcaagacaag caagaacggc   2220
aatatgccga agctggtctt gatgctgatg gcatcgttgc tgccgtaacg gctgcattac   2280
aacggaactc aaagcctgtc gaagtcgttg agctgactac aaaagtaaca gaagatatga   2340
ctttatgatc caagttatct tttattctga atcgtccggt tgtaacagct aaggcgcttg   2400
ggctagccat acggattgat ctcgtgatat cggacacatc atgcatcgtt ttcttgtaac   2460
gcgtctcgca ggtataagct gtcgctttcc tctgcctgtt ctcgccttca cccttttctt   2520
aacgctggtc tctgcctatt tcgcggcgag ccattttgcg atcaatacgg atacggcgac   2580
ccttatttct cccaaggtaa cctatcgcgt caatgaagat agatttgccg atgcttttcc   2640
atctacaggg gggacaaccc tgatcgttgt ggaaggacaa acaccggaat tggcagaatc   2700
tgctgccgcc cgattaagcg agaaattggg acaggataaa aagcattttc tgacggtgac   2760
gcgacctgat ggcggcgaat tttttgcccg tgaaggtatc ttgttcggcc agttgccgga   2820
tgttcaagat acgatgcaac agctgatttc agcacagcct tttttaggcc ctctggcttc   2880
cgatccttct ttacgaggga ttaataacgc cctgaatacc atgttgatgg gggtcaaccg   2940
ccatatggct aatctggatc aaatccagac cccaatccgt tcgattgata aggctatccg   3000
tgaccagctt tctggaaaac agacatggtt ttcttggcaa ctgcttttct caagcaaaaa   3060
```

-continued

```
tccagcactg aaaccgcctc taaaacggtt aattttggca cagcctgttc ttgatctaag   3120

tgctttgatg ccggggattg aggccagcaa tgctattcat aaggccgcta gtgatctgaa   3180

attggatgcc gatcatggcg tcgatatccg tttaaccgga tctgtgcctt tggcggatga   3240

agaatttgct tctttagcgg ataaaatctg gttggttgca ggcgcaatga ttggcgcgat   3300

gcttatcacc ctgtggttgg cggtgcgttc ccccagtatt gttgcggcaa ttatgttgac   3360

gaccattgcc ggattgattg tgacggctgc ggttggtctg ataacagtcg ggcgatttaa   3420

ccttatttct gtcgccttta ttccgctttt tgtcggttta ggggtggatt ttgggattca   3480

gctttcggta cgttttttag ctgaattgga aacagaaccc aatcagccca cggcactttt   3540

gaacgctgcc aatgcgttgg gtcattcctt gttattggca gccggtgccg tttgccttgg   3600

ttttctgtcc tttttgccga cagcctatat cgggatttcc gaattaggga tgattgccgg   3660

tgtcggtatt ttgattgcct tgttcttctc ggtaacgatg ctgcccgcct ttttaatgct   3720

gtttcgccct cgtccaccgc ggcatcatgt gggttggcgc aatatggcgc cagtcgatca   3780

ttttctggtt aaagaaagac gttgggttat cggaagcttt ttggggctga ccctgattag   3840

catcattctt ctgccttggg tacaattc                                      3868


<210> SEQ ID NO 77
<211> LENGTH: 24
<212> TYPE: DNA
<213> ORGANISM: Artificial Sequence
<220> FEATURE:
<223> OTHER INFORMATION: Adh2-F

<400> SEQUENCE: 77

cataaccgac ctgcagaata gcca                                            24


<210> SEQ ID NO 78
<211> LENGTH: 24
<212> TYPE: DNA
<213> ORGANISM: Artificial Sequence
<220> FEATURE:
<223> OTHER INFORMATION: Adh2-R

<400> SEQUENCE: 78

tgtacccact gcagaagaat gatg                                            24


<210> SEQ ID NO 79
<211> LENGTH: 26
<212> TYPE: DNA
<213> ORGANISM: Artificial Sequence
<220> FEATURE:
<223> OTHER INFORMATION: Del-Adh2F

<400> SEQUENCE: 79

cctacatact agtttaaacc aacaac                                          26


<210> SEQ ID NO 80
<211> LENGTH: 27
<212> TYPE: DNA
<213> ORGANISM: Artificial Sequence
<220> FEATURE:
<223> OTHER INFORMATION: Del-Adh2R

<400> SEQUENCE: 80

ctgtcttgat gtttaaacaa acaatgc                                         27
```